US012221627B2

(12) United States Patent
Cafri et al.

(10) Patent No.: US 12,221,627 B2
(45) Date of Patent: Feb. 11, 2025

(54) METHODS OF ENRICHING CELL POPULATIONS FOR CANCER-SPECIFIC T CELLS USING IN VITRO STIMULATION OF MEMORY T CELLS

(71) Applicant: The United States of America, as represented by the Secretary, Department of Health and Human Services, Bethesda, MD (US)

(72) Inventors: Gal Cafri, Kibbutz Nir David (IL); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 695 days.

(21) Appl. No.: 16/768,930

(22) PCT Filed: Dec. 3, 2018

(86) PCT No.: PCT/US2018/063563
§ 371 (c)(1),
(2) Date: Jun. 2, 2020

(87) PCT Pub. No.: WO2019/112932
PCT Pub. Date: Jun. 13, 2019

(65) Prior Publication Data
US 2021/0052642 A1    Feb. 25, 2021

Related U.S. Application Data

(60) Provisional application No. 62/594,262, filed on Dec. 4, 2017.

(51) Int. Cl.
| | | |
|---|---|---|
| C12N 5/0784 | (2010.01) | |
| A61K 39/00 | (2006.01) | |
| C07K 14/725 | (2006.01) | |
| C12N 5/0783 | (2010.01) | |

(52) U.S. Cl.
CPC ........ *C12N 5/0639* (2013.01); *A61K 39/4611* (2023.05); *A61K 39/4632* (2023.05); *A61K 39/46447* (2023.05); *C07K 14/7051* (2013.01); *C12N 5/0636* (2013.01); *A61K 2239/50* (2023.05); *C12N 2506/115* (2013.01)

(58) Field of Classification Search
None
See application file for complete search history.

(56) References Cited

U.S. PATENT DOCUMENTS

| 8,034,334 B2 | 10/2011 | Dudley et al. |
| 2012/0244133 A1 | 9/2012 | Rosenberg et al. |
| 2017/0224800 A1 | 8/2017 | Tran et al. |

FOREIGN PATENT DOCUMENTS

| WO | 2016/053338 A1 | 4/2016 |
| WO | 2016/179006 A1 | 11/2016 |
| WO | 2018/057447 A1 | 3/2018 |

OTHER PUBLICATIONS

D'Souza, 1998, INt. J. Canc. vol. 78: 699-706.*
Carey, Clin. Breast Canc. vol. 10: 188-195.*
Carey, 2010, Clin. Breast. Canc. vol. 10: 188-195.*
Berger et al., "Adoptive Transfer of Effector CD8+ T Cells Derived From Central Memory Cells Establishes Persistent T Cell Memory in Primates," *J. Clin. Invest.*, 118(1): 294-305 (2008).
Bolger et al., "Trimmomatic: A Flexible Trimmer for Illumina Sequence Data," *Bioinformatics*, 30(15): 2114-2120 (2014).
Cafri, G., "Immunotherapeutic targeting of somatic mutations in human cancers," presentation to Sheba Hospital, Israel, Jun. 29, 2017.
Cafri et al., "Memory T cells targeting oncogenic mutations detected in peripheral blood of epithelial cancer patients," *Nat. Commun.*, 10(1): 449 (2019).
Cohen et al., "Enhanced Antitumor Activity of Murine-Human Hybrid T-Cell Receptor (TCR) in Human Lymphocytes is Associated with Improved Pairing and TCR/CD3 Stability," *Cancer Res.*, 66(17): 8878-8886 (2006).
Dobin et al., "STAR: ultrafast universal RNA-seq aligner," *Bioinformatics*, 29(1): 15-21 (2013).
Gattinoni et al., "A human memory T-cell subset with stem cell-like properties," *Nat. Med.*, 17(10): 1290-1297 (2012).
Gattinoni et al., "Paths to Stemness: Building the Ultimate Antitumour T Cell," *Nat. Rev. Cancer*, 12(10): 671-684 (2012).
Gros et al., "PD-1 identifies the patient-specific CD8+tumor-reactive repertoire infiltrating human tumors," *J. Clin. Invest.*, 124(5): 2246-2259 (2014).
Gros et al., "Prospective identification of neoantigen-specific lymphocytes in the peripheral blood of melanoma patients," *Nat. Med.*, 22(4): 433-438 (2016).
Hruban et al., "K-ras Oncogene Activation in Adenocarcinoma of the Human Pancreas. A Study of 82 Carcinomas Using a Combination of Mutant-Enriched Polymerase Chain Reaction Analysis and Allele-Specific Oligonucleotide Hybridization," *Am. J. Pathol.*, 143(2): 545-554 (1993).
International Bureau, International Search Report and Written Opinion in International Application No. PCT/US2018/063563, mailed Feb. 2, 2019.
Parkhurst et al., "Isolation of T-Cell Receptors Specifically Reactive with Mutated Tumor-Associated Antigens from Tumor-Infiltrating Lymphocytes Based on CD137 Expression," *Clin. Cancer Res.*, 23(10): 2491-2505 (2017).

(Continued)

*Primary Examiner* — Amy E Juedes
(74) *Attorney, Agent, or Firm* — Leydig, Voit & Mayer

(57) ABSTRACT

Disclosed are methods of obtaining a cell population enriched for T cells having antigenic specificity for a cancer-specific mutation using in vitro stimulation of memory T cells. Also disclosed are related methods of isolating a T cell receptor (TCR), populations of cells, TCRs or antigen-binding portions thereof, pharmaceutical compositions, and methods of treating or preventing cancer.

11 Claims, 32 Drawing Sheets

Specification includes a Sequence Listing.

(56) References Cited

OTHER PUBLICATIONS

Pasetto et al., "Tumor- and neoantigen-reactive T-cell receptors can be identified based on their frequency in fresh tumor," *Cancer Immunol. Res.*, 4(9): 734-743 (2016).

Rajasagi et al., "Systematic identification of personal tumor-specific neoantigens in chronic lymphocytic leukemia," *Blood*, 124(3): 453-462 (2014).

Robbins et al., "Mining Exomic Sequencing Data to Identify Mutated Antigens Recognized by Adoptively Transferred Tumor-Reactive T Cells," *Nat. Med.*, 19(6): 747-752 (2013).

Ronaghi et al., "A Sequencing Method Based on Real-Time Pyrophosphate," *Science*, 281(5375): 363-365 (1998).

Russo et al., "Mutational Analysis and Clinical Correlation of Metastatic Colorectal Cancer," *Cancer*, 120(10): 1482-1490 (2014).

Tran et al., "Cancer immunotherapy based on mutation-specific CD4+ T cells in a patient with epithelial cancer" and Supplementary Material, *Science*, 344(6184): 641-645 (2014).

Tran et al., "Immunogenicity of somatic mutations in human gastrointestinal cancers," *Science*, 350(6266): 1387-90 (2015).

Trolle et al., "Automated Benchmarking of peptide-MHC Class I Binding Predictions," *Bioinformatics*, 31(13): 2174-2181 (2015).

Turcotte et al., "Tumor-reactive CD8+ T Cells in Metastatic Gastrointestinal Cancer Refractory to Chemotherapy," *Clin. Cancer Res.*, 20(2): 331-343 (2013).

Voelkerding et al., "Next-generation Sequencing: From Basic Research to Diagnostics," *Clin. Chem.*, 55(4): 641-658 (2009).

Wang et al., "Phenotypic and Functional Attributes of Lentivirus-Modified CD19- specific Human CD8+ Central Memory T Cells Manufactured at Clinical Scale," *J. Immunother.*, 35(9): 689-701 (2012).

Wolfl et al., "Antigen-specific activation and cytokine-facilitated expansion of naive, human CD8+ T cells," *Nat. Protoc.*, 9(4): 950-966 (2014).

Zhang et al., "The Impact of Next-Generation Sequencing on Genomics," *J. Genet. Genomics*, 38(3): 95-109 (2011).

\* cited by examiner

SEQUENCE LISTING

```
<160> NUMBER OF SEQ ID NOS: 39

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Ser Gly Ser Gly
1

<210> SEQ ID NO 2
<211> LENGTH: 14
<212> TYPE: PRT
<213> ORGANISM: Homo sapiens

<400> SEQUENCE: 2

Cys Ala Ser Gly Val Ala Glu Ser Ser Tyr Glu Gln Tyr Phe
1               5                   10

<210> SEQ ID NO 3
<211> LENGTH: 18
<212> TYPE: PRT
<213> ORGANISM: Homo sapiens

<400> SEQUENCE: 3

Cys Ala Ser Gly Leu Val Ser Gly Gln Gly Ala Gly Val Thr Glu Ala
1               5                   10                  15

Phe Phe

<210> SEQ ID NO 4
<211> LENGTH: 14
<212> TYPE: PRT
<213> ORGANISM: Homo sapiens

<400> SEQUENCE: 4

Cys Ala Ser Ser Ser Gly Thr Ser Ala Asp Thr Gln Tyr Phe
1               5                   10

<210> SEQ ID NO 5
```

```
<211> LENGTH: 12
<212> TYPE: PRT
<213> ORGANISM: Homo sapiens

<400> SEQUENCE: 5

Cys Ala Ser Ser Gln Gly Ser Tyr Glu Gln Tyr Phe
1               5                   10

<210> SEQ ID NO 6
<211> LENGTH: 15
<212> TYPE: PRT
<213> ORGANISM: Homo sapiens

<400> SEQUENCE: 6

Cys Ser Ala Arg Glu Gly Ala Gly Gly Met Gly Thr Gln Tyr Phe
1               5                   10                  15

<210> SEQ ID NO 7
<211> LENGTH: 18
<212> TYPE: PRT
<213> ORGANISM: Homo sapiens

<400> SEQUENCE: 7

Cys Val Ser Gly Leu Val Ser Gly Gln Gly Ala Gly Val Thr Glu Ala
1               5                   10                  15

Phe Phe

<210> SEQ ID NO 8
<211> LENGTH: 15
<212> TYPE: PRT
<213> ORGANISM: Homo sapiens

<400> SEQUENCE: 8

Cys Ala Ser Ser Leu Thr Ser Gly Gly Phe Asp Glu Gln Phe Phe
1               5                   10                  15

<210> SEQ ID NO 9
<211> LENGTH: 17
<212> TYPE: PRT
<213> ORGANISM: Homo sapiens

<400> SEQUENCE: 9

Cys Ala Ser Ser Val Thr Gly Gly Ser Tyr Pro Asn Thr Glu Ala Phe
1               5                   10                  15

Phe

<210> SEQ ID NO 10
<211> LENGTH: 18
<212> TYPE: PRT
<213> ORGANISM: Homo sapiens

<400> SEQUENCE: 10

Cys Ala Ser Ser Glu Ala Leu Ser Gly Gly Ala Phe Gly Gly Glu Leu
1               5                   10                  15

Phe Phe

<210> SEQ ID NO 11
<211> LENGTH: 18
<212> TYPE: PRT
<213> ORGANISM: Homo sapiens

<400> SEQUENCE: 11

Cys Ala Ser Ser Glu Asn Leu Ala Gly Ala Ala Asn Thr Gly Glu Leu
```

Phe Phe

<210> SEQ ID NO 12
<211> LENGTH: 15
<212> TYPE: PRT
<213> ORGANISM: Homo sapiens

<400> SEQUENCE: 12

Cys Ala Ser Ser Leu Gln Gly Ala Met Asn Thr Glu Ala Phe Phe
1               5                   10                  15

<210> SEQ ID NO 13
<211> LENGTH: 14
<212> TYPE: PRT
<213> ORGANISM: Homo sapiens

<400> SEQUENCE: 13

Cys Ala Ser Ser Val Ser Leu Thr Gln Tyr Gly Tyr Thr Phe
1               5                   10

<210> SEQ ID NO 14
<211> LENGTH: 14
<212> TYPE: PRT
<213> ORGANISM: Homo sapiens

<400> SEQUENCE: 14

Cys Ser Val Asp Glu Arg Gly Gly Thr His Gly Tyr Thr Phe
1               5                   10

<210> SEQ ID NO 15
<211> LENGTH: 14
<212> TYPE: PRT
<213> ORGANISM: Homo sapiens

<400> SEQUENCE: 15

Cys Ser Ala Leu Gly Gly Gly Asn Thr Gly Glu Leu Phe Phe
1               5                   10

<210> SEQ ID NO 16
<211> LENGTH: 18
<212> TYPE: PRT
<213> ORGANISM: Homo sapiens

<400> SEQUENCE: 16

Cys Val Ser Gly Leu Val Ser Gly Gln Gly Ala Gly Val Thr Glu Ala
1               5                   10                  15

Phe Phe

<210> SEQ ID NO 17
<211> LENGTH: 15
<212> TYPE: PRT
<213> ORGANISM: Homo sapiens

<400> SEQUENCE: 17

Cys Ala Ser Ser Leu Thr Ser Gly Gly Phe Asp Glu Gln Phe Phe
1               5                   10                  15

<210> SEQ ID NO 18
<211> LENGTH: 17
<212> TYPE: PRT
<213> ORGANISM: Homo sapiens

<400> SEQUENCE: 18

Cys Ala Ser Ser Val Thr Gly Gly Ser Tyr Pro Asn Thr Glu Ala Phe
1               5                   10                  15

Phe

<210> SEQ ID NO 19
<211> LENGTH: 18
<212> TYPE: PRT
<213> ORGANISM: Homo sapiens

<400> SEQUENCE: 19

Cys Ala Ser Ser Glu Ala Leu Ser Gly Gly Ala Phe Gly Gly Glu Leu
1               5                   10                  15

Phe Phe

<210> SEQ ID NO 20
<211> LENGTH: 18
<212> TYPE: PRT
<213> ORGANISM: Homo sapiens

<400> SEQUENCE: 20

Cys Ala Ser Ser Glu Asn Leu Ala Gly Ala Ala Asn Thr Gly Glu Leu
1               5                   10                  15

Phe Phe

<210> SEQ ID NO 21
<211> LENGTH: 15
<212> TYPE: PRT
<213> ORGANISM: Homo sapiens

<400> SEQUENCE: 21

Cys Ala Ser Ser Leu Gln Gly Ala Met Asn Thr Glu Ala Phe Phe
1               5                   10                  15

<210> SEQ ID NO 22
<211> LENGTH: 14
<212> TYPE: PRT
<213> ORGANISM: Homo sapiens

<400> SEQUENCE: 22

Cys Ala Ser Ser Val Ser Leu Thr Gln Tyr Gly Tyr Thr Phe
1               5                   10

<210> SEQ ID NO 23
<211> LENGTH: 14
<212> TYPE: PRT
<213> ORGANISM: Homo sapiens

<400> SEQUENCE: 23

Cys Ser Val Asp Glu Arg Gly Gly Thr His Gly Tyr Thr Phe
1               5                   10

<210> SEQ ID NO 24
<211> LENGTH: 14
<212> TYPE: PRT
<213> ORGANISM: Homo sapiens

<400> SEQUENCE: 24

Cys Ser Ala Leu Gly Gly Gly Asn Thr Gly Glu Leu Phe Phe
1               5                   10

<210> SEQ ID NO 25
<211> LENGTH: 17

<212> TYPE: PRT
<213> ORGANISM: Homo sapiens

<400> SEQUENCE: 25

Cys Ala Ser Ser Val Thr Gly Gly Ser Tyr Pro Asn Thr Glu Ala Phe
1               5                   10                  15

Phe

<210> SEQ ID NO 26
<211> LENGTH: 12
<212> TYPE: PRT
<213> ORGANISM: Homo sapiens

<400> SEQUENCE: 26

Cys Ala Ser Ser Gly Pro Gly Glu Thr Gln Tyr Phe
1               5                   10

<210> SEQ ID NO 27
<211> LENGTH: 16
<212> TYPE: PRT
<213> ORGANISM: Homo sapiens

<400> SEQUENCE: 27

Cys Ala Ser Ser Leu Ala Lys Gly Pro Gly Asn Thr Glu Ala Phe Phe
1               5                   10                  15

<210> SEQ ID NO 28
<211> LENGTH: 17
<212> TYPE: PRT
<213> ORGANISM: Homo sapiens

<400> SEQUENCE: 28

Cys Ala Ser Ser Val Thr Gly Gly Ser Tyr Pro Asn Thr Glu Ala Phe
1               5                   10                  15

Phe

<210> SEQ ID NO 29
<211> LENGTH: 13
<212> TYPE: PRT
<213> ORGANISM: Homo sapiens

<400> SEQUENCE: 29

Cys Ala Ser Arg Gly Thr Glu Gly Thr Glu Ala Phe Phe
1               5                   10

<210> SEQ ID NO 30
<211> LENGTH: 18
<212> TYPE: PRT
<213> ORGANISM: Homo sapiens

<400> SEQUENCE: 30

Cys Ala Ser Ser Glu Ala Leu Ser Gly Gly Ala Phe Gly Gly Glu Leu
1               5                   10                  15

Phe Phe

<210> SEQ ID NO 31
<211> LENGTH: 18
<212> TYPE: PRT
<213> ORGANISM: Homo sapiens

<400> SEQUENCE: 31

Cys Ala Ser Ser Glu Asn Leu Ala Gly Ala Ala Asn Thr Gly Glu Leu
1               5                   10                  15

Phe Phe

<210> SEQ ID NO 32
<211> LENGTH: 15
<212> TYPE: PRT
<213> ORGANISM: Homo sapiens

<400> SEQUENCE: 32

Cys Ala Ser Ser Leu Gln Gly Ala Met Asn Thr Glu Ala Phe Phe
1               5                   10                  15

<210> SEQ ID NO 33
<211> LENGTH: 17
<212> TYPE: PRT
<213> ORGANISM: Homo sapiens

<400> SEQUENCE: 33

Cys Ala Ser Ser Pro Arg Thr Gly Gly Thr Thr Ile Gly Glu Gln Phe
1               5                   10                  15

Phe

<210> SEQ ID NO 34
<211> LENGTH: 14
<212> TYPE: PRT
<213> ORGANISM: Homo sapiens

<400> SEQUENCE: 34

Cys Ala Ser Ser Val Ser Leu Thr Gln Tyr Gly Tyr Thr Phe
1               5                   10

<210> SEQ ID NO 35
<211> LENGTH: 13
<212> TYPE: PRT
<213> ORGANISM: Homo sapiens

<400> SEQUENCE: 35

Cys Ala Trp Ser Arg Gly Gly Asn Gln Pro Gln His Phe
1               5                   10

<210> SEQ ID NO 36
<211> LENGTH: 17
<212> TYPE: PRT
<213> ORGANISM: Homo sapiens

<400> SEQUENCE: 36

Cys Ala Ser Ser Asn Ser Gly Ala Ala Val Asp Thr Asp Thr Gln Tyr
1               5                   10                  15

Phe

<210> SEQ ID NO 37
<211> LENGTH: 14
<212> TYPE: PRT
<213> ORGANISM: Homo sapiens

<400> SEQUENCE: 37

Cys Ser Val Asp Glu Arg Gly Gly Thr His Gly Tyr Thr Phe
1               5                   10

<210> SEQ ID NO 38
<211> LENGTH: 15
<212> TYPE: PRT
<213> ORGANISM: Homo sapiens

```
<400> SEQUENCE: 38

Cys Ala Ser Ser Arg Gly Leu Ala Thr Thr Asp Thr Gln Tyr Phe
1               5                   10                  15

<210> SEQ ID NO 39
<211> LENGTH: 14
<212> TYPE: PRT
<213> ORGANISM: Homo sapiens

<400> SEQUENCE: 39

Cys Ser Ala Leu Gly Gly Gly Asn Thr Gly Glu Leu Phe Phe
1               5                   10
```

METHODS OF ENRICHING CELL POPULATIONS FOR CANCER-SPECIFIC T CELLS USING IN VITRO STIMULATION OF MEMORY T CELLS

CROSS-REFERENCE TO RELATED APPLICATIONS

This patent application is the U.S. national stage of PCT/US2018/063563, filed Dec. 3, 2018, which claims the benefit of U.S. Provisional Patent Application No. 62/594,262, filed Dec. 4, 2017, which is incorporated herein by reference.

STATEMENT REGARDING FEDERALLY SPONSORED RESEARCH AND DEVELOPMENT

This invention was made with Government support under Grant Number ZIABC010985 awarded by the National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,374 Byte ASCII (Text) file named "749478_ST25.TXT" dated Jun. 1, 2020.

BACKGROUND OF THE INVENTION

Adoptive cell therapy (ACT) can produce positive clinical responses in some cancer patients. Nevertheless, obstacles to the successful use of ACT for the widespread treatment of cancer and other diseases remain. For example, T cells and TCRs that specifically recognize cancer antigens may be difficult to identify and/or isolate from a patient. Accordingly, there is a need for improved methods of obtaining cancer-reactive T cells and TCRs.

BRIEF SUMMARY OF THE INVENTION

An embodiment of the invention provides a method of obtaining a cell population enriched for T cells having antigenic specificity for a cancer-specific mutation, the method comprising: (a) obtaining monocytes from a mammal; (b) differentiating the monocytes into dendritic cells (DCs); (c) inducing the DCs to present one or more mutated amino acid sequences, each mutated amino acid sequence being encoded by a gene comprising a cancer-specific mutation; (d) obtaining a bulk population of peripheral blood mononuclear cells (PBMCs) from the mammal; (e) specifically selecting cells with a T cell phenotype from the bulk population, wherein the T cell phenotype is a memory T cell phenotype or a $T_{EMRA}$ phenotype; (f) separating the cells with the T cell phenotype selected in (e) from cells which lack the T cell phenotype; (g) stimulating the separated cells with the T cell phenotype of (f) with the dendritic cells of (c) in vitro; (h) re-stimulating the cells with the T cell phenotype of (g) with the dendritic cells of (c) in vitro; (i) specifically selecting the re-stimulated cells of (h) which express one or more markers of T cell stimulation; (j) separating the selected cells of (i) which express the one or more markers of T cell stimulation from the cells which do not express the one or more markers of T cell stimulation; (k) screening the cells of (j) which express the one or more markers of T cell stimulation for recognition of the one or more mutated amino acid sequences; and (l) selecting the cells of (k) which have antigenic specificity for the one or more mutated amino acid sequences to provide a cell population enriched for T cells having antigenic specificity for the cancer-specific mutation of (c).

Another embodiment of the invention provides a method of isolating a T cell receptor (TCR), or an antigen-binding portion thereof, having antigenic specificity for a mutated amino acid sequence encoded by a cancer-specific mutation, the method comprising: obtaining a cell population enriched for T cells having antigenic specificity for a cancer-specific mutation according to any of the inventive methods; and isolating a nucleotide sequence that encodes the TCR, or the antigen-binding portion thereof, from the cell population, wherein the TCR, or the antigen-binding portion thereof, has antigenic specificity for the mutated amino acid sequence encoded by the cancer-specific mutation.

Still another embodiment of the invention provides a method of preparing a population of cells that express a TCR, or an antigen-binding portion thereof, having antigenic specificity for a mutated amino acid sequence encoded by a cancer-specific mutation, the method comprising: isolating a TCR, or an antigen-binding portion thereof, according to any of the inventive methods; and introducing the nucleotide sequence encoding the isolated TCR, or the antigen-binding portion thereof, into peripheral blood mononuclear cells (PBMC) to obtain cells that express the TCR, or the antigen-binding portion thereof.

Additional embodiments of the invention provide related populations of cells, TCRs or antigen-binding portions thereof, pharmaceutical compositions, and methods of treating or preventing cancer.

BRIEF DESCRIPTION OF THE SEVERAL VIEWS OF THE DRAWINGS

FIG. 3B shows the percentage of naïve (black bars) or memory cells (hatched bars) expressing CD8+4-1BB+ following co-culture with target cells expressing the indicated TMG. Memory and naïve T cells cultured in the presence of phorbol myristate acetate (PMA)/ionomycin served as a positive control. Memory and naïve T cells cultured in the presence of non-relevant TMG (NR) served as a negative control.

FIG. 3C shows the percentage of memory T cells expressing CD8+4-1BB+ following co-culture with target cells expressing the indicated mutated peptide. Memory T cells cultured in the presence of PMA served as a positive control. Memory T cells cultured in the presence of DCs expressing no mutated peptide served as a negative control.

FIG. 3D shows the percentage of memory T cells expressing CD8+4-1BB+ following co-culture with target cells expressing TMG8 or the indicated mutated (MUT) or wild type (WT) SMAD5 long peptide (LP), minimal epitope (ME), or SMAD5 RNA. Memory T cells cultured in the presence of PMA served as a positive control. Memory T cells cultured in the presence of DCs expressing no mutated peptide (DC) or non-relevant (NR) RNA served as negative controls.

DETAILED DESCRIPTION OF THE INVENTION

Figure 1:
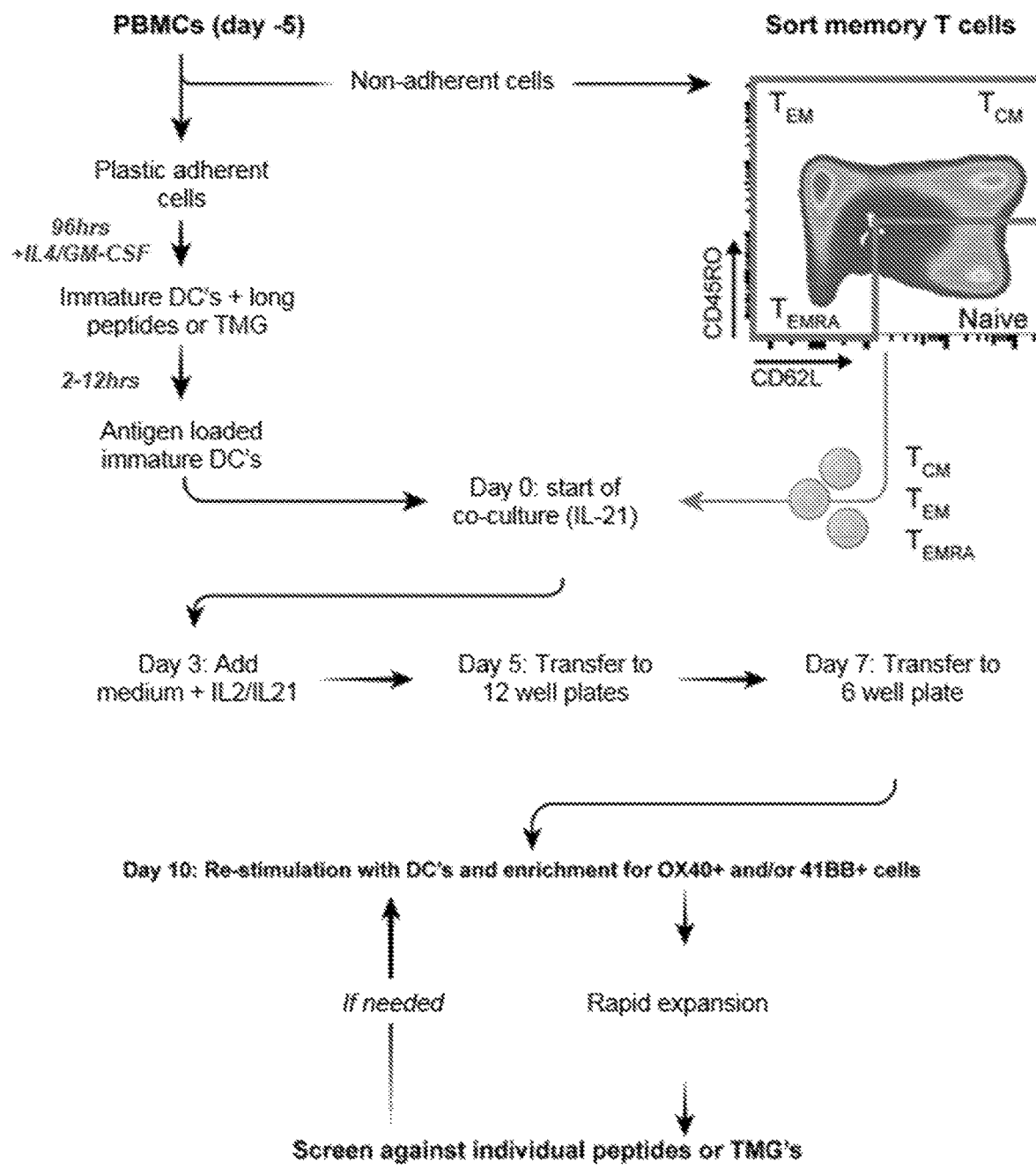
FIG. 1 is a schematic illustrating a method of obtaining a cell population enriched for T cells having antigenic specificity for a cancer-specific mutation according to an embodiment of the invention.

An embodiment of the invention provides a method of obtaining a cell population enriched for T cells having antigenic specificity for a cancer-specific mutation. The inventive methods isolate T cells having antigenic specificity for a cancer-specific mutation (e.g., a neoantigen) by carrying out in vitro stimulation (IVS) on autologous T cells with a memory T cell phenotype or a $T_{EMRA}$ phenotype.

The inventive methods provide any of a variety of advantages. Although the tumor is a natural sink for cancer mutation-specific T cells, these cells are far less frequent in peripheral blood. Peripheral blood is a more accessible and abundant source of T cells as compared to tumor. The inventive methods may advantageously isolate T cells having antigenic specificity for a cancer-specific mutation from peripheral blood.

By carrying out IVS on memory T cells or $T_{EMRA}$ cells rather on bulk peripheral blood mononuclear cells (PBMC), the inventive methods are, advantageously, capable of isolating T cells or T cell receptors (TCRs) from antigen-experienced T cell populations. Without being bound to a particular theory or mechanism, it is believed that, to acquire the memory T cell phenotype or $T_{EMRA}$ phenotype, these cells have been stimulated by their cognate antigen at the tumor site of the mammal or the tumor's draining lymph nodes. Therefore, if T cells having antigenic specificity for a cancer-specific mutation can be isolated from the limited antigen-experienced T cell repertoire, it is believed that they may be better candidates for isolating T cells or TCRs for patient treatment.

By applying IVS with autologous antigen presenting cells (APCs) and enriching for cancer-specific mutation (e.g., neoantigen)-stimulated memory T cells, the inventive methods are, advantageously, able to isolate cancer-mutation specific T cells from peripheral blood. The inventive methods may, advantageously, be applied to isolate cancer mutation-specific T cells from any cancer patient for adoptive transfer or TCR therapy.

Moreover, while other methods to isolate tumor reactive T cells with IVS use bulk PBMC containing all T cell populations, including the highly polyclonal antigen inexperienced naïve repertoire, the inventive methods advantageously focus on antigen experienced cells. By doing so, the inventive methods are capable of identifying T cells or T cell receptors against mutated amino acid sequences that can be processed and presented in vivo by APCs, which may give rise to T cells or TCRs that may be more relevant for clinical use. Moreover, cancer antigen-specific T cells may be present at a very low frequency in the peripheral blood. The inventive methods may, advantageously, isolate such low-frequency cells from the peripheral blood.

In an embodiment of the invention, the method comprises obtaining monocytes from a mammal. Monocytes may be obtained from the mammal in any suitable manner such as, for example, blood draw or leukaphresis.

The method may further comprise differentiating the monocytes into dendritic cells (DCs). The monocytes may be differentiated into DCs in any suitable manner. For example, the monocytes may be cultured with one or both of granulocyte-macrophage colony-stimulating factor (GM-CSF) and interleukin (IL)-4 until the monocytes exhibit the phenotype of an immature DC. The time period for developing the phenotype of an immature DC may vary and may be, e.g., about 72 to about 144 hours. The phenotype of an immature DC may vary among patients. CD11c is a DC marker and may be expressed in both immature and mature DC. CD80, CD86 and CD83 are co-stimulatory molecules expressed by DCs. In most cases, CD80, CD86 and CD83 are highly expressed on mature DCs and moderately expressed on immature DCs. The phenotype of an immature DC may be characterized, e.g., by the expression of any one or more toll-like receptors (TLR). Alternatively or additionally, the phenotype of an immature DC may be characterized as being (i) any one or more of CD11c$^+$, CD80$^-$, CD86$^+$, CD83$^+$, CCR7$^-$, and HLA-DR$^+$ or (ii) all of CD11c$^+$, CD80$^-$, CD86$^+$, CD83$^+$, CCR7$^-$, and HLA-DR$^+$.

In an embodiment of the invention, the method may comprise identifying one or more mutated amino acid sequences, each mutated amino acid sequence being encoded by a gene in the nucleic acid of a cancer cell of a mammal, wherein the gene comprises a cancer-specific mutation. The cancer cell may be obtained from any bodily sample derived from a mammal which contains or is expected to contain tumor or cancer cells. The bodily sample may be any tissue sample such as blood, a tissue sample obtained from the primary tumor or from tumor metastases, or any other sample containing tumor or cancer cells. The nucleic acid of the cancer cell may be DNA or RNA.

In order to identify one or more mutated amino acid sequences each encoded by a gene comprising a cancer-specific mutation, the method may further comprise sequencing nucleic acid such as DNA or RNA of normal, noncancerous cells and comparing the sequence of the cancer cell with the sequence of the normal, noncancerous cell. The normal, noncancerous cell may be obtained from the mammal or a different individual.

The cancer-specific mutation may be any mutation in any gene which encodes a mutated amino acid sequence (also referred to as a "non-silent mutation") and which is expressed in a cancer cell but not in a normal, noncancerous cell. Non-limiting examples of cancer-specific mutations that may encode mutated amino acid sequences identified in the inventive methods include missense, nonsense, insertion, deletion, duplication, frameshift, and repeat expansion mutations. In an embodiment of the invention, the method comprises identifying at least one mutated amino acid sequence encoded by a gene containing a cancer-specific mutation. However, the number of mutated amino acid sequences that may be identified is not limited and may include more than one mutated amino acid sequence (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). In an embodiment in which more than one mutated amino acid sequence is identified, the mutated amino acid sequences may be encoded by the same mutated gene or by different mutated genes.

In an embodiment, the method comprises sequencing the whole exome, the whole genome, or the whole transcriptome of the cancer cell. Sequencing may be carried out in any suitable manner known in the art. Examples of sequencing techniques that may be useful in the inventive methods include Next Generation Sequencing (NGS) (also referred to as "massively parallel sequencing technology") or Third Generation Sequencing. NGS refers to non-Sanger-based high-throughput DNA sequencing technologies. With NGS, millions or billions of DNA strands may be sequenced in parallel, yielding substantially more throughput and minimizing the need for the fragment-cloning methods that are often used in Sanger sequencing of genomes. In NGS, nucleic acid templates may be randomly read in parallel along the entire genome by breaking the entire genome into small pieces. NGS may, advantageously, provide nucleic acid sequence information of a whole genome, exome, or transcriptome in very short time periods, e.g., within about 1 to about 2 weeks, preferably within about 1 to about 7 days, or most preferably, within less than about 24 hours. Multiple NGS platforms which are commercially available or which are described in the literature can be used in the context of the inventive methods, e.g., those described in Zhang et al., *J. Genet. Genomics,* 38(3): 95-109 (2011) and Voelkerding et al., *Clinical Chemistry,* 55: 641-658 (2009).

Non-limiting examples of NGS technologies and platforms include sequencing-by-synthesis (also known as "pyrosequencing") (as implemented, e.g., using the GS-FLX 454 Genome Sequencer, 454 Life Sciences (Branford, Conn.), ILLUMINA SOLEXA Genome Analyzer (Illumina Inc., San Diego, Calif.), or the ILLUMINA HISEQ 2000 Genome Analyzer (Illumina), or as described in, e.g., Ronaghi et al., *Science,* 281(5375): 363-365 (1998)), sequencing-by-ligation (as implemented, e.g., using the SOLID platform (Life Technologies Corporation, Carlsbad, Calif.) or the POLONATOR G.007 platform (Dover Systems, Salem, N.H.)), single-molecule sequencing (as implemented, e.g., using the PACBIO RS system (Pacific Biosciences (Menlo Park, Calif.) or the HELISCOPE platform (Helicos Biosciences (Cambridge, Mass.)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, R.I.), and the ligase-based DNA sequencing platform with DNA nanoball (DNB) technology referred to as probe-anchor ligation (cPAL)), electron microscopy-based technology for single-molecule sequencing, and ion semiconductor sequencing.

The method may further comprise inducing the DCs to present the one or more mutated amino acid sequences, each mutated amino acid sequence being encoded by a gene comprising a cancer-specific mutation. The DCs may be autologous to the mammal. The DCs may present peptide fragments comprising the one or more mutated amino acid sequences in association with major histocompatibility complex (MHC) molecules on their cell surface. By using autologous DCs from the mammal, the inventive methods may, advantageously, identify T cells, or a TCR, or an antigen binding portion thereof, which recognize the one or more mutated amino acid sequences presented in the context of an MHC molecule expressed by the mammal. The MHC molecule can be any MHC molecule expressed by the mammal including, but not limited to, MHC Class I, MHC Class II, HLA-A, HLA-B, HLA-C, HLA-DM, HLA-DO, HLA-DP, HLA-DQ, and HLA-DR molecules. Accordingly, in an embodiment of the invention, the inventive methods advantageously identify mutated amino acid sequences presented in the context of any MHC molecule expressed by the mammal and are not limited to any particular MHC molecule. Preferably, the DCs are antigen-negative DCs.

Inducing DCs from the mammal to present the one or more mutated amino acid sequences may be carried out using any suitable method known in the art. In an embodiment of the invention, inducing the DCs to present the one or more mutated amino acid sequences comprises pulsing the DCs with peptides comprising the mutated amino acid sequence or a pool of peptides, each peptide in the pool comprising a different mutated amino acid sequence. Each of the mutated amino acid sequences in the pool may be encoded by a gene containing a cancer specific mutation. In this regard, the DCs may be cultured with a peptide or a pool of peptides comprising the one or more mutated amino acid sequences in a manner such that the DCs internalize the peptide(s) and display the mutated amino acid sequence(s), bound to an MHC molecule, on the cell membrane. In an embodiment in which more than one mutated amino acid sequence is identified, each mutated amino acid sequence being encoded by a gene comprising a cancer-specific mutation, the method may comprise pulsing the DCs with a pool of peptides, each peptide in the pool comprising a different mutated amino acid sequence. Methods of pulsing DCs are known in the art and are described in, e.g., Solheim (Ed.), *Antigen Processing and Presentation Protocols* (*Methods in Molecular Biology*), Human Press, (2010). The peptide(s) used to pulse the DCs may include the mutated amino acid(s) encoded by the cancer-specific mutation. The peptide(s) may further comprise any suitable number of contiguous amino acids from the endogenous protein encoded by the gene on each of the carboxyl side and the amino side of the mutated amino acid(s). The number of contiguous amino acids from the endogenous protein flanking each side of the mutation is not limited and may be, for example, about 4, about 5, about 6, about 7, about 8, about 9, about 10, about 11, about 12, about 13, about 14, about 15, about 16, about 17, about 18, about 19, about 20, or a range defined by any two of the foregoing values. Preferably, the peptide(s) comprise(s) about 12 contiguous amino acids from the endogenous protein on each side of the mutated amino acid(s). Accordingly, in an embodiment of the invention, the peptide(s) may have a length of about 15 to about 40 amino acid residues or about 20 to about 30 amino acid residues, preferably about 25 amino acid residues. In an embodiment of the invention, the peptide(s) may comprise a minimal T cell epitope comprising the mutated amino acid sequence. In this regard, the peptide(s) may have a shorter length, e.g., a length of about 8 to about 19 amino acid residues. The minimal T cell epitope may be determined by prediction in silico as described, for example, in Trolle et al., *Bioinformatics,* 31(13): 2174-81 (2015) or through experimentation.

In an embodiment of the invention, inducing the DCs from the mammal to present the one or more mutated amino acid sequence(s) comprises introducing nucleotide sequence(s) encoding the one or more mutated amino acid sequence into the DCs. The nucleotide sequence(s) is/are introduced into the DCs so that the DCs express and display the one or more mutated amino acid sequences, bound to an MHC molecule, on the cell membrane. The nucleotide sequence(s) encoding the mutated amino acid may be RNA or DNA. Introducing nucleotide sequence(s) into DCs may be carried out in any of a variety of different ways known in the art as described in, e.g., Solheim et al. supra. Non-limiting examples of techniques that are useful for introducing nucleotide sequence(s) into DCs include transformation, transduction, transfection, and electroporation. In an embodiment in which more than one mutated amino acid sequence is identified, the method may comprise preparing more than one nucleotide sequence, each encoding a mutated amino acid sequence encoded by a different gene, and introducing each nucleotide sequence into a different population of dendritic cells. In this regard, multiple populations of DCs, each population expressing and displaying a different mutated amino acid sequence, may be obtained.

In an embodiment in which more than one mutated amino acid sequence is identified, each mutated amino acid sequence being encoded by a gene comprising a cancer-specific mutation, the method may comprise introducing a nucleotide sequence encoding more than one gene, each gene having a cancer-specific mutation. In this regard, in an embodiment of the invention, the nucleotide sequence introduced into the DCs is a tandem minigene (TMG) construct, each minigene comprising a different gene, each gene including a cancer-specific mutation that encodes a mutated amino acid sequence. Each minigene may encode one mutation identified, for example, as described herein flanked on each side of the mutation by any suitable number of contiguous amino acids from the endogenous protein encoded by the gene, as described herein with respect to other aspects of the invention. The number of minigenes in the construct is not limited and may include for example, about 5, about 10, about 11, about 12, about 13, about 14, about 15, about 20, about 25, or more, or a range defined by any two of the foregoing values. The DCs express the mutated amino acid sequences encoded by the TMG construct and display the mutated amino acid sequences, bound to an MHC molecule, on the cell membranes. In an embodiment, the method may comprise preparing more than one TMG construct, each construct encoding a different set of mutated amino acid sequences encoded by different genes, and introducing each TMG construct into a different population of DCs. In this regard, multiple populations of DCs, each population expressing and displaying mutated amino acid sequences encoded by different TMG constructs, may be obtained.

The method may further comprise obtaining a bulk population of peripheral blood mononuclear cells (PBMCs) from the mammal. The method may comprise obtaining a bulk population of PBMCs from a sample of peripheral blood by any suitable method known in the art. Suitable methods of obtaining a bulk population of PBMCs may include, but are not limited to, a blood draw and/or a leukapheresis.

The method may comprise specifically selecting cells with a T cell phenotype from the bulk population, wherein the T cell phenotype is a memory T cell phenotype or an effector memory RA ($T_{EMRA}$) phenotype. Memory T cells and $T_{EMRA}$ cells have previously encountered and responded to their cognate antigen. The method may comprise specifically selecting the cells in any suitable manner. Examples of techniques for selecting cells may include fluorescence-activated cell sorting (FACS) or magnetic-activated cell sorting (MACS) as described in, e.g., Turcotte et al., *Clin. Cancer Res.,* 20(2): 331-43 (2013) and Gros et al., *J. Clin. Invest.,* 124(5): 2246-59 (2014). The technique for selecting cells may employ any antibodies and stains suitable for selecting cells with the desired phenotype. With respect to the cell markers of the phenotypes discussed herein, the "+" or "+" symbol immediately following a cell marker indicates that the cell under discussion expresses the indicated cell marker. The "−" or "−" symbol immediately following a cell marker indicates that the cell under discussion does not express the indicated cell marker.

A $T_{EMRA}$ phenotype may comprise one or both of the following: $CD45RO^-$, $CD62L^-$, $CD45RA^+$, and $CCR7^-$. In an embodiment of the invention, the $T_{EMRA}$ phenotype further comprises one or more of the following: $CD3^+$, $CD4^+$, and $CD8^+$. In a preferred embodiment, the $T_{EMRA}$ phenotype comprises (i) all of $CD3^+$, $CD45RO^-$, $CD62L^-$, $CD45RA^+$, and $CCR7^-$ and (ii) one or both of $CD4^+$ and $CD8^+$.

A memory T cell phenotype may comprise one or both of the following: CD45RO+ and CD45RA−. In an embodiment of the invention, the memory T cell phenotype further comprises one or more of the following: CD3+, CD4+, and CD8+. In a preferred embodiment, the memory T cell phenotype comprises (i) all of CD3+, CD45RO+, and CD45RA− and (ii) one or both of CD4+ and CD8+.

In an embodiment of the invention, the memory T cell phenotype may be a central memory T cell ($T_{CM}$) phenotype. A $T_{CM}$ phenotype may comprise any one or more of (and preferably all of): CCR7+, CD62L+, CD27+, CD28+, CD45RO+, CD122+, and CD45RA−. $T_{CM}$ cells express any one or more of (and preferably all of) the following transcription factors: TCF7, ID3, LEF1, FOXP1, KLF7, EOMES, ID2, PRDM1, TBX21, and ZEB2.

In an embodiment of the invention, the memory T cell phenotype may be an effector memory T cell ($T_{EM}$) phenotype. A $T_{EM}$ phenotype may comprise any one or more of (and preferably all of): CCR7−, CD62L−, CD45RO+, CD122+, and CD45RA−. $T_{EM}$ cells express any one or more of (and preferably all of) the following transcription factors: TCF7, ID3, EOMES, ID2, PRDM1, TBX21, and ZEB2.

In an embodiment of the invention, the T cell phenotype specifically selected from the bulk population is not a naïve T cell ($T_N$) phenotype. Unlike memory T cells and $T_{EMRA}$ cells, $T_N$ cells have not encountered their cognate antigen. A $T_N$ phenotype comprises all of CD45RA+, CD62L+, CCR7+, CD27+, CD28+, CD45RO−, CD122−, and CD95−.

The method may further comprise separating the selected cells with the T cell phenotype from cells which lack the T cell phenotype, wherein the T cell phenotype is a memory T cell phenotype or a $T_{EMRA}$ phenotype. In this regard, the selected cells may be physically separated from the unselected cells. The selected cells may be separated from unselected cells by any suitable method such as, for example, sorting by FACS or MACS, as described herein with respect to other aspects of the invention.

The method may further comprise stimulating, in vitro, the separated cells with the selected T cell phenotype with the DCs which have been induced to present the one or more mutated amino acid sequence. The stimulating may be carried out in any manner suitable to achieve recognition of the mutated amino acid sequence by the cells with the selected T cell phenotype. For example, the method may comprise co-culturing the DCs with the cells having the selected T cell phenotype. The method may further comprise re-stimulating the cells having the selected T cell phenotype with the DCs in vitro in the same or a similar manner. In an embodiment of the invention, the re-stimulating occurs about 11 to about 16 days after the first stimulation.

The method may further comprise specifically selecting the re-stimulated cells which express one or more markers of T cell stimulation. For example, upon co-culture of the cells with the selected T cell phenotype with the DCs that present the mutated amino acid sequence, T cells having antigenic specificity for the mutated amino acid sequence may express any one or more of a variety of T cell activation markers which may be used to identify those T cells having antigenic specificity for the mutated amino acid sequence. Such T cell activation markers may include, but are not limited to, programmed cell death 1 (PD-1), lymphocyte-activation gene 3 (LAG-3), T cell immunoglobulin and mucin domain 3 (TIM-3), 4-1BB, OX40, and CD107a. Accordingly, in an embodiment of the invention, specifically selecting the re-stimulated cells comprises selecting the T cells that express any one or more of PD-1, LAG-3, TIM-3, 4-1BB, OX40, and CD107a.

In an embodiment of the invention, the method further comprises expanding the number of cells which express the one or more markers of T cell stimulation. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in U.S. Pat. No. 8,034,334 and U.S. Patent Application Publication No. 2012/0244133, each of which is incorporated herein by reference.

The method may further comprise separating the cells which express the one or more markers of T cell stimulation from the cells which do not express the one or more markers of T cell stimulation. Cells expressing one or more T cell activation markers may be sorted on the basis of expression of the marker using any of a variety of techniques known in the art such as, for example, fluorescence-activated cell sorting (FACS) or magnetic-activated cell sorting (MACS) as described in, e.g., Turcotte et al., *Clin. Cancer Res.*, 20(2): 331-43 (2013) and Gros et al., *J. Clin. Invest.*, 124(5): 2246-59 (2014). In this regard, the selected cells may be physically separated from the unselected cells.

The method may further comprise screening the cells which express the one or more markers of T cell stimulation for recognition of the one or more mutated amino acid sequences. In an embodiment of the invention, the screening occurs about 11 to about 16 days after the separating of the cells which express the one or more markers of T cell stimulation from the cells which do not express the one or more markers of T cell stimulation. The screening of the cells for recognition of the one or more mutated amino acid sequences may be carried out in any suitable manner. For example, the cells which express the one or more markers of T cell stimulation may be co-cultured with target cells which express the one or more mutated amino acid sequences. The target cells may be, for example, autologous DCs which have been induced to express the one or more mutated amino acid sequences as described herein with respect to other aspects of the invention. The method may optionally further comprise re-stimulating the cells with the DCs after screening, if needed.

The method may further comprise selecting the cells which have antigenic specificity for the one or more mutated amino acid sequences to provide a cell population enriched for T cells having antigenic specificity for a cancer-specific mutation. Selecting the cells which have antigenic specificity for the one or more mutated amino acid sequences may be carried out in any suitable manner. For example, the cells having antigenic specificity for the mutated amino acid sequence may be selected on the basis of the expression of any one or more of a variety of T cell activation markers, as described herein with respect to other aspects of the invention. The numbers of selected cells having antigenic specificity for the mutated amino acid sequence may be expanded as described herein with respect to other aspects of the invention.

In another embodiment of the invention, selecting the T cells that have antigenic specificity for the mutated amino acid sequence comprises selecting the T cells (i) that secrete a greater amount of one or more cytokines upon co-culture with DCs that present the mutated amino acid sequence as compared to the amount of the one or more cytokines secreted by a negative control or (ii) in which at least twice as many of the numbers of T cells secrete one or more cytokines upon co-culture with DCs that present the mutated amino acid sequence as compared to the numbers of negative control T cells that secrete the one or more cytokines. The one or more cytokines may comprise any cytokine the secretion of which by a T cell is characteristic of T cell activation (e.g., a T cell receptor (TCR) expressed by the T cells specifically binding to and immunologically recognizing the mutated amino acid sequence). Non-limiting examples of cytokines, the secretion of which is characteristic of T cell activation, include IFN-γ, IL-2, and tumor necrosis factor alpha (TNF-α), granulocyte/monocyte colony stimulating factor (GM-CSF), IL-4, IL-5, IL-9, IL-10, IL-17, and IL-22.

For example, the T cells may be considered to have "antigenic specificity" for the mutated amino acid sequence if the T cells secrete at least twice as much IFN-γ upon co-culture with (a) antigen-negative DCs pulsed with a concentration of a peptide comprising the mutated amino acid sequence (e.g., about 0.05 ng/mL to about 10 μg/mL, e.g., 0.05 ng/mL, 0.1 ng/mL, 0.5 ng/mL, 1 ng/mL, 5 ng/mL, 100 ng/mL, 1 μg/mL, 5 μg/mL, or 10 μg/mL) or (b) DCs into which a nucleotide sequence encoding the mutated amino acid sequence has been introduced as compared to the amount of IFN-γ secreted by a negative control. The negative control may be, for example, autologous T cells (e.g., derived from peripheral blood mononuclear cells (PBMC)) co-cultured with (a) antigen-negative DCs pulsed with the same concentration of an irrelevant peptide (e.g., the wild-type amino acid sequence, or some other peptide with a different sequence from the mutated amino acid sequence) or (b) DCs into which a nucleotide sequence encoding an irrelevant peptide sequence has been introduced. The T cells may also have "antigenic specificity" for the mutated amino acid sequence if the T cells secrete a greater amount of IFN-γ upon co-culture with antigen-negative DCs pulsed with higher concentrations of a peptide comprising the mutated amino acid sequence as compared to a negative control, for example, the negative control described above. IFN-γ secretion may be measured by methods known in the art such as, for example, enzyme-linked immunosorbent assay (ELISA).

Alternatively or additionally, the T cells may be considered to have "antigenic specificity" for the mutated amino acid sequence if at least twice as many of the numbers of T cells secrete IFN-γ upon co-culture with (a) antigen-negative DCs pulsed with a concentration of a peptide comprising the mutated amino acid sequence or (b) DCs into which a nucleotide sequence encoding the mutated amino acid sequence has been introduced as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

While T cells having antigenic specificity for the mutated amino acid sequence may both (1) express any one or more T cells activation markers described herein and (2) secrete a greater amount of one or more cytokines as described herein, in an embodiment of the invention, T cells having antigenic specificity for the mutated amino acid sequence may express any one or more T cell activation markers without secreting a greater amount of one or more cytokines or may secrete a greater amount of one or more cytokines without expressing any one or more T cell activation markers.

Another embodiment of the invention provides a method of isolating a T cell receptor (TCR), or an antigen-binding portion thereof, having antigenic specificity for a mutated amino acid sequence encoded by a cancer-specific mutation. The method may comprise obtaining a cell population enriched for T cells having antigenic specificity for a cancer-specific mutation according to any of the methods described herein with respect to other aspects of the invention.

The method may further comprise isolating a nucleotide sequence that encodes the TCR, or the antigen-binding portion thereof, from the cell population, wherein the TCR, or the antigen-binding portion thereof, has antigenic specificity for the mutated amino acid sequence encoded by the cancer-specific mutation. In an embodiment of the invention, prior to isolating the nucleotide sequence that encodes the TCR, or the antigen-binding portion thereof, the numbers cells in the population may be expanded as described herein with respect to other aspects of the invention. In another embodiment of the invention, the numbers of cells in the population are not expanded prior to isolating the nucleotide sequence that encodes the TCR, or the antigen-binding portion thereof.

The "the antigen-binding portion" of the TCR, as used herein, refers to any portion comprising contiguous amino acids of the TCR of which it is a part, provided that the antigen-binding portion specifically binds to the mutated amino acid sequence encoded by the gene identified as described herein with respect to other aspects of the invention. The term "antigen-binding portion" refers to any part or fragment of the TCR of the invention, which part or fragment retains the biological activity of the TCR of which it is a part (the parent TCR). Antigen-binding portions encompass, for example, those parts of a TCR that retain the ability to specifically bind to the mutated amino acid sequence, or detect, treat, or prevent cancer, to a similar extent, the same extent, or to a higher extent, as compared to the parent TCR. In reference to the parent TCR, the functional portion can comprise, for instance, about 10%, about 25%, about 30%, about 50%, about 68%, about 80%, about 90%, about 95%, or more, of the parent TCR.

The antigen-binding portion can comprise an antigen-binding portion of either or both of the α and β chains of the TCR of the invention, such as a portion comprising one or more of the complementarity determining region (CDR)1, CDR2, and CDR3 of the variable region(s) of the α chain and/or β chain of the TCR of the invention. In an embodiment of the invention, the antigen-binding portion can comprise the amino acid sequence of the CDR1 of the α chain (CDR1a), the CDR2 of the α chain (CDR2a), the CDR3 of the α chain (CDR3α), the CDR1 of the β chain (CDR1β), the CDR2 of the β chain (CDR2β), the CDR3 of the β chain (CDR3β), or any combination thereof. Preferably, the antigen-binding portion comprises the amino acid sequences of CDR1α, CDR2α, and CDR3α; the amino acid sequences of CDR1β, CDR2β, and CDR3β; or the amino acid sequences of all of CDR1α, CDR2α, CDR3α, CDR1β, CDR2β, and CDR3β of the inventive TCR.

In an embodiment of the invention, the antigen-binding portion can comprise, for instance, the variable region of the inventive TCR comprising a combination of the CDR regions set forth above. In this regard, the antigen-binding portion can comprise the amino acid sequence of the variable region of the α chain (Vα), the amino acid sequence of the variable region of the β chain (Vβ), or the amino acid sequences of both of the Vα and Vβ of the inventive TCR.

In an embodiment of the invention, the antigen-binding portion may comprise a combination of a variable region and a constant region. In this regard, the antigen-binding portion can comprise the entire length of the α or β chain, or both of the α and β chains, of the inventive TCR.

Isolating the nucleotide sequence that encodes the TCR, or the antigen-binding portion thereof, from the selected autologous T cells may be carried out in any suitable manner known in the art. For example, the method may comprise isolating RNA from the autologous T cells and sequencing the TCR, or the antigen-binding portion thereof, using established molecular cloning techniques and reagents such as, for example, 5' Rapid Amplification of cDNA Ends (RACE) polymerase chain reaction (PCR) using TCR-α and -β chain constant primers.

In an embodiment of the invention, the method may comprise cloning the nucleotide sequence that encodes the TCR, or the antigen-binding portion thereof, into a recombinant expression vector using established molecular cloning techniques as described in, e.g., Green et al. (Eds.), *Molecular Cloning: A Laboratory Manual*, Cold Spring Harbor Laboratory Press; 4th Ed. (2012). For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of transposon/transposase, the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The TCR, or the antigen-binding portion thereof, isolated by the inventive methods may be useful for preparing cells for adoptive cell therapies. In this regard, an embodiment of the invention provides a method of preparing a population of cells that express a TCR, or an antigen-binding portion thereof, having antigenic specificity for a mutated amino acid sequence encoded by a cancer-specific mutation, the method comprising isolating a TCR, or an antigen-binding portion thereof, as described herein with respect to other aspects of the invention, and introducing the nucleotide sequence encoding the isolated TCR, or the antigen-binding portion thereof, into PBMC to obtain cells that express the TCR, or the antigen-binding portion thereof.

Introducing the nucleotide sequence (e.g., a recombinant expression vector) encoding the isolated TCR, or the antigen-binding portion thereof, into PBMC may be carried out in any of a variety of different ways known in the art as described in, e.g., Green et al. supra. Non-limiting examples of techniques that are useful for introducing a nucleotide sequence into PBMC include transformation, transduction, transfection, and electroporation.

In an embodiment of the invention, the method comprises introducing the nucleotide sequence encoding the isolated TCR, or the antigen-binding portion thereof, into PBMC that are autologous to the mammal. In this regard, the TCRs, or the antigen-binding portions thereof, identified and isolated by the inventive methods may be personalized to each mammal. However, in another embodiment, the inventive methods may identify and isolate TCRs, or the antigen-binding portions thereof, that have antigenic specificity against a mutated amino acid sequence that is encoded by a recurrent (also referred to as "hot-spot") cancer-specific mutation. In this regard, the method may comprise introducing the nucleotide sequence encoding the isolated TCR, or the antigen-binding portion thereof, into PBMC that are allogeneic to the mammal. For example, the method may comprise introducing the nucleotide sequence encoding the isolated TCR, or the antigen-binding portion thereof, into the PBMC of another mammal whose tumors express the same mutation in the context of the same MHC molecule.

In an embodiment of the invention, the PBMC include T cells. Without being bound to a particular theory or mechanism, it is believed that less differentiated, "younger" T cells may be associated with any one or more of greater in vivo persistence, proliferation, and antitumor activity as compared to more differentiated, "older" T cells. Accordingly, the inventive methods may, advantageously, identify and isolate a TCR, or an antigen-binding portion thereof, that has antigenic specificity for the mutated amino acid sequence and introduce the TCR, or an antigen-binding portion thereof, into "younger" T cells that may provide any one or more of greater in vivo persistence, proliferation, and antitumor activity as compared to "older" T cells (e.g., effector cells in a patient's tumor) from which the TCR, or the antigen-binding portion thereof, may have been isolated.

In an embodiment of the invention, the method further comprises expanding the numbers of PBMC that express the TCR, or the antigen-binding portion thereof. The numbers of PBMC may be expanded, for example, as described herein with respect to other aspects of the invention. In this regard, the inventive methods may, advantageously, generate a large number of T cells having antigenic specificity for the mutated amino acid sequence.

Another embodiment of the invention provides a TCR, or an antigen-binding portion thereof, isolated by any of the methods described herein with respect to other aspects of the invention. An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. Another embodiment of the invention provides an antigen-binding portion of the TCR comprising one or more CDR regions, one or more variable regions, or one or both of the α and β chains of the TCR, as described herein with respect to other aspects of the invention. The polypeptides of the inventive TCR, or the antigen-binding portion thereof, can comprise any amino acid sequence, provided that the TCR, or the antigen-binding portion thereof, has antigenic specificity for the mutated amino acid sequence encoded by the cancer-specific mutation.

Another embodiment of the invention provides an isolated population of cells prepared according to any of the methods described herein with respect to other aspects of the invention. The population of cells can be a heterogeneous population comprising the PBMC expressing the isolated TCR, or the antigen-binding portion thereof, in addition to at least one other cell, e.g., a host cell (e.g., a PBMC), which does not express the isolated TCR, or the antigen-binding portion thereof, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of PBMC (e.g., consisting essentially of) expressing the isolated TCR, or the antigen-binding portion thereof. The population also can be a clonal population of cells, in which all cells of the population are clones of a single PBMC expressing the isolated TCR, or the antigen-binding portion thereof, such that all cells of the population express the isolated TCR, or the antigen-binding portion thereof. In one embodiment of the invention, the population of cells is a clonal population comprising PBMC expressing the isolated TCR, or the antigen-binding portion thereof, as described herein. By introducing the nucleotide sequence encoding the isolated TCR, or the antigen binding portion thereof, into PBMC, the inventive methods may, advantageously, provide a population of cells that comprises a high proportion of PBMC cells that express the isolated TCR and have antigenic specificity for the mutated amino acid sequence. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises PBMC cells that express the isolated TCR and have antigenic specificity for the mutated amino acid sequence. Without being bound to a particular theory or mechanism, it is believed that populations of cells that comprise a high proportion of PBMC cells that express the isolated TCR and have antigenic specificity for the mutated amino acid sequence have a lower proportion of irrelevant cells that may hinder the function of the PBMC, e.g., the ability of the PBMC to target the destruction of cancer cells and/or treat or prevent cancer.

The inventive TCRs, or the antigen-binding portions thereof, and populations of cells can be formulated into a composition, such as a pharmaceutical composition. In this regard, the invention provides a pharmaceutical composition comprising any of the inventive TCRs, or the antigen-binding portions thereof, or populations of cells and a pharmaceutically acceptable carrier. The inventive pharmaceutical composition can comprise an inventive TCR, or an antigen-binding portion thereof, or population of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR, or the antigen-binding portion thereof, or population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR, the antigen-binding portion thereof, or population of cells, as well as by the particular method used to administer the inventive TCR, the antigen-binding portion thereof, or population of cells. Accordingly, there are a variety of suitable formulations of the pharmaceutical composition of the invention. Suitable formulations may include any of those for oral, parenteral, subcutaneous, intravenous, intramuscular, intratumoral, intraarterial, intrathecal, or interperitoneal administration. More than one route can be used to administer the inventive TCR or population of cells, and in certain instances, a particular route can provide a more immediate and more effective response than another route.

Preferably, the inventive TCR, the antigen-binding portion thereof, or population of cells is administered by injection, e.g., intravenously. When the inventive population of cells is to be administered, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

It is contemplated that the inventive TCRs, the antigen-binding portions thereof, populations of cells, and pharmaceutical compositions can be used in methods of treating or preventing cancer. Without being bound to a particular theory or mechanism, the inventive TCRs, or the antigen-binding portions thereof, are believed to bind specifically to a mutated amino acid sequence encoded by a cancer-specific mutation, such that the TCR, or the antigen-binding portion thereof, when expressed by a cell, is able to mediate an immune response against a target cell expressing the mutated amino acid sequence. In this regard, the invention provides a method of treating or preventing cancer in a mammal, comprising administering to the mammal any of the pharmaceutical compositions, TCRs, antigen-binding portions thereof, or populations of cells described herein, in an amount effective to treat or prevent cancer in the mammal. In an embodiment of the invention, the method comprises obtaining a population of cells according to any of methods described herein and administering the population of cells to the mammal in an amount effective to treat or prevent cancer in the mammal. Another embodiment of the invention provides the population of cells obtained according to any of the methods described herein for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof, or preventing the recurrence of the cancer.

For purposes of the invention, the amount or dose of the inventive TCR, the antigen-binding portion thereof, population of cells, or pharmaceutical composition administered (e.g., numbers of cells when the inventive population of cells is administered) should be sufficient to effect, e.g., a therapeutic or prophylactic response, in the mammal over a reasonable time frame. For example, the dose of the inventive TCR, the antigen-binding portion thereof, population of cells, or pharmaceutical composition should be sufficient to bind to a mutated amino acid sequence encoded by a cancer-specific mutation, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR, the antigen-binding portion thereof, population of cells, or pharmaceutical composition administered and the condition of the mammal (e.g., human), as well as the body weight of the mammal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, or the antigen-binding portion thereof, upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR, the antigen-binding portion thereof, population of cells, or pharmaceutical composition also will be determined by the existence, nature and extent of any adverse side effects that might accompany the administration of a particular inventive TCR, the antigen-binding portion thereof, population of cells, or pharmaceutical composition. Typically, the attending physician will decide the dosage of the inventive TCR, the antigen-binding portion thereof, population of cells, or pharmaceutical composition with which to treat each individual patient, taking into consideration a variety of factors, such as age, body weight, general health, diet, sex, inventive TCR, the antigen-binding portion thereof, population of cells, or pharmaceutical composition to be administered, route of administration, and the severity of the condition being treated.

In an embodiment in which the inventive population of cells is to be administered, the number of cells administered per infusion may vary, for example, in the range of one million to 100 billion cells; however, amounts below or above this exemplary range are within the scope of the invention. For example, the daily dose of inventive host cells can be about 1 million to about 150 billion cells (e.g., about 5 million cells, about 25 million cells, about 500 million cells, about 1 billion cells, about 5 billion cells, about 20 billion cells, about 30 billion cells, about 40 billion cells, about 60 billion cells, about 80 billion cells, about 100 billion cells, about 120 billion cells, about 130 billion cells, about 150 billion cells, or a range defined by any two of the foregoing values), preferably about 10 million to about 130 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, about 100 billion cells, about 110 billion cells, about 120 billion cells, about 130 billion cells, or a range defined by any two of the foregoing values), more preferably about 100 million cells to about 130 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, about 50 billion cells, about 75 billion cells, about 90 billion cells, about 100 billion cells, about 110 billion cells, about 120 billion cells, about 130 billion cells, or a range defined by any two of the foregoing values).

For purposes of the inventive methods, wherein populations of cells are administered, the cells can be cells that are allogeneic or autologous to the mammal. Preferably, the cells are autologous to the mammal.

The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. Preferably, the cancer is an epithelial cancer. In an embodiment, the cancer is cholangiocarcinoma, melanoma, colon cancer, or rectal cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). Preferably, the mammals are from the order Artiodactyla, including Bovines (cows) and Swines (pigs) or of the order Perssodactyla, including Equines (horses). Preferably, the mammals are of the order Primates, Ceboids, or Simoids (monkeys) or of the order Anthropoids (humans and apes). A more preferred mammal is the human. In an especially preferred embodiment, the mammal is the patient expressing the cancer-specific mutation.

The following examples further illustrate the invention but, of course, should not be construed as in any way limiting its scope.

EXAMPLE 1

This example demonstrates a method of obtaining a cell population enriched for T cells having antigenic specificity for a cancer-specific mutation.

The following materials and methods were employed in the experiments described in Example 1.

Reagents:
(a) Peripheral blood leukocytes.
(b) Dendritic cell medium: (RPMI 1640 Media supplemented with 2 mM L-glutamine, 10 mM Hepes buffer, 1× non-essential amino acids, 25 μg/ml gentamicin, and 1% human AB sera).
(c) CTL cell medium: (50/50 RPMI and AIM-V mediums supplemented with 10 mM Hepes buffer, 25 ug/ml gentamicin, and 10% human AB sera).
(d) Dulbecco's phosphate buffered saline (PBS).
(e) Recombinant human IL-4 (Peprotech, Rocky Hill, N.J.).
(f) Recombinant human GM-CSF (Peprotech).
(g) Recombinant Human IFN-γ (Peprotech, cat. no. 300-02).
(h) Recombinant Human IL-7 (Peprotech).
(i) Recombinant Human IL-15 (Peprotech).
(j) Recombinant Human IL-21 (Peprotech).

Antibodies and staining reagents:
(a) Pe-Cy7 Anti-human CD8.
(b) allophycocyanin (APC) mouse anti human CD45RO.
(c) Phycoerythrin (PE) mouse anti human CD62L.
(d) Percp-cy5.5 mouse anti human CD45RA.
(e) APC-H7 Anti-human CD3.
(f) fluorescein isothiocyanate (FITC) mouse anti human CCR7.
(g) APC Mouse anti human 41BB.
(h) FITC mouse anti human OX40.
(i) PE mouse anti human CD4.

Plasticware:
(a) Plate, 48 wells, sterile (Greiner Bio-One (GBO) (Kremsmuenster, Austria), cat. no. 677180).
(b) Plate, 12 wells, sterile (GBO, cat. no. 655180).
(c) Plate, six wells, sterile (GBO, cat. no. 657160).

Procedure:

Schematics illustrating the procedures described below are provided in FIGS. 1 and 2.

Generation of Monocyte-Derived DCs (Recommended to Start 4-5 Days Before IVS 1):

1. Determine the number of PBMC necessary to generate mDC. Each T175 EASYFLASK flask (Thermo Fischer Scientific, Waltham, Mass.) is seeded with $1.75$-$2 \times 10^8$ PBMC cells. The expected yield is 5% if starting with fresh PBMC and 0.5-1% if starting with frozen PBMC.
2. Freshly isolated PBMC cells should be placed directly in DC media.
3. If frozen, transfer quick-thawed cells to a 50 ml conical tube containing 25 ml DC media [37° C. warm]. Centrifuge at 1,500 revolutions per minute (rpm) at room temperature (temp) for 5 minutes (min).
4. Resuspend the cell pellet in 50 ml DC media [37° C. warm]. Mix the cell suspension and perform cell count and viability by trypan blue exclusion.
5. Centrifuge at 1,500 rpm at room temp for 5 min.
6. Resuspend the cells at a final concentration $5 \times 10^6$/ml in DC media [37° C. warm]. Transfer 40 ml of cell suspension into a T175 EASYFLASK flask. Place the flask in a humidified 37° C., 5% $CO_2$ incubator for 2 hours to generate the adherent population.
7. After the incubation period is complete, aspirate the media from the flask, removing the non-adherent cells (Freeze non-adherent cells for future experiments).
8. Add 25 ml PBS and gently rock the flask 2-3 times. Aspirate to remove non-adherent cells.
9. Add complete 30 ml DC media with cytokines (granulocyte-macrophage colony-stimulating factor (GM-CSF), 100 ng/ml; IL-4, 20 ng/ml) to each flask and incubate in a $CO_2$ incubator.
10. On day 3, add 10 ml fresh DC media with cytokines (GM-CSF, 100 ng/ml; IL-4, 20 ng/ml) to each flask.
11. On day 4 or 5, harvest the cells by washing once with 25 ml PBS and incubate for 10-15 minutes in 25 ml 0.9 mM ethylenediaminetetraacetic acid (EDTA)-PBS.
12. Wash DCs with DC medium and re-suspend at 2-3e6/ml or any other chosen concentration.
13. Plate DCs into low attachment 12 or 6 well plates for peptide loading.
14. For peptide loading: load DCs with 10-15 μg/μl peptide or peptide pools for 2-12 hrs.
15. Add Toll-like receptor (TLR)mix (PolyI:C 5 μg/ml, R848 5 μg/ml and IFN-γ 100 IU/ml) to mature DCs and incubate for 10-12 hrs. Maturation of DCs is recommended for IVS of naïve cells. If using memory or $T_{EMRA}$, immature DCs are believed to be better.
16. Harvest mature DCs by washing once with 5 ml PBS and incubate for 5 minutes in 5 ml 0.9 mM EDTA-PBS.
17. Wash DCs with DC medium.
18. Resuspend DCs in cytotoxic T lymphocyte (CTL) medium and keep on ice.
19. Irradiate DCs with 30 Gy (Ensure that the cells are kept cool during transport to the radiation source). Irradiation is not needed if the DC culture is free of lymphocyte and NK (natural killer) cell contamination.
20. Resuspend DCs at concentration of 5e5/ml. Cells are ready for $1^{st}$ stimulation.

Sorting for T cell populations:

21. Thaw 1-2 vials of pheresis (3e8 PBMC each).
22. Count cells and use to start growing DCs. After the first 2 hours (hrs) (monocyte adherent stage), collect cells in suspension, wash with CTL medium and re-suspend in CTL medium without cytokines (5e6
23. Incubate cells overnight to allow upregulation of CD62L.
24. Harvest cells, count and wash twice with cold sorting buffer (PBS−/−, 1% FCS, 0.5 mM EDTA).
25. Resuspend cells in sorting buffer at 1e6/100 μl and stain with the following antibodies (or any other combination used to differentiate T cell subpopulations):
    (a) Anti-human CD8,
    (b) Anti human CD45RO,
    (c) Anti human CD62L,
    (d) Anti human CD4,
    (e) Anti-human CD3,
    (f) Anti human CD45RA,
    (g) Anti human CCR7.
26. Wash cells with sorting buffer and resuspend at 4e7/ml for sorting.
27. Sort cells according to the needs of the experiment:
    (a) Memory: $CD3^+CD4^+/CD8^+CD45RO^+CD45RA^-$,
    (b) $T_{EMRA}$: $CD3+CD4+/CD8^+CD45RO^-CD62L^-CD45RA^+CCR7^-$, or
    (c) Naïve: $CD3+CD4+/CD8^+CD45RO^-CD62L^+CD45RA^+CCR7^+$.

If needed, $T_{EM}$ and $T_{CM}$ can be isolated using CD62L and CCR7. If possible, it is recommended to sort CD4$^+$ and CD8$^+$ into different tubes to simplify the downstream IVS and screening procedures.
28. After sorting, resuspend the cells in CTL medium at a concentration of 5e5 cells per ml and use for the first IVS (IVS 1) (Item 29 under "IVS 1 set-up"). Note that peptide or TMG-loaded irradiated DCs should be ready at that stage for the IVS.

IVS 1 set-up:

29. Collect the T cells from sorted populations, count and spin.
30. Resuspend T cells in CTL medium at a concentration of 2e6/ml.
31. Add IL-21, 60 ng/ml, to the T cell fraction. (This will result in a final concentration of 30 ng/ml after the addition of the DCs).
32. Mix the DCs with T cells at a 1:1 (vol/vol) ratio (resulting in a 4:1 T cell:DC ratio, 1e$^6$ T cells/2.5e$^5$ DCs), calculate for at least 3-5 wells per group (T cell subset). It is recommended to mix the cells for each group first in one larger tube. It is not recommended to add T cells and DCs separately to the individual wells, as variation owing to pipetting errors may increase. In some cases, especially in epithelial cancer patients, it is possible to have groups including a single well (due to low number of naïve or $T_{EMRA}$ cells).
33. Transfer 500 µl of the cell mix into individual wells of a 48-well plate.
34. Incubate at 37° C. for 72 hours.
35. First feeding: Check cells under the microscope and calculate the required amount of medium to give 0.5 ml per well.
36. Make up warm CTL medium containing a 5 ng/ml concentration each of IL-15 and IL-7 (referring to the final concentration in the culture medium).
37. Add 500 µl of this cytokine-supplemented medium to each well and incubate at 37° C. for 72 h. If working just with memory or $T_{EMRA}$ cells, the feedings can be done with IL-21 and IL-2 instead of IL-7 and IL-15.
38. Second feeding: Calculate the required amount of medium to give 1 ml per well.
39. Make up warm CTL medium containing 5 ng/ml concentration each of IL-15 and IL-7 (referring to the final concentration in the culture medium).
40. Add 1 ml of this cytokine-supplemented medium to each well of a 12-well plate.
41. Transfer the cells and medium from each well of the old plate (from 31 under "IVS 1 set-up") to the new 12-well plate (Transfer of cells allows more room for expansion, but also should reduce the number of residual (plastic-adherent) myeloid cells from the DC preparation, which are no longer required).
42. Incubate the cells for 48 h.
43. Third feeding: Calculate the required amount of medium to give 2 ml per well.
44. Make up warm CTL medium containing 10 ng/ml concentration each of IL-15 and IL-7 (referring to the final concentration in the culture medium). Note that now the cytokine concentration is doubled.
45. Add 2 ml of this cytokine-supplemented, freshly prepared medium to each well of a six-well plate.
46. Transfer the cells and medium from each individual well of the 12-well plate (from Item 36 under "IVS 1 set-up") to individual wells of the new 6-well plate. Incubate for 72 h.
47. From this stage, cells can be kept in CTL medium containing 3000 IU/ml IL-2 and expanded until the second IVS and 4-1BB/OX40 enrichment. The 2nd IVS and sorting should be done 11-16 days after the 1st IVS (to allow downregulation of 4-1BB).

IVS 2+41BB/OX40 enrichment setup:

48. Thaw immature DCs, re-suspend in DC medium+cytokines and transfer into low-attachment 12 or 6 well plates for peptide loading.
49. For peptide loading: load DCs with 10-15 µg/µl peptide or peptide pools for 2-12 hrs.
50. Wash peptides and mix at 1:4 ratio (DC:T) with the appropriate T cell population (usually 4-8e6 T cells should be use for each stimulation).
51. Plate cells into 12 or 6 well plates in 3 ml CTL medium and incubate for 18-24 hrs. If possible, include dimethyl sulfoxide (DMSO) control for setting sorting parameters.
52. Harvest cells, wash with sorting buffer (PBS, 1% fetal calf serum (FCS), 0.5 mM EDTA) and stain with the following antibodies:
    (a) Pe-Cy7 mouse anti-human CD8-,
    (b) APC-H7 anti-human CD3,
    (c) APC mouse anti human 4-1BB,
    (d) FITC mouse anti human OX40, and
    (e) PE mouse anti human CD4.
    Wash samples using sorting buffer and sort the CD3+CD4+41BB+OX40+/CD3+CD8+41BB+OX40+ cells (both double and single positive cells). It is recommended to sort CD4$^+$ and CD8$^+$ into different tubes to simplify the downstream screening procedures.
53. After sorting, keep cells in CTL medium supplemented with 3000 IU/ml IL-2. (if cell number is lower than 1e5, expand the number of cells using the rapid expansion protocol (REP) in T25 flasks).
54. Grow cells for 11-16 days and screen against individual peptides, peptides pools or TMG's.

Results

Monocyte-derived DCs were generated, T cell populations were sorted, and first and second in vitro stimulations (IVS) were carried out using the reagents and procedures described in the "Reagents" and "Procedures" sections above. The DCs were induced to present a mutated amino acid sequence encoded by a gene comprising a cancer-specific mutation (TMG1-13).

Figure 2:
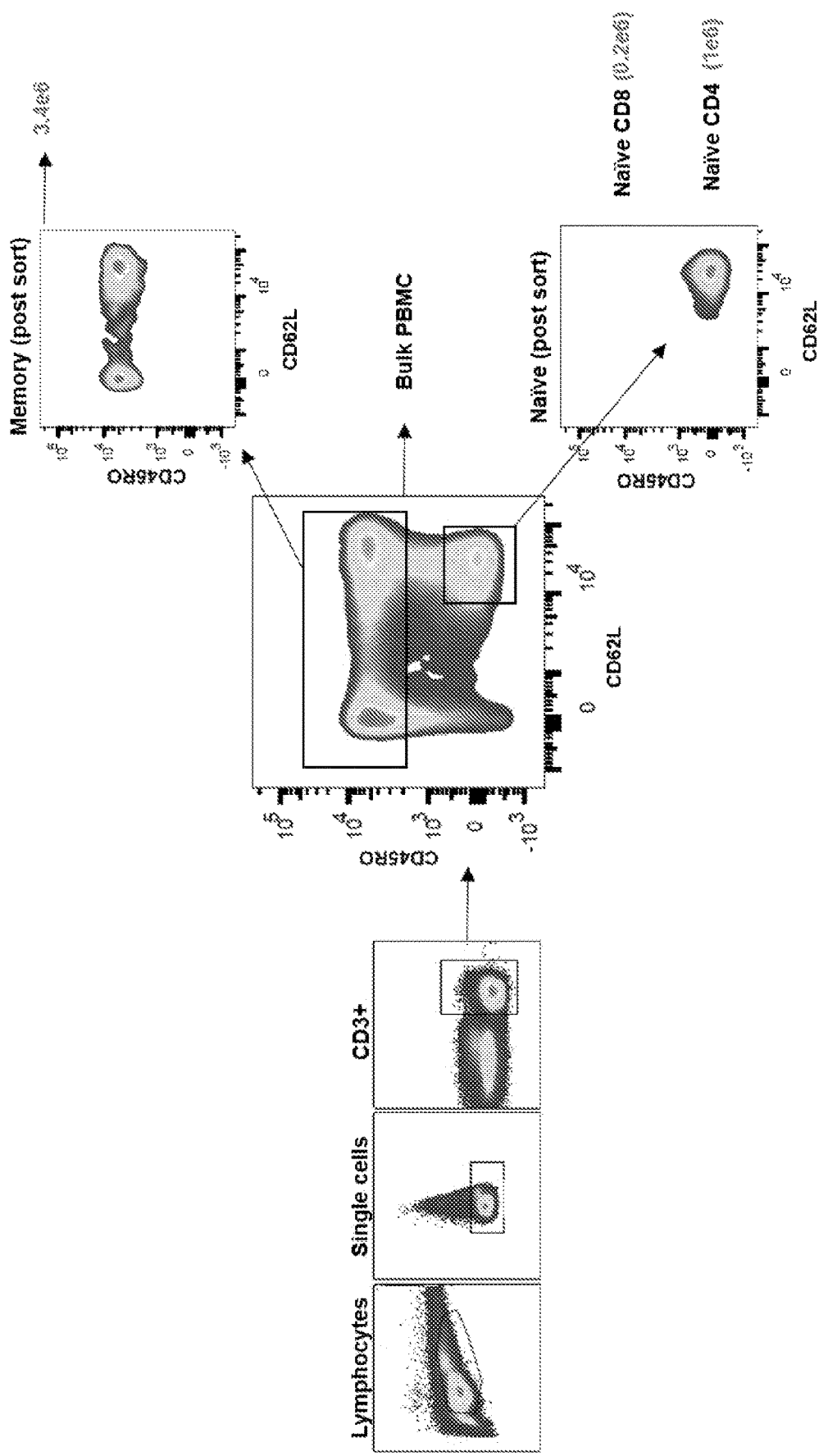
FIG. 2 shows the results of sorting T cells for a naïve T cell phenotype, a memory T cell phenotype or a $T_{EMRA}$ phenotype by flow cytometry.

The results of the sorting of the T cell populations are shown in FIG. 2. As shown in FIG. 2, a population with a memory T cell phenotype (3.4e6 cells) and a population with a naïve T cell phenotype (0.2e6 CD8 naïve cells and 1e6 naïve CD4 cells) were obtained.

Figure 3A:
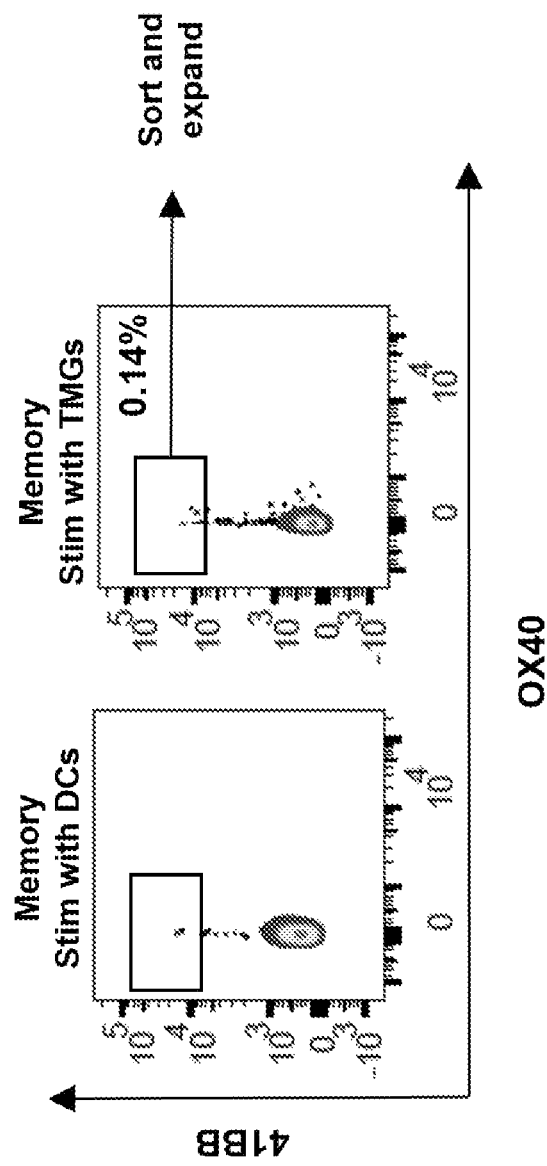
FIG. 3A shows the results of specifically selecting the memory and naïve T cells (which underwent a first and second in vitro stimulation with DCs which present mutated antigens) using flow cytometry on the basis of OX40 and 41BB expression.

The sorted T cells underwent a first and second IVS with DCs which present mutated TMG 1 to 13. After the first and second IVS, the T cells which express one or both of OX40 and 4-1BB were selected. The results are shown in FIG. 3A. As shown in FIG. 3A, a cell population enriched for T cells having antigenic specificity for mutated TMG's was obtained.

Figure 3B:
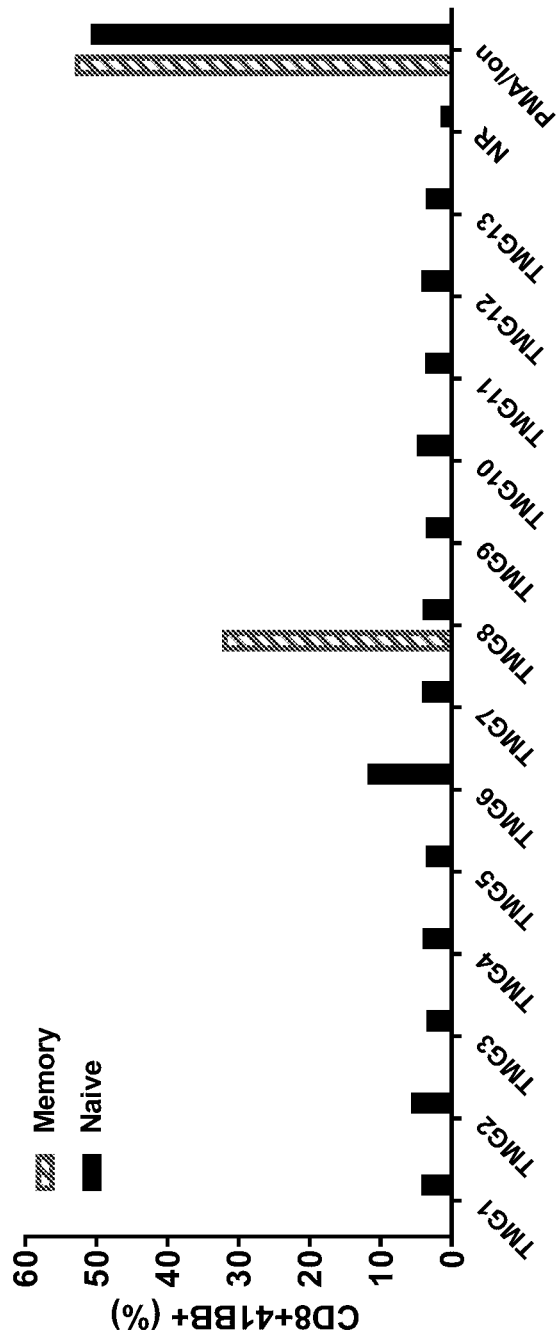
FIG. 3B shows that memory T cells isolated from a patient's PBMC were specific against TMG8.
Figure 3C:
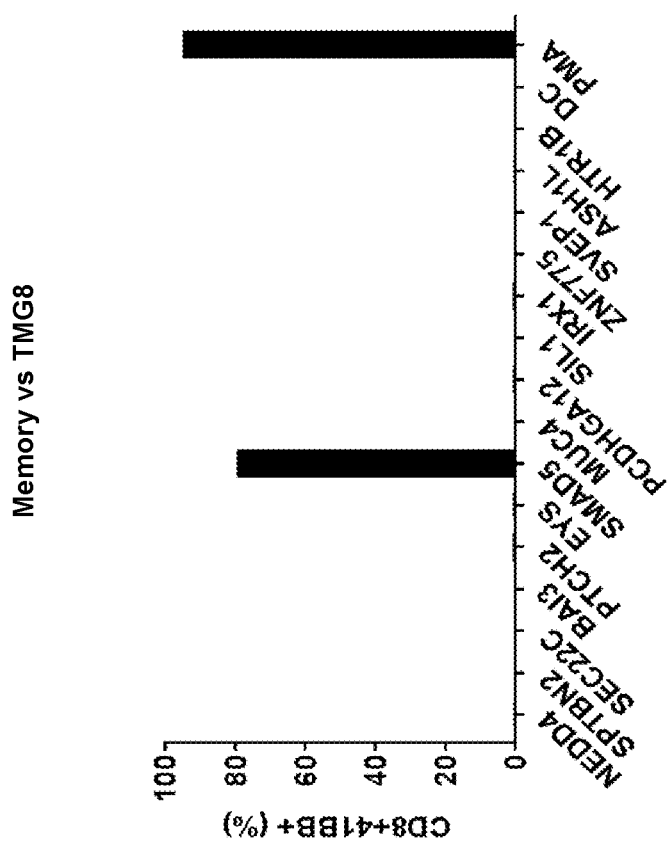
FIG. 3C shows that the reactive memory T cells were specific for the mutated SMAD5 protein.
Figure 3D:
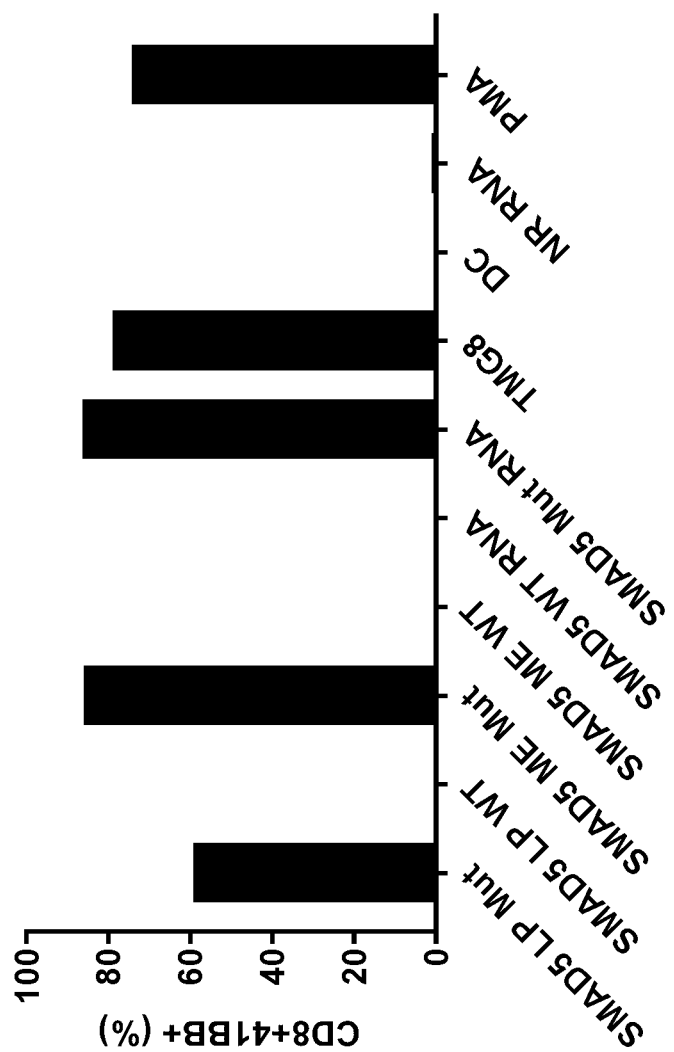
FIG. 3D shows that the reactive memory T cells recognized mutated but not wild type SMAD5 and the full length mutated SMAD5 protein.

The isolated reactive memory cells were shown to have reactivity against mutated TMG8 (FIG. 3B) and specifically against mutated SMAD5 protein (FIG. 3C). The isolated memory cells also specifically recognized mutated and not wild type SMAD5 long peptide (LP), minimal epitope (ME) and cells expressing full length mutated SMAD5 RNA (FIG. 3D).

EXAMPLES 2-6

The following materials and methods were employed in the experiments described in Examples 2-6.

In-Vitro Stimulation of Naïve and Memory T Cells

A. Generation of Monocyte-Derived Immature DCs

Apheresis samples were thawed, washed, set to 5-10×10$^6$ cells/ml with AIM-V media (Life Technologies), and 1.75-

$2 \times 10^8$ viable cells were incubated in T175 flasks (Corning Inc.) at 37° C. After 2 hours, the flasks were washed 2-3 times vigorously with PBS to collect non-adherent cells for T cell sorting. For the adherent cells, 30 ml DC media were added, comprised of RPMI containing 5% human serum, 100 U/ml penicillin and 100 µg/ml streptomycin, 2 mM L-glutamine, 800 IU/ml GM-CSF (Leukine) and 200 U/ml IL-4 (Peprotech), and cells were incubated at 37° C., 5% $CO_2$. On day 4 or 5, cells were harvested and freshly used or frozen for further use. DCs were seeded into low attachment 12- or 6-well plates for peptide loading or TMG transfection. For peptide loading: DCs were loaded with 10-15 µg/ul peptide or peptide pools for 2-12 hrs. For TMG RNA transfection, LIPOFECTAMINE transfection reagent (Invitrogen) or electroporation were used, and the cells were incubated for 8-12 hrs prior to IVS 1. DCs were harvested by washing with PBS and incubated for 5 minutes in 5 ml 0.9 mM EDTA-PBS. DCs were washed with DC medium and resuspended at a concentration of $5 \times 10^5$/ml.

B. Sorting for T Cell Populations

Non-adherent cells were spun, resuspended in 50/50 medium comprising 1:1 mix of RPMI-1640 with L-glutamine (Lonza) and AIMV (Gibco) supplemented with 100 U/ml penicillin, 100 µg/ml streptomycin, 12.5 mM HEPES, and 5% human serum, and rested overnight at 37° C., 5% $CO_2$. Cells were then harvested, washed twice with cold sorting buffer ($PBS^{-/-}$, 1% FCS, 0.5 mM EDTA), resuspended in sorting buffer at $1 \times 10^6$/100 µl and stained with fluorescent-conjugated primary antibodies against CD3, CD8, CD4, CD62L, CD45RO, CD45RA and CCR7.

IVS 1 Set-Up

T cells from sorted populations were collected, counted and spun. T cells were resuspended in CTL medium at a concentration of $2 \times 10^6$/ml. IL-21, 60 ng/ml were added to the T cell fraction. (This will result in a final concentration of 30 ng/ml after the addition of the DCs). DCs were mixed with T cells at a 1:1 (vol/vol) ratio (resulting in a 4:1 T cell:DC ratio, $1 \times 10^6$ T cells/$2.5 \times 10^5$ DCs). 500 µl of the cell mix were transferred into individual wells of a 48-well plate. Cells were incubated at 37° C. for 72 h.

First feeding: Cells were checked under the microscope and the required amount of medium to give 0.5 ml per well was calculated. 500 µl of warm CTL medium containing 60 ng/ml of IL-21 and 3000 IU/ml of IL-2 (referring to the final concentration in the culture medium) were added to each well and incubated at 37° C. for 72 h.

Second feeding: 1 ml of warm CTL medium containing 60 ng/ml of IL-21 and 3000 IU/ml of IL-2 was added to each well of a 12-well plate. Cells and medium from each well of the old plate were transferred to the new 12-well plate. Cells were incubated for 48 h.

Third feeding: 2 ml of warm CTL medium containing 60 ng/ml of IL-21 and 3000 IU/ml of IL-2 (referring to the final concentration in the culture medium) were added to each well of a six-well plate. Cells and medium from each individual well of the old 12-well plate were transferred to individual wells of the new 6-well plate. Cells were incubated for 72 h. From this step, cells could be kept in CTL medium containing 3000 IU/ml IL-2. The number of cells could be expanded until the second IVS and 4-1BB/OX40 enrichment.

For $T_N$ in patients 4148, 4171, and 4238, instead of IL-21 and IL-2, 5 ng/ml of IL-15 and IL-7 were used in the second feeding and 10 ng/ml in the third feeding.

C. IVS 2+41BB/OX40 Enrichment Step

Immature DCs were thawed re-suspended in DC medium+cytokines and transferred into low-attachment 12 or 6 well plates for peptide loading. For peptide loading: DCs were loaded with 10-15 µg/ul peptide or peptide pools for 2-12 hrs. Peptide-loaded DCs were washed and mixed at 1:4 ratio (DC:T) with the appropriate T cell population (usually $4-8 \times 10^6$ T cells were used for each stimulation). Cells were plated into 12- or 6-well plates in 3 ml CTL medium and incubated for 18-24 hrs. Cells were harvested, washed with sorting buffer (PBS, 1% FCS, 0.5 mM EDTA) and stained with anti-human CD8, anti-human CD3, anti-human 4-1BB, anti-human OX40 and anti-human CD4 antibodies. Samples were washed with sorting buffer and the CD3+CD4+41BB+OX40+/CD3+CD8+41BB+OX40+ cells (both double and single positive cells) were sorted. After sorting, cells were kept in CTL medium supplemented with 1500 IU/ml IL-2 (if the cell number is lower than $1 \times 10^5$, the numbers of cells were rapidly expanded using the rapid expansion protocol (REP) and seeded in T25 flasks). Cells were grown for 11-16 days and screened against individual peptides, peptides pools or TMGs.

Generation of Autologous Antigen Presenting Cells (APCs)

Monocyte-derived, immature dendritic cells were generated using the plastic adherence method (Tran et al., *Science*, 350: 1387-90 (2015); Gros et al., *Nat. Med.*, 22(4):433-8 (2016)). Briefly, autologous pheresis samples were thawed, washed, set to $5-10 \times 10^6$ cells/ml with AIM-V media (Life Technologies) and then incubated at approximately $1 \times 10^6$ cells/$cm^2$ in an appropriate size tissue culture flask and incubated at 37° C., 5% $CO_2$. After 120 min, non-adherent cells were collected, and the flasks were vigorously washed with PBS, and then adherent cells were incubated with RPMI (Life technologies) containing 5% human serum 100 U/ml penicillin and 100 µg/ml streptomycin, 2 mM L-glutamine, 800 IU/mL GM-CSF and 800 U/mL IL-4 (Peprotech). On day 4-7, fresh DCs were collected. Fresh or freeze/thawed DCs were used in experiments on day 4-5 after initial stimulation.

Whole-Exome Sequencing and RNASeq Library Prep, Next-Generation Sequencing and Data Analysis Genomic DNA and total RNA were purified using the QIAGEN ALLPREP DNA/RNA mini kit (cat #80204) for patients 4213, 4148, 4238 and 4171 fresh tumor (FrTu) and matched normal apheresis samples following the manufacturer's suggestions. Whole-exome library construction and exon capture of approximately 20,000 coding genes were prepared using Agilent Technologies SURESELECTXT Target Enrichment System (cat#5190-8646) for paired-end libraries coupled with Human ALL EXON V6 RNA bait (cat#5190-8863) (Agilent Technologies, Santa Clara, Calif., USA). Whole exome sequencing (WES) libraries were subsequently sequenced on a NEXTSEQ 500/550 desktop sequencer (Illumina, San Diego, Calif., USA). The library was prepped using gDNA (3 µg) isolated from the fresh tumor tissue following the manufacturer's protocol. Paired-end sequencing was done with an ILLUMINA high-output flow cell kit (300 cycles) (cat# FC-404-2004) using v2 of reagent/flow cell kit. Furthermore, RNASeq libraries were prepared using 2 µg of total RNA with the ILLUMINA TRUSEQ RNA Stranded library prep kit following the manufacturer's protocol. RNA-Seq libraries were paired-end sequenced on a NEXTSEQ 500/550 desktop sequencer (Illumina, San Diego, Calif., USA) again using the same mechanism described above to generate 25+million paired-end reads.

Sequence Alignment, Processing and Variant Calling

Output from the sequencer was de-multiplexed and converted to fastq format using Illumina's bcl2fastq program. Reads were trimmed for quality and to remove and adapter sequence with TRIMMOMATIC software (Bolger et al., *Bioinformatics*, 30: 2114-20 (2014)). Once trimmed, exome reads were aligned to hg19 genome using novoalign from novocraft to create initial starting bams. RNA-seq reads were aligned to hg19 using STAR two pass alignment process (Dobin et al., *Bioinformatics*, 29: 15-21 (2013)). Both RNA-seq and exome bam files were preprocessed according to the GATK best practices protocol. Exome SNVs were called using STRELKA, SOMATIC SNIPER, VARSCAN2 and MUTECT caller tools. Insertions and deletions (In/Dels) were called using STRELKA and VARSCAN2 caller tools. For neoantigens that arise from single nucleotide variants (SNVs) cutoff criteria for evaluation of a variant was Tumor and normal coverage of 10 or greater, Tumor variant read count of 4 or greater, tumor variant frequency of 7% or greater and 2 or greater callers calling that variant. For neoantigens that arose from In/Dels, the criteria was the same except there is no caller criteria. RNA variants were called with VARSCAN caller with no cutoffs. Somatic variants were annotated using ANNOVAR caller against three separate reference databases (Refgene, Ensembl, UCSC). All variants that passed cutoff criteria and those found in COSMIC regardless of cutoff criteria had neoepitopes generated using an in-house python script. This script produced 25-mers with 12 amino acid (aa) flanking the mutation on either side where possible. In the event that this was not possible due to the mutation being located closer than 12 aa from the beginning or end of a transcript, the maximum number of aa that can flank were used. For In/Del mutations, the corresponding change was made to the cDNA sequence, and then 12 aa before the mutation (where possible) were extracted, as well as all amino acids beyond the mutation up until the first stop codon was encountered. If no stop codon was encountered, the neoepitope would encompass all of the sequence up to the end of the cDNA transcript.

Construction of Tandem Minigene and In Vitro Transcription

Tandem minigene (TMG) construction was previously described (Robbins et al., *Nat. Med.*, 19: 747-52 (2013); Gros et al., *J. Clin. Invest.* 124: 2246-2259 (2014)). Briefly, for each nonsynonymous variant identified, a minigene was constructed encoding the mutant amino acid flanked by 12 amino acids of the wild-type sequence. TMGs were cloned into pcRNA2SL using EcoRI and BamHI. Following linearization of the constructs, phenol-chloroform extraction was performed and precipitated the DNA with sodium acetate and ethanol. Next, 1 µg of linearized DNA was used to generate in vitro-transcribed (IVT) RNA using the MMESSAGE MMACHINE T7 Ultra kit (Life Technologies), as instructed by the manufacturer. RNA was precipitated using $LiCl_2$ and resuspended at 1 µg/µl.

Peptide Pulsing and RNA Liposomal Transfection

Peptides were made in-house or purchased from GenScript or peptides & elephants. Briefly, autologous or allogeneic DCs were harvested, washed and resuspended at $0.5-1\times10^6$ cells/mL concentration in DC media supplemented with 800 IU/mL GM-CSF and 800 U/mL IL-4. Next, cells were incubated with peptides for 2-12 hours at 37° C., 5% $CO_2$. Prior to co-culture DCs were collected, washed twice with PBS and resuspended in 50/50 media and then used for co-culture assays.

RNA transfection was done with MMESSENGERMAX reagent (Life Technologies) according to the manufacturer's instructions. Briefly, DCs were harvested, washed and resuspended at $0.75-1\times10^6$ cells/mL and then 0.5 mL were seeded in low-attachment 24-well plate at $0.75-1\times10^6$ cells/mL in DC media supplemented with IL-4 and GM-CSF for 4-12 hours at 37° C., 5% $CO_2$. Following, the MMESSENGER-MAX-OPTI-MEM mixture was incubated for 10 minutes at room temperature (RT). 200-500 ng/well RNAs were diluted in OPTI-MEM medium and mixed with MMESSENGER-MAX-OPTI-MEM in 1:1 ratio and incubated for additional 5 minutes in RT, then the mixture was added to cells and incubated 8-20 hrs at 37° C., 5% $CO_2$.

Co-Culture Assays: IFN-γ ELISPOT, ELISA Assays and Flow Cytometry for Activation Markers CD134 and CD137 Staining When DCs were used as target cells, 3e4-1e5 cells/well were used in 96-well plates. When cells lines were used as target cells, 2e4-5e4 cells/well were used in 96-well plates. 5e3-2e4 1e4-2e4 cells/well effector T cells were used in 96-well plates. All co-cultures were performed in 50/50 media in the absence of exogenously added cytokines. Phorbol 12-myristate 13-acetate: ionomycin mixture (eBioscience) was used as a positive control.

In HLA blocking assays, target cells were incubated with 20-50 µg/mL blocking antibodies for 2 h at 37° C., 5% $CO_2$, and then effector cells were added and incubated for 12-18 h.

IFNγ ELISPOT assays were done as previously described (Tran et al., *Science*, 350: 1387-90 (2015)). ELISPOT plates were scanned and counted using an IMMUNOSPOT plate reader and associated software (Cellular Technologies, Ltd). The cells from the co-culture were harvested from ELISPOT wells prior to IFNγ spots development, stained for flow cytometry, and surface expression of CD134 and CD137 was assessed using BD FACSCANTOI system, BD FACSCANTOII system or BD LSR FORTESSA system. All flow cytometry data were analyzed using FLOWJO software (TreeStar Inc).

Single Cell Sorting and Single Cell RT-PCR

Single-cell reactive T cells were sorted into 96-wells plate containing reverse transcription-polymerase chain reaction (RT-PCR) buffer based on activation markers (CD134, CD137) or tetramer staining using FACSARIA instrument (BD Biosciences). TCR sequences from the sorted single cells were obtained by a series of two nested PCR reactions as previously described (Pasetto et al., *Cancer Immunol. Res.*, 4: 734-743 (2016)). Briefly, multiplex PCR with multiple Vα and Vβ region primers and one primer for Cα and Cβ regions each was performed using the ONE-STEP RT-PCR kit (Qiagen). The RT-PCR reaction was performed according to the manufacturer's instructions using the following cycling conditions: 50° C. 15 min; 95° C. 2 min; 95° C. 15 s, 60° C. 4 min×18 cycles; 4° C. For the second amplification reaction, 4 µl from the first RT-PCR product were used as a template in total 25 µl PCR mix using HOTSTARTAQ DNA polymerase (Qiagen) and multiple internally nested Vα and Vβ region primers and one internally nested primer for Cα and Cβ regions each (final concentration of each primer is 0.6 µM). The cycling conditions were 95° C. 15 min; 94° C. 30 s, 50° C. 30 s, 72° C. 1 min×50 cycles; 72° C. 10 min; 4° C. The PCR products were purified and sequenced by the Sanger sequencing method with internally nested Cα and Cβ regions primers by Beckmann Coulter.

TCR Survey and Deep Sequencing

TCR-Vβ deep sequencing was performed by IMMUNOSEQ assay (Adaptive Biotechnologies (Seattle, Wash.)) on genomic DNA isolated from peripheral blood T cells, and frozen tumor tissues. T cell numbers in sequenced samples ranged from ~$2\times10^4$ cells to $1\times10^6$. TRB clonality and productivity were analyzed using IMMUNOSEQ Analyzer 3.0 data analysis tool (Seattle, Wash.). Only productive TCR rearrangements were used in the calculations of TCR frequencies.

TCR Cloning, Retrovirus Production, and Transduction of T Cells

TCR cloning and transduction of T cells were performed as previously described (Tran et al., *Science*, 350: 1387-90 (2015); Gros et al., *J. Clin. Invest.*, 124: 2246-2259 (2014)). Briefly, TRA V-J-encoding sequences were fused to mouse TCRβ constant chain, and TRB V-D-J-encoding sequences were fused to mouse TCRα constant chain (Cohen et al., *Cancer Res.*, 66: 8878-86 (2006)). Mouse constant chains were modified to improve TCR αβ pairing, as previously described (Cohen et al., *Cancer Res.*, 66: 8878-86 (2006)). The full-length TRB and TRA chains were separated by a furin SGSG (SEQ ID NO: 1) P2A linker. TCR construct was cloned into a pMSGV1 retroviral vector.

For transduction, autologous or allogeneic pheresis samples were thawed and set to 2e6 cells/ml in T-cell media, which included a 50/50 mixture of RPMI and AIM-V media supplemented with 5% in-house human serum, 10 μg/ml gentamicin (CellGro), 100 U/ml penicillin and 100 μg/ml streptomycin, and 2 mM L-glutamine (all from Life Technologies). 2e6 cells/mL were stimulated in a 24-well plate with 50 ng/ml soluble OKT3 (Miltenyi Biotec) and 300 IU/ml IL-2 (Chiron) for two days prior to retroviral transduction. Retroviral supernatants were generated in a HEK-293GP packaging line as described previously (Tran et al., *Science*, 350: 1387-90 (2015); Pasetto et al., *Cancer Immunol. Res.*, 4: 734-743 (2016)). Briefly, pMSGV1 plasmid encoding mutation-specific TCR (2 μg/well) and the envelope-encoding plasmid RD114 (0.75 μg/well) were co-transfected into 1e6 239GP cells per well of a 6-well poly-D-lysine-coated plates using LIPOFECTAMINE 2000 transfection reagent (Life Technologies). Retroviral supernatants were collected at 42-48 h after transfection, diluted 1:1 with DMEM media, and then centrifuged onto RETRONECTIN reagent-coated (10 μg/ml, Takara), non-tissue culture-treated 6-well plates at 2,000 g for 2 h at 32° C. Stimulated T cells (2e6 per well, at 0.5e6 cells/ml in IL-2 containing T-cell media) were then spun onto the retrovirus plates for 10 min at 300-350 g. Stimulated T cells were transduced overnight, removed from the plates and further cultured in rIL-2 containing T-cell media. GFP and mock transduction controls were included in transduction experiments. Cells were typically assayed 10-14 days post-retroviral transduction.

Antibodies

The following titrated anti-human antibodies were used for cell surface staining: CCR7-BB515 or FITC (clone: 3D12), CD45RO-PE-Cy7 (clone: UCHL1), CD45RA-APC or BD HORIZON V450 reagent (HI100), PE-Cy7 (CD62L-APC (clone: DREG-56), CD4-PE, FITC, BV605 (clone: OKT4), CD3-AF700 or APC-H7 (clone: UCHT1), CD4-FITC, PE, PE-Cy7, APC-H7 (clone: SK3), CD8-PE-Cy7 (clone: SK1), OX40-PE-Cy7 or FITC (clone: Ber-ACT35), 4-1BB-APC (clone: 4B4-1). All antibodies were from BD Biosciences. For MHC blocking assays, the following antibodies were used: pan-class-I (clone: W6/32), pan-class-II (clone: IVA12), HLA-DR (clone: HB55), HLA-DP (clone: B7/21), and HLA-DQ (clone: SPV-L3). For cells, stimulation purified anti-CD3 was used (OKT3, Miltenyi Biotech).

EXAMPLE 2

This example demonstrates that neoantigen-reactive TCRs were detected only in memory cells ($T_{CM}$, $T_{EM}$, and $T_{EMRA}$) but not in $T_N$ cells.

Figure 4A:
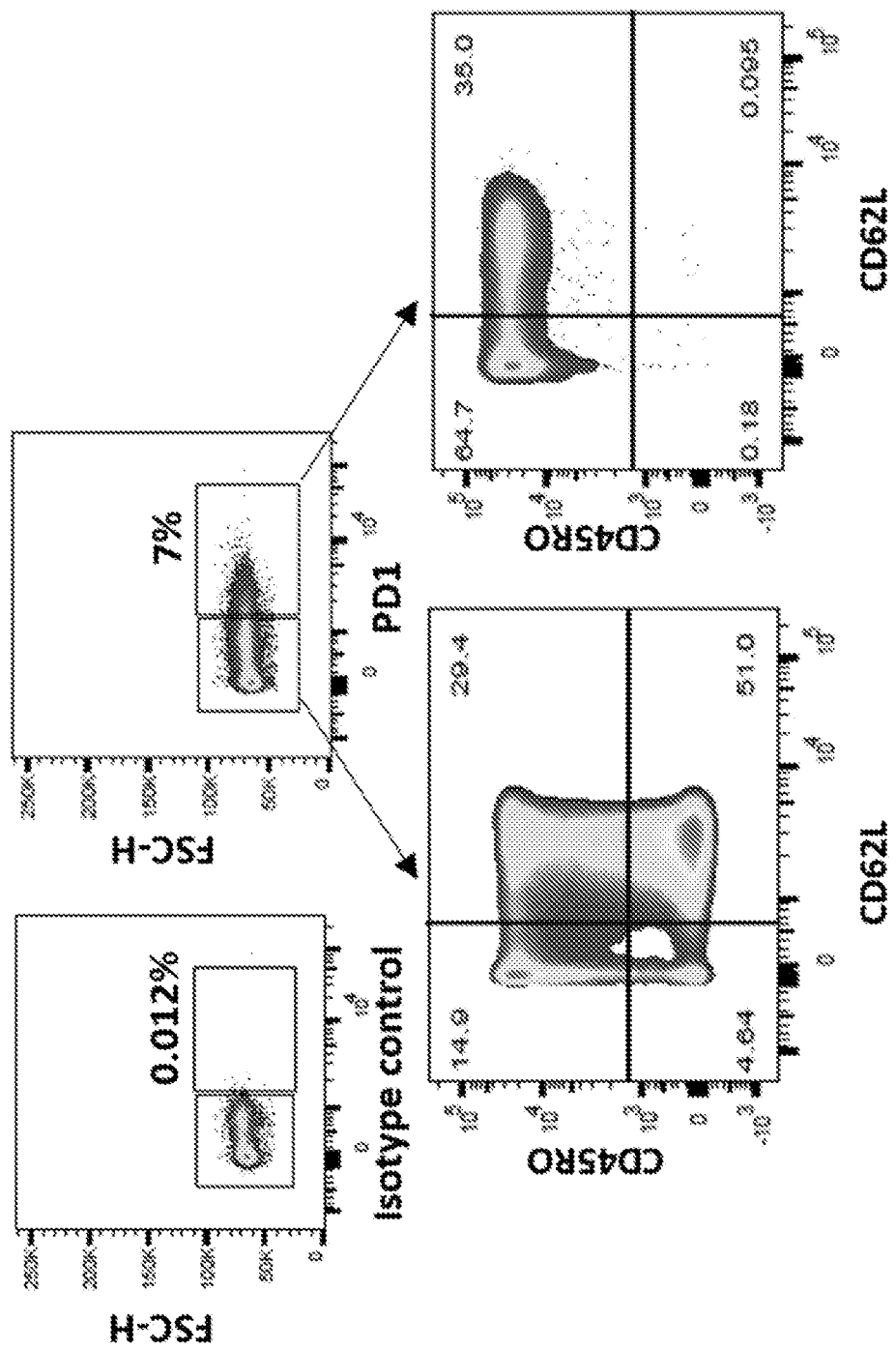
FIG. 4A show FACS plots showing the gating strategy used for the phenotypic analysis of PD1+ peripheral T cells including representative data from one of the four patients.
Figure 4B:
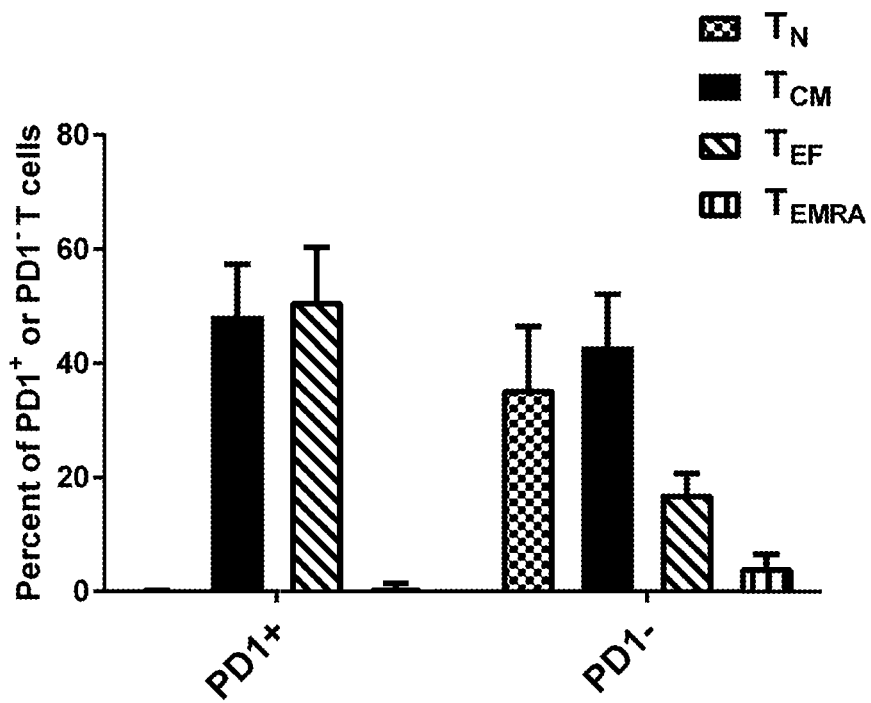
FIG. 4B is a graph showing the percentage of PD1+ or PD1− T cells in $T_{CM}$, $T_{EM}$, $T_{EMRA}$, and $T_N$ cells.
Figure 4C:
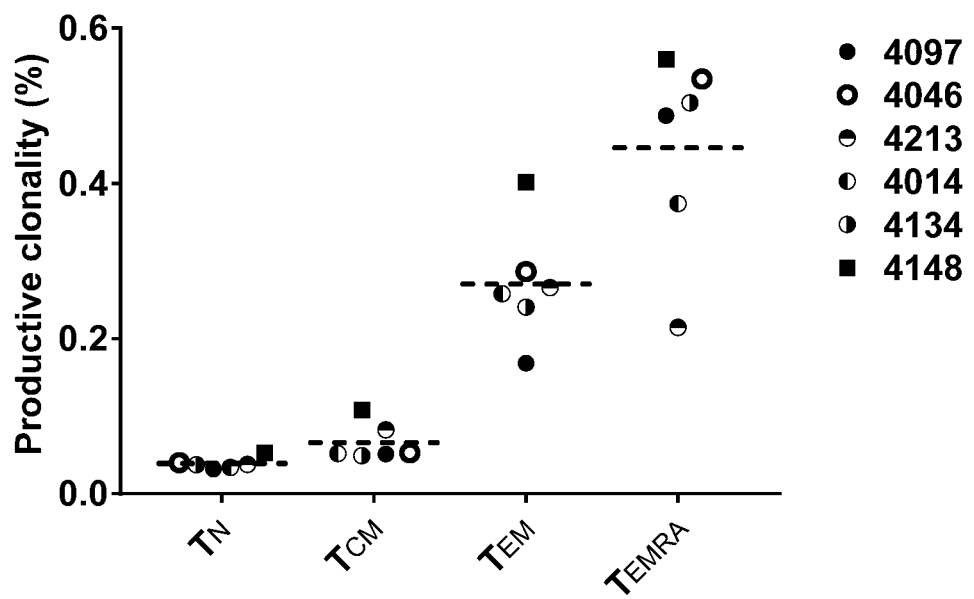
FIG. 4C is a graph showing the productive clonality (%) of TCR-Vβ sequences of each T cell population isolated in Table 1 (paired T-test, *** P<0.001, * P<0.05; dashed line, mean).
Figure 4D:
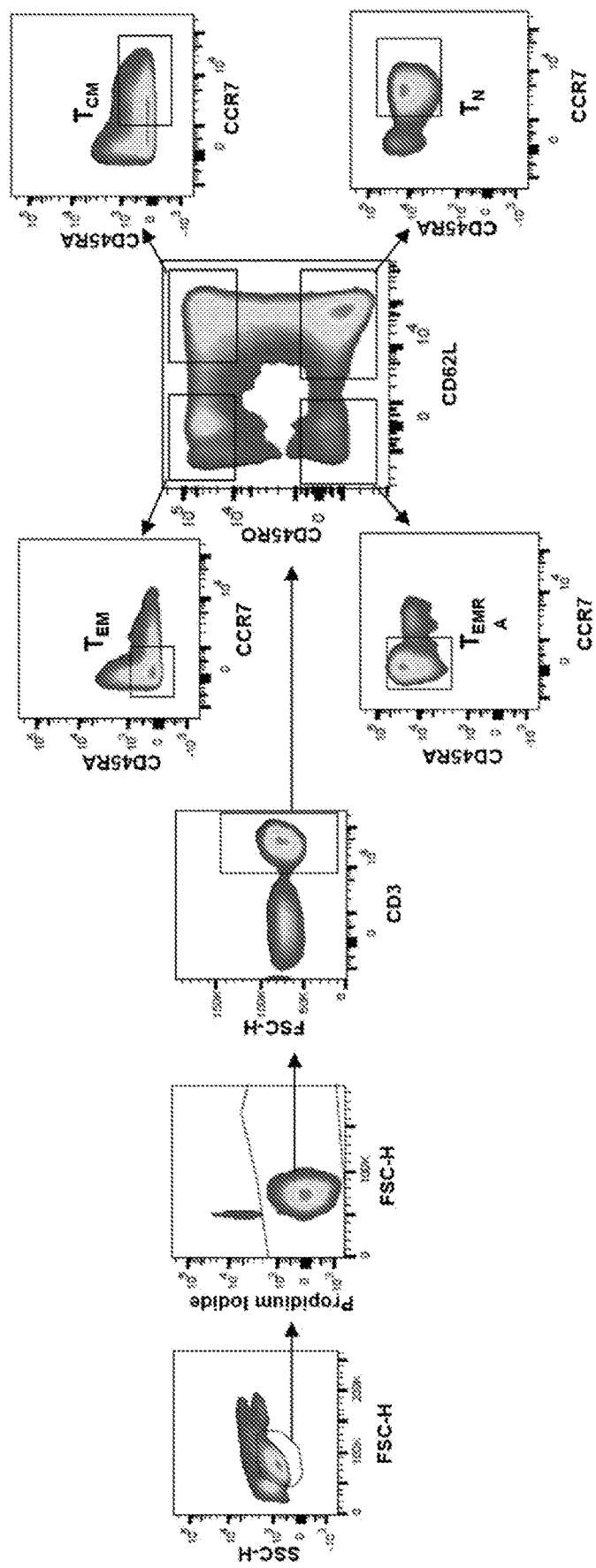
FIG. 4D show FACS plots showing the sorting strategy used to sort peripheral T cell populations and PD1+ cells. Frozen PBMC were thawed and rested overnight in complete T cell medium without cytokines. Cells were collected and stained using antibodies against CD3, CD8, CD62L, CD45RO, CCR7 and CD45RA. For sorting, cells were gated based on CD45RO and CD45RA following by second gate based on CD45RA and CCR7. Cells were than sorted according to the gate set on FIG. 4D from the CD45RA/CCR7 gate.
Figure 4E:
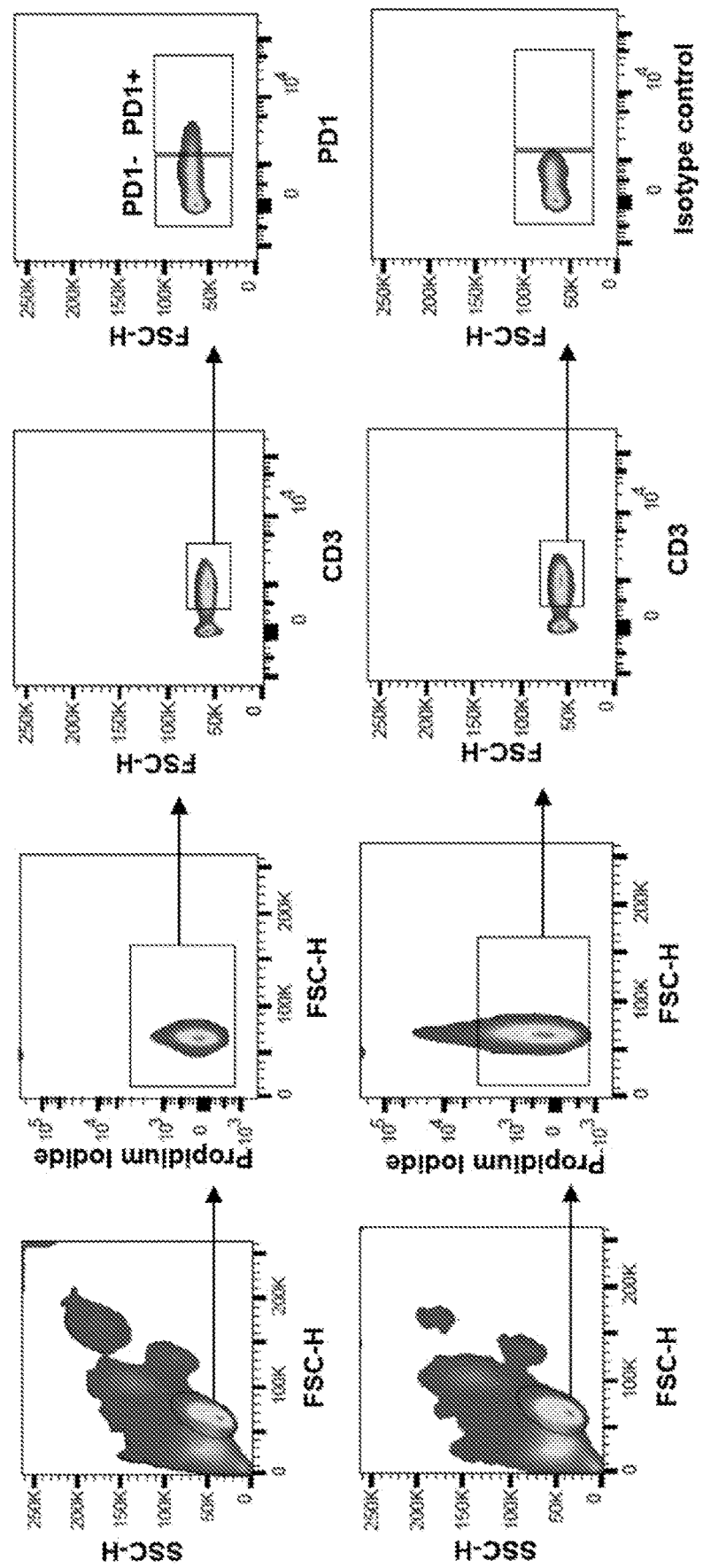
FIG. 4E show FACS plots showing the sorting strategy used to sort peripheral T cell populations and PD1+ cells. Frozen PBMC were thawed and rested overnight in complete T cell medium without cytokines. Cells were collected and stained using antibodies against CD3, CD8, CD4, and PD1. As negative control, cells were stained with the matched Isotype control. All cells in the PD1 stained sample above the negative isotype control level were sorted, snap frozen and send to TCR-VB sequencing.

To determine whether the neoantigen-reactive T cells are present in the memory compartment of epithelial cancer patients, the phenotype of PD-1$^+$ T cells in the peripheral blood of four metastatic gastrointestinal (GI) cancer patients (patients 4217, 4254, 4257 and 4252) was initially tested. Analysis of all four samples revealed that the majority of CD3$^+$PD1$^+$ T cells were central memory T cells ($T_{CM}$) or effector memory T cells ($T_{EM}$) (FIGS. 4A-4B and 4E), while no $T_N$ cells were shown to be PD-1 positive. The majority of the terminally differentiated effector memory ($T_{EMRA}$) cells did not express PD-1.

To further address whether neoantigen-specific T cells were enriched in the memory T cell subset, $T_N$, $T_{CM}$, $T_{EM}$, and $T_{EMRA}$ cells from peripheral blood lymphocytes (PBL) of six epithelial cancer patients with known neoantigen-reactive TCRs that were previously found in their tumor infiltrating lymphocytes (TILs) were retrospectively sorted, and TCR-Vβ deep-sequencing was performed. Comparison of the TCR-Vβ sequences obtained from TILs with the sequences of the matched PBL subsets showed that neoantigen-reactive TCRs were detected only in memory cells ($T_{CM}$, $T_{EM}$, and $T_{EMRA}$) but not in $T_N$ cells (Table 1, FIG. 4D). The frequency of the neoantigen-reactive T cells in the blood was low, ranging from 0.02 to 0.0007% of each T cell subpopulation. Further analysis of the productive clonality based on TCR-Vβ sequences revealed a clear hierarchy of clonality among the different T cell populations (FIG. 4C), thus demonstrating that $T_{EM}$ and $T_{EMRA}$ memory populations are significantly more clonal than $T_N$ cells.

TABLE 1

| Histology | Patient | Target neoantigen | TN | TCM | TEM | TEMRA |
| --- | --- | --- | --- | --- | --- | --- |
| Colon | 4213 | SMAD5 | — | — | 0.000812 | — |
|  |  | DDX1 | — | 0.003584 | — | — |
| Ovarian | 4097 | HIST1H1B | — | — | — | — |
|  | 4046 | USPX | — | 0.001392 | 0.000776 | 0.001392 |
| NSCLC | 4014 | USP11 | — | — | — | — |
|  | 4134 | GRB7 | — | — | 0.023095 | — |
| Endometrial | 4148 | KRAS | — | 0.002543 | 0.000715 | — |

EXAMPLE 3

This example demonstrates the isolation of neoantigen-reactive cells from peripheral blood of epithelial cancer patients.

To test the feasibility of using memory T cells to isolate neoantigen-reactive T cells, an IVS method (FIG. 1) was developed. This approach was retrospectively tested using PBLs from two metastatic colon cancer patients (patient 4213 and 4217, FIGS. 5H-5L). Patient (Pt.) 4213 was screened in the laboratory for the presence of neoantigen-specific TILs for potential ACT, as described earlier (Robbins et al., *Nat. Med.* 19: 747-52 (2013)). Briefly, using whole-exome and RNA sequencing, somatic mutations that were present in two metastatic tumors derived from patient 4213 were identified. Two neoantigens were identified in the initial screen, SMAD5$^{P268inPKH}$, and DDX1$^{S281F}$ (FIGS. 5M-5N).

Here, memory ($T_{CM}$, $T_{EM}$, and $T_{EMRA}$), $T_N$ and bulk PBL cells from PBMC of Pt.

4213 (FIG. 4D) were sorted and co-cultured with DCs loaded with RNA encoding tandem minigenes (TMGs) for 14 days in the presence of IL-21, IL-7, and IL-15. Each TMG comprises a string of RNA minigenes encoding identified mutations flanked on each side by 12 wild-type amino acids from the parent protein.

Figure 5A:
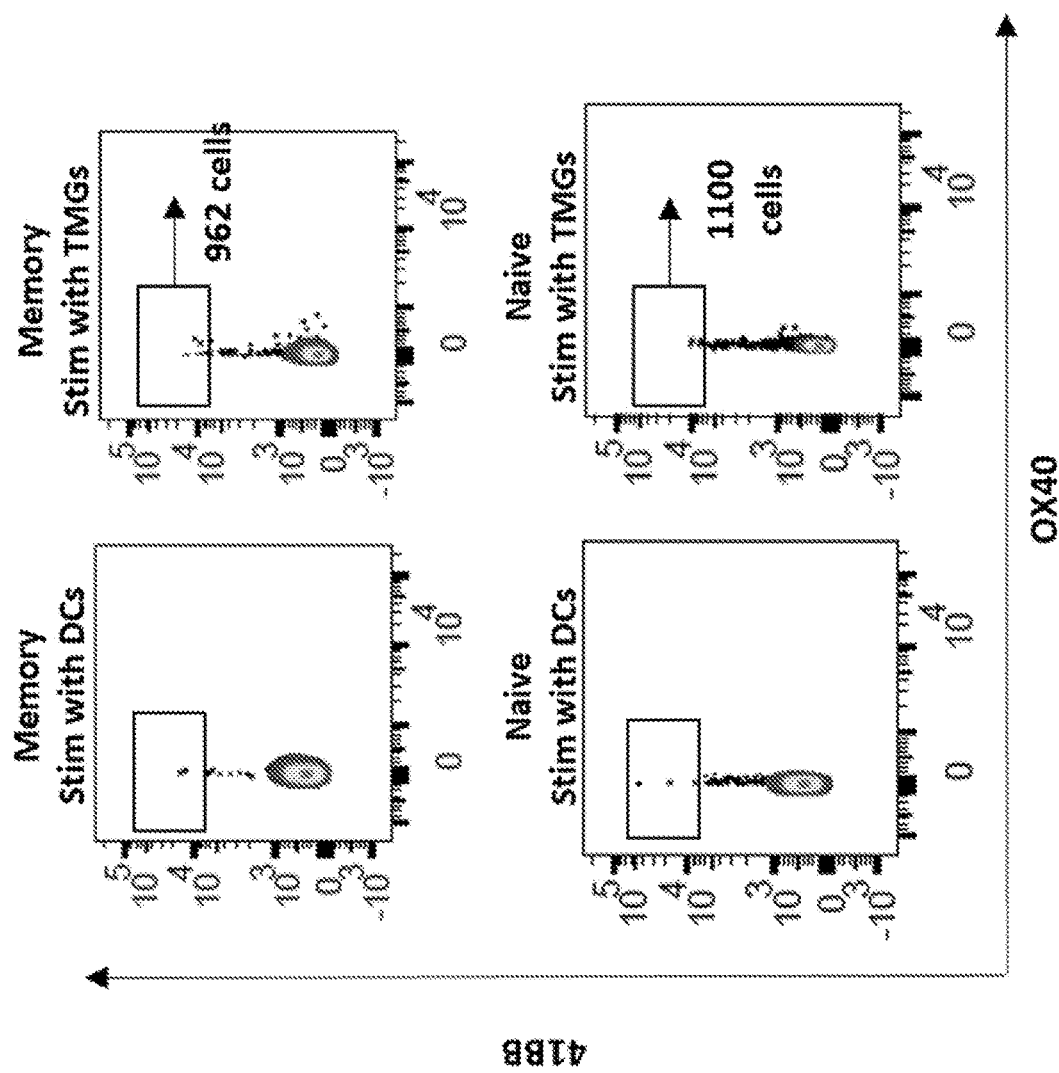
FIG. 5A show FACS plots showing the number of cells expressing 41BB and OX40 after memory and naive CD8 cells were co-cultured with autologous DCs transfected with 13 TMGs harboring 201 mutated 25-mer sequences for 18 hours. Activated T Cells were stained for CD3, CD8, 41BB, and OX40 and sorted based on 41BB and OX40 expression to enrich for neoantigen reactive cells.

After 14 days, memory and $T_N$ cells were re-stimulated with DCs loaded with all TMGs and sorted based on CD8+, CD4+ and expression of the T-cell activation marker 4-1BB to enrich for neoantigen reactive T cells (FIG. 5A). The number of activated CD8+ T cells sorted was low, 962 from memory, and 1100 from $T_N$ (FIG. 5A), possibly due to the low frequency of neoantigen-specific cells, as shown in Table 1.

Figure 5B:
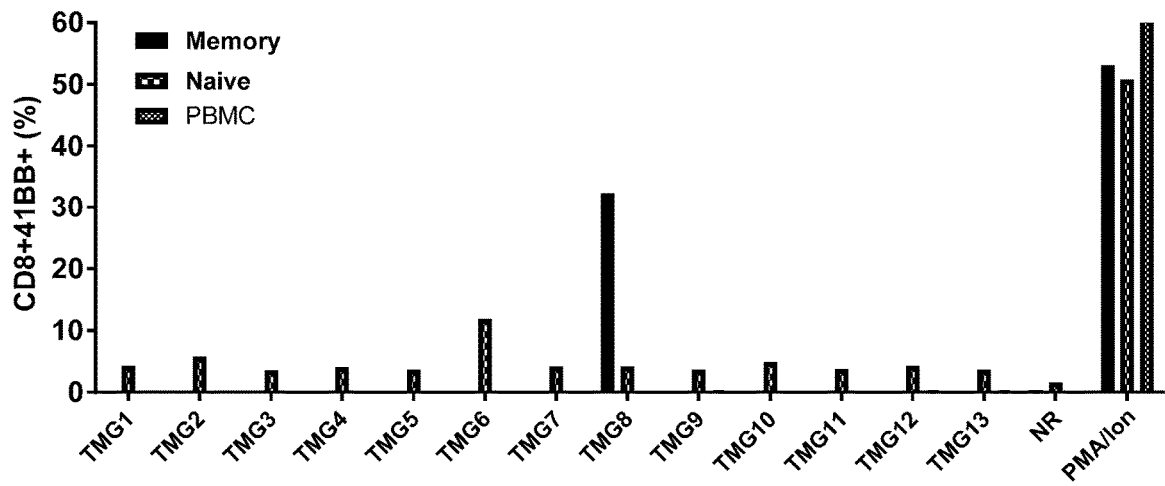
FIG. 5B is a graph showing the percentage of CD8+ 41BB+ cells measured after memory, $T_N$ and PBMC were co-cultured with autologous DCs transfected with TMGs 1 to 13 for 18 hours, stained with CD3, CD8, and 41BB and analyzed for surface expression of 41BB as a marker for T cell activation.
Figure 5C:
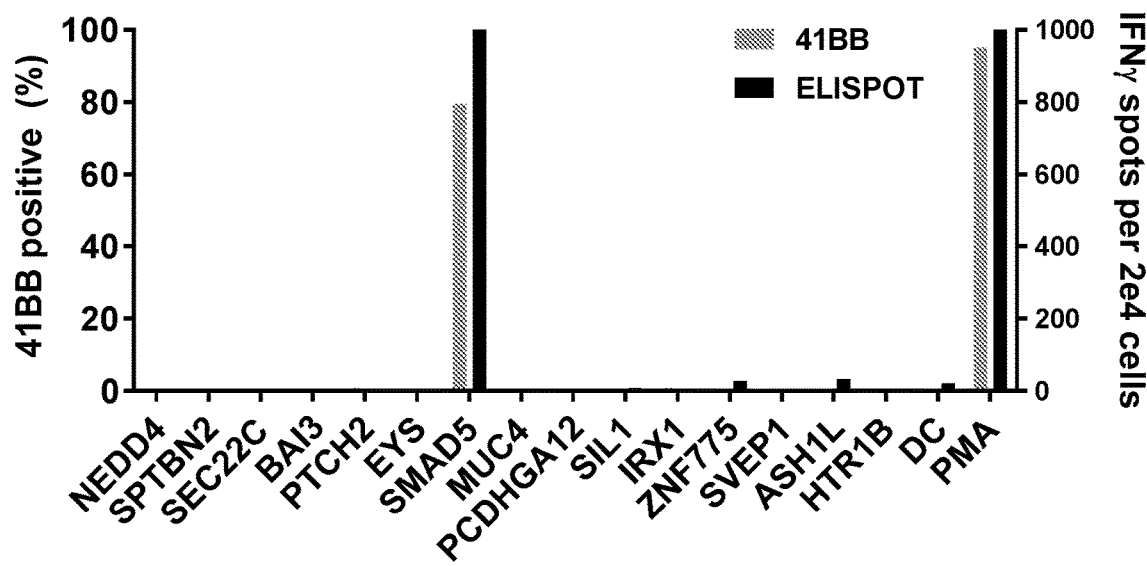
FIG. 5C is a graph showing the percentage of 41BB positive cells and the number of IFNγ spots per 2e4 cells measured after memory CD8 cells isolated in FIG. 5A were co-cultured for 18 hours with autologous DCs that were individually pulsed with the mutated peptides encoded by TMG-8 and tested either by flow cytometry for 41BB expression or IFNγ-secretion using ELISPOT assay.
Figure 5D:
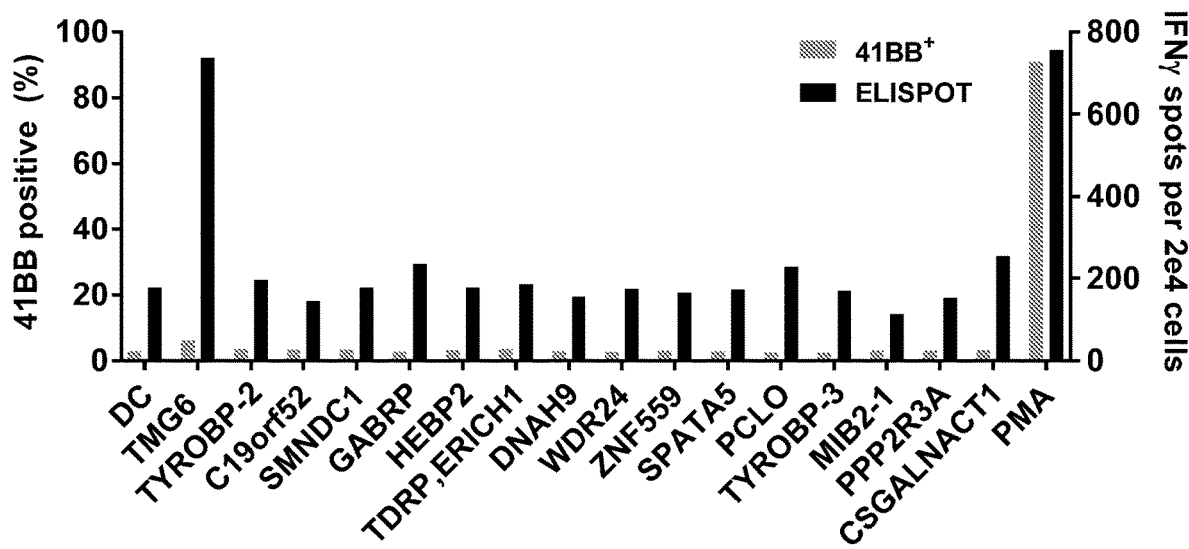
FIG. 5D is a graph showing the percentage of 41BB positive cells and the number of IFNγ spots per 2e4 cells measured after naive CD8 cells isolated in FIG. 5A were co-cultured for 18 hours with autologous DCs that were individually pulsed with the mutated peptides encoded by TMG-6 and tested either by flow cytometry for 41BB expression or IFNγ-secretion using ELISPOT assay.

The numbers of cells were then expanded and screened against all 13 TMGs to test for neoantigen recognition. Memory and naïve CD8+ T cells were reactive against TMG-8 and TMG-6, respectively, while bulk PBL did not recognize any TMGs (FIG. 5B). To identify the specific neoantigens in TMG-8 and TMG-6, the enriched memory and $T_N$ cells were co-cultured with autologous DCs that were individually pulsed with the mutated peptides encoded by TMG-8 or TMG-6. TMG-8 encoded mutated NEDD4, SPTBN2, SEC22C, BAI3, PTCH2, EYS, SMAD5, MUC4, PCDHGA12, SILL IRX1, ZNF775, SVEP1, ASH1L, and HTR1B peptides. TMG-6 encoded mutated TYROBP-2, C19orf52, SMNDC1, GABRP, HEBP2, TDRP(ERICH1), DNAH9, WDR24, ZNF559, SPATA5, PCLO, TYROBP-3, MIB2-1, PPP2R3A, and CSGALNACT1 peptides. TMG-8 reactive CD8+ memory T cells recognized the SMAD5$^{P268inPKH}$ mutation (FIG. 5C), while the TMG-6 reactive CD8+ $T_N$ cells did not recognize any single peptide from TMG-6 (FIG. 5D).

Figure 5E:
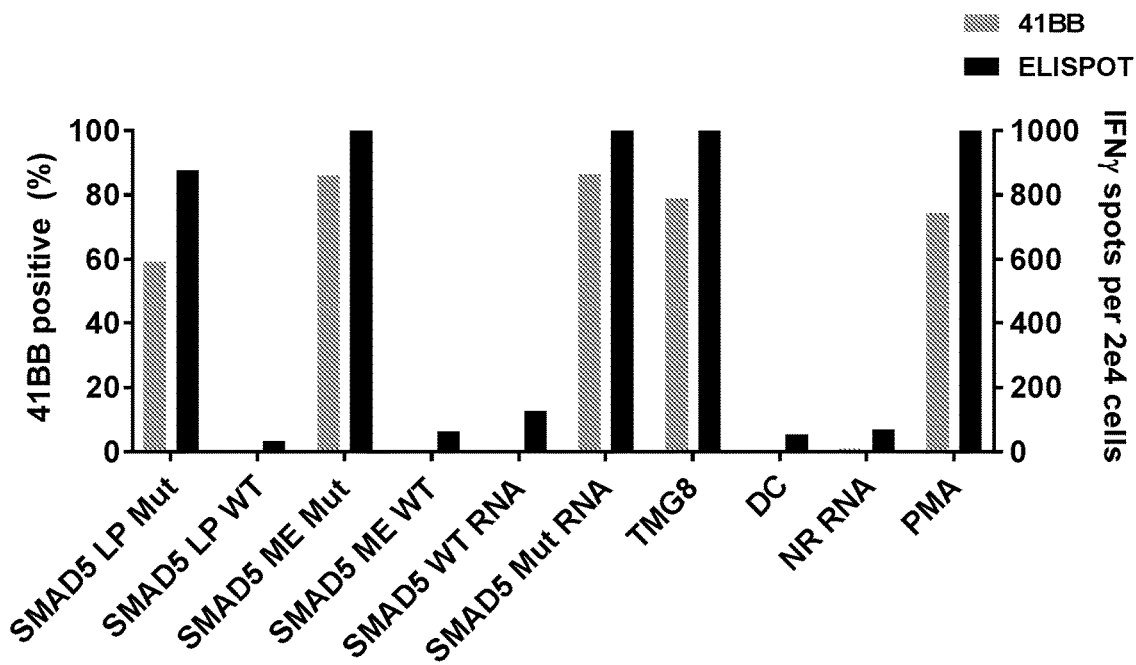
FIG. 5E is a graph showing the percentage of 41BB positive cells and the number of IFNγ spots per 2e4 cells measured after memory CD8 cells isolated in FIG. 5A were co-cultured for 18 hours with autologous DCs that were loaded with WT or Mut SMAD5 LP, predicted minimal epitope (ME) and full-length WT and mutated SMAD5 RNA. Cells were tested for antigen recognition by flow cytometry for 41BB expression or IFNγ-secretion using ELISPOT assay.

The SMAD5$^{P268inPKH}$-reactive memory CD8+ cells were further tested for the recognition of WT and mutated long peptides, the predicted minimal epitope and a full-length SMAD5 RNA corresponding to the mutated and WT protein sequences. As shown in FIG. 5E, the SMAD5 reactive cells recognized the mutated and not the WT LP, minimal epitope and full-length SMAD5 RNA.

Figure 5F:
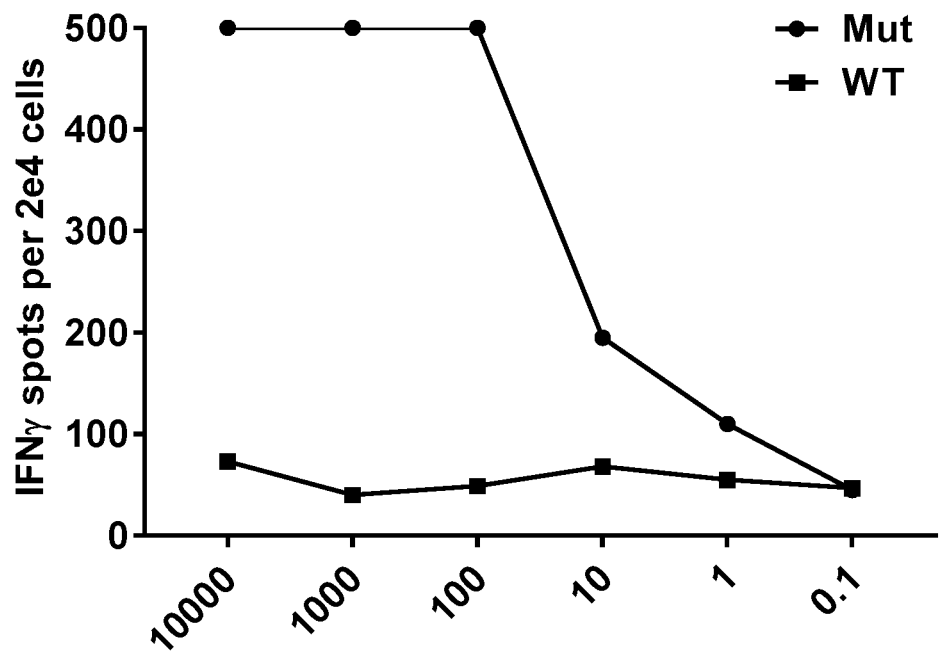
FIG. 5F is a graph showing the number of IFNγ spots per 2e4 cells measured after TCR-transduced PBLs were co-cultured with DCs pulsed with a serial dilution of SMAD5 Mutated or WT peptides.
Figure 5G:
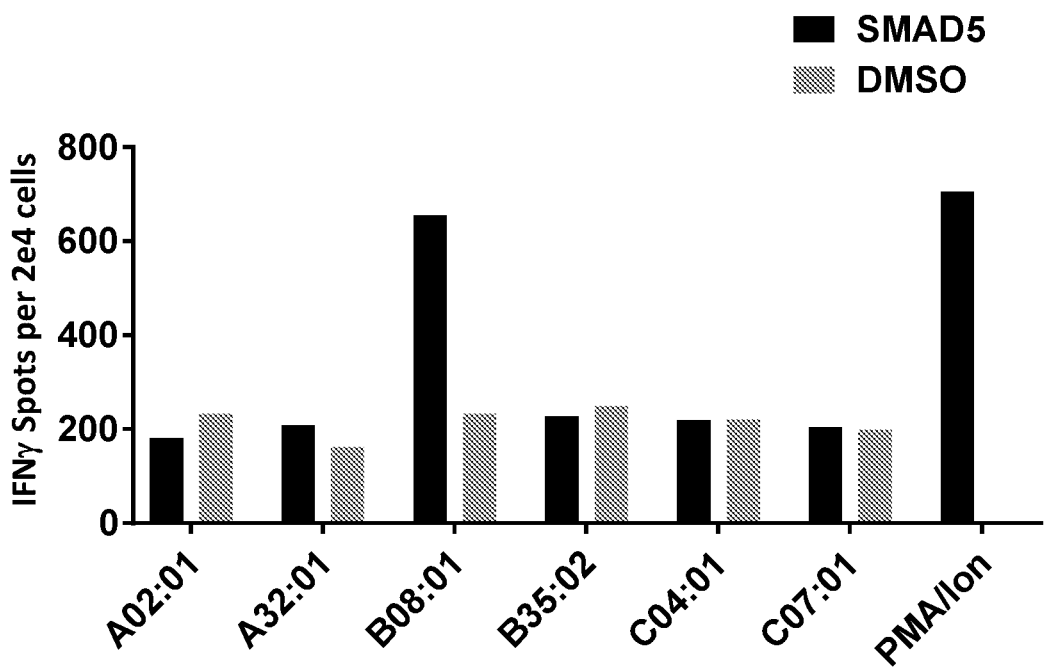
FIG. 5G is a graph showing the number of IFNγ spots per 2e4 cells measured after COST cells were transfected with patient's class I HLA and co-cultured with TCR-transduced cells. Reactivity was determined by ELISPOT for IFNγ.
Figure 5H:
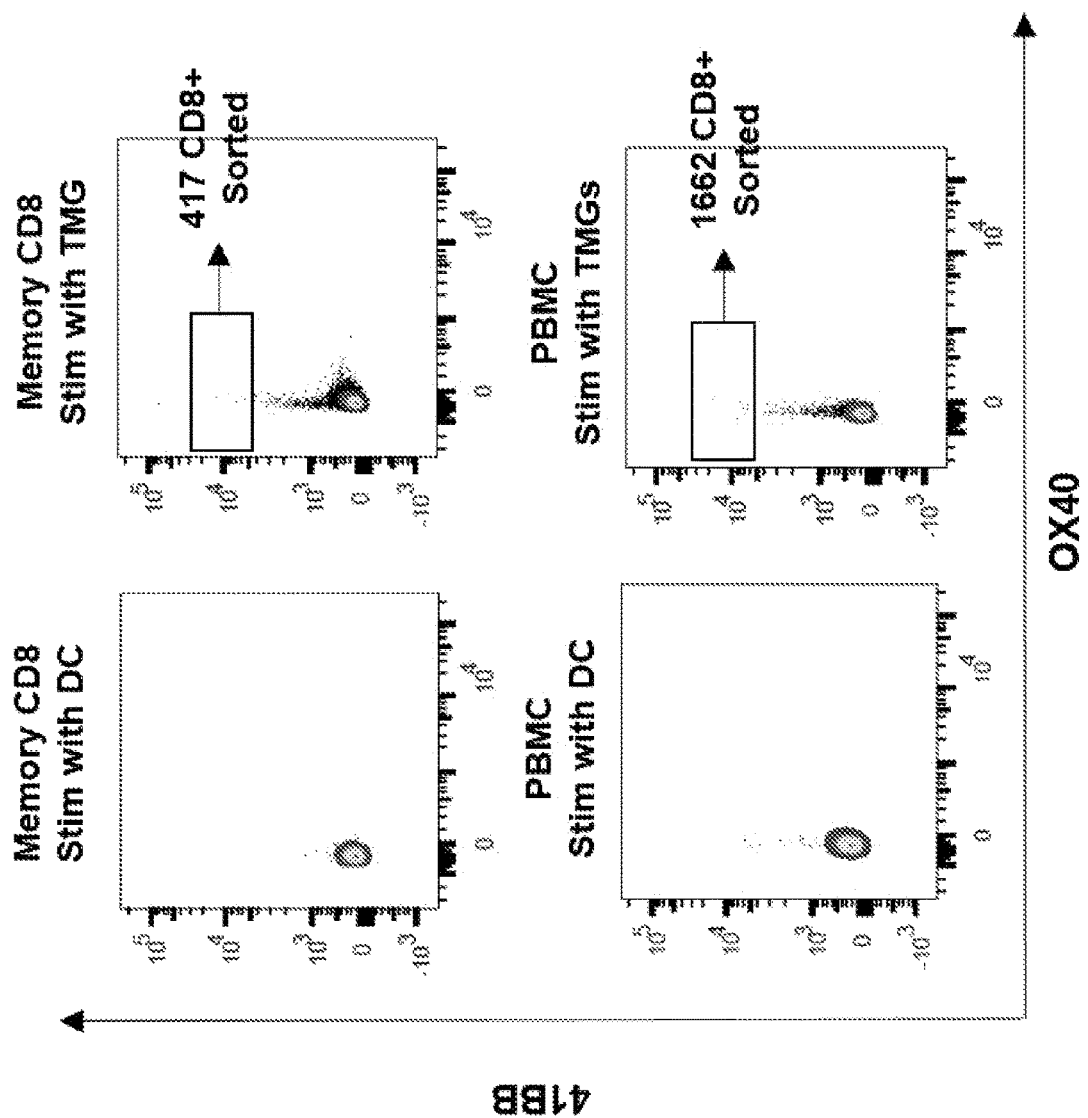
FIG. 5H show FACS plots showing the number of cells expressing 41BB and OX40 after memory and bulk CD8 cells were co-cultured with autologous DCs transfected with 3 TMGs for 18 hours. Activated T Cells were stained for CD3, CD8, 4-1BB, and OX40 and sorted based on 4-1BB and OX40 expression to enrich for neoantigen reactive cells.
Figure 5I:
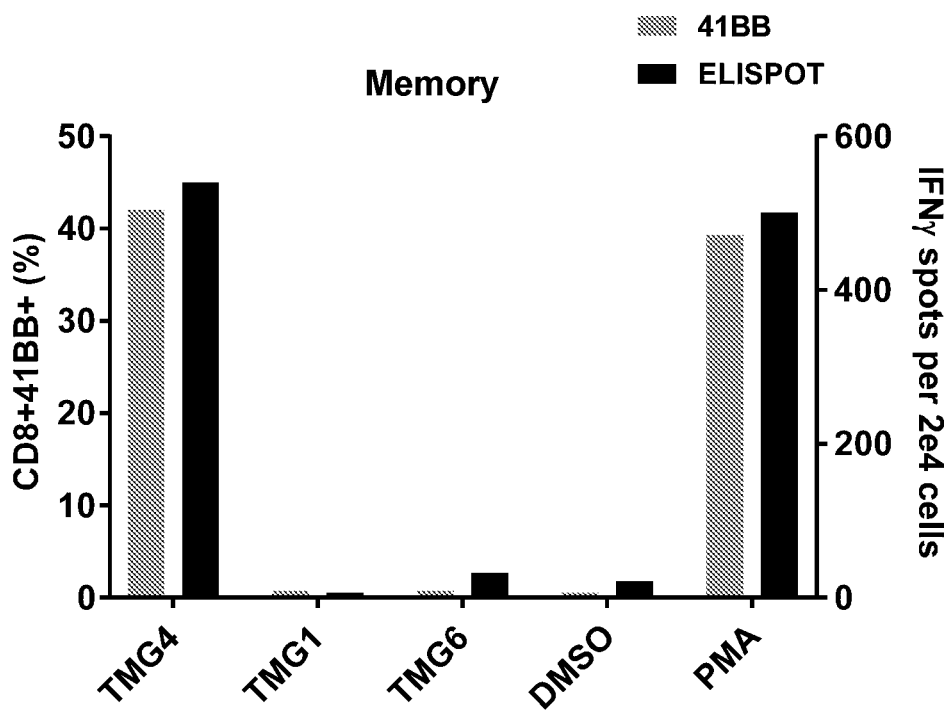
FIGS. 5I-5J are graphs showing the percentage of CD8+ 41BB+ cells and the number of IFNγ spots per 2e4 cells after memory T cells (FIG. 5I) and bulk PBLs (FIG. 5J) isolated in FIG. 5H were co-cultured with autologous DCs transfected with TMGs 1, 4 and 6 for 18 hours, stained with CD3, CD8, and 4-1BB and analyzed for surface expression of 4-1BB as a marker for T cell activation.
Figure 5J:
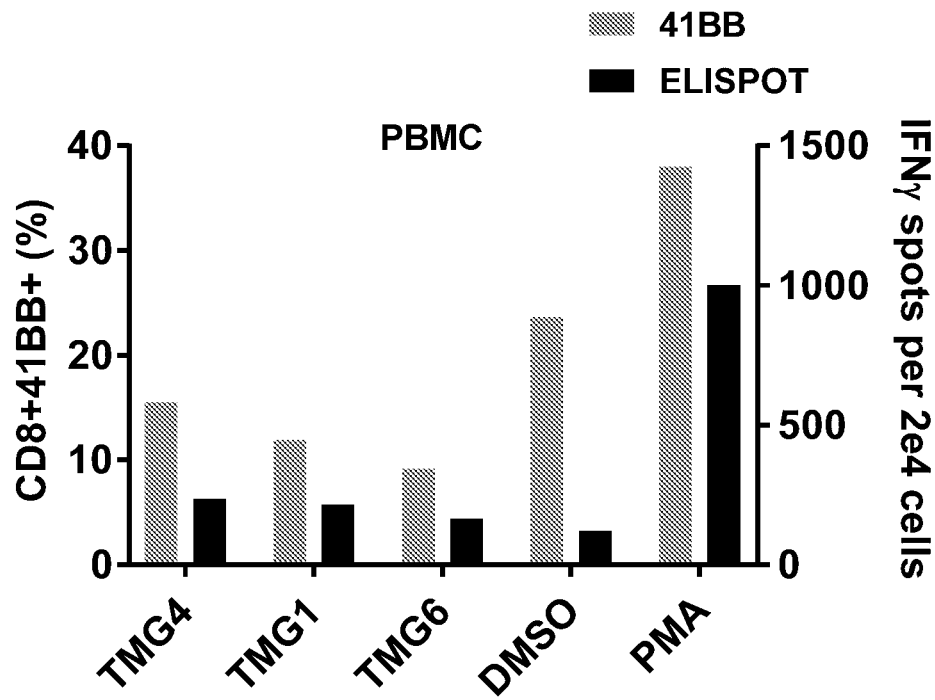

The SMAD5$^{P268inPKH}$-reactive cells were FACS-purified from Pt. 4213 TIL and memory cells and single-cell RT-PCR (scPCR) was performed to identify their TCR-Vβ and TCR-Vα sequences (Pasetto et al., Cancer Immunol. Res., 4: 734-743 (2016)). Analysis of the TCR sequences revealed that the SMAD5$^{P268inPKH}$-reactive TIL and IVS-derived memory cells shared matching TCR-Vβ and TCR-Vα sequences (Tables 2-3). Table 2 provides the TCR-VB sequences of neoantigen reactive TIL. Table 3 provides the PBL derived TCR-VB sequences of cloned TCRs. Genetically engineered autologous peripheral blood T cells expressing the SMAD5$^{P268inPKH}$-reactive TCR (Table 3) conferred that the selective reactivity of the TCR against the mutated SMAD5$^{P268inPKH}$ peptide is restricted by HLA*B08:01 (FIG. 5F, 5G). Thus, using IVS of memory T cells can lead to the identification and enrichment of neoantigen-reactive T cells.

TABLE 2

| Hist-ology | Patient | Target Neo-antigen | TIL pheno-type | TCR-VB CDR3 sequence |
|---|---|---|---|---|
| Colon | 4213 | DDX1 | CD8 | CASGVAESSYEQYF SEQ ID NO: 2 |
| | | SMAD5 | CD8 | CASGLVSGQGAGVTEAFF SEQ ID NO: 3 |

TABLE 2-continued

| Hist-ology | Patient | Target Neo-antigen | TIL pheno-type | TCR-VB CDR3 sequence |
|---|---|---|---|---|
| Ovarian | 4046 | USPX | CD4 | CASSSGTSADTQYF SEQ ID NO: 4 |
| NSCLC | 4134 | GRB7 | CD8 | CASSQGSYEQYF SEQ ID NO: 5 |
| Endo-metrial | 4148 | KRAS$^{G12V}$ | CD4 | CSAREGAGGMGTQYF SEQ ID NO: 6 |

TABLE 3

| Histology | Patient | Target Neoantigen | CD4/CD8 | CDR3β sequence |
|---|---|---|---|---|
| Colon | 4213 | SMAD5 | CD8 | CVSGLVSGQGAGVTEAFF SEQ ID NO: 7 |
| Endo-metrial | 4148 | KRA5$^{G12V}$ | CD8 | CASSLTSGGFDEQFF SEQ ID NO: 8 |
| Rectal cancer | 4171 | KRAS$^{G12D}$ | CD4 | CASSVTGGSYPNTEAFF SEQ ID NO: 9 |
| Sigmoid colon adeno-carcinoma | 4238 | KRAS$^{G12D}$ | CD4 | CASSEALSGGAFGGELFF SEQ ID NO: 10 CASSENLAGAANTGELFF SEQ ID NO: 11 CASSLQGAMNTEAFF SEQ ID NO: 12 CASSVSLTQYGYTF SEQ ID NO: 13 CSVDERGGTHGYTF SEQ ID NO: 14 CSALGGGNTGELFF SEQ ID NO: 15 |

EXAMPLE 4

This example demonstrates the isolation of T cells targeting shared oncogenic mutations from peripheral blood of epethelial cancer patients.

Due to tumor heterogeneity and differential expression of non-synonymous mutations in cancer cells, targeting mutated driver mutations that apear to be homogenously expressed in cancer cells can target cancer cells more efficiently. Therefore, it was sought to determine whether T cells targeting shared oncogenic mutations can be isolated using the approach of Example 3. A focus on hot-spot mutations in the proto-oncogene KRAS, which are shared at high frequencies across multiple cancers histologies (Hruban et al., Am. J. Pathol., 143: 545-54 (1993); Russo et al., Cancer, 120: 1482-90 (2014)), was chosen.

Figure 6A:
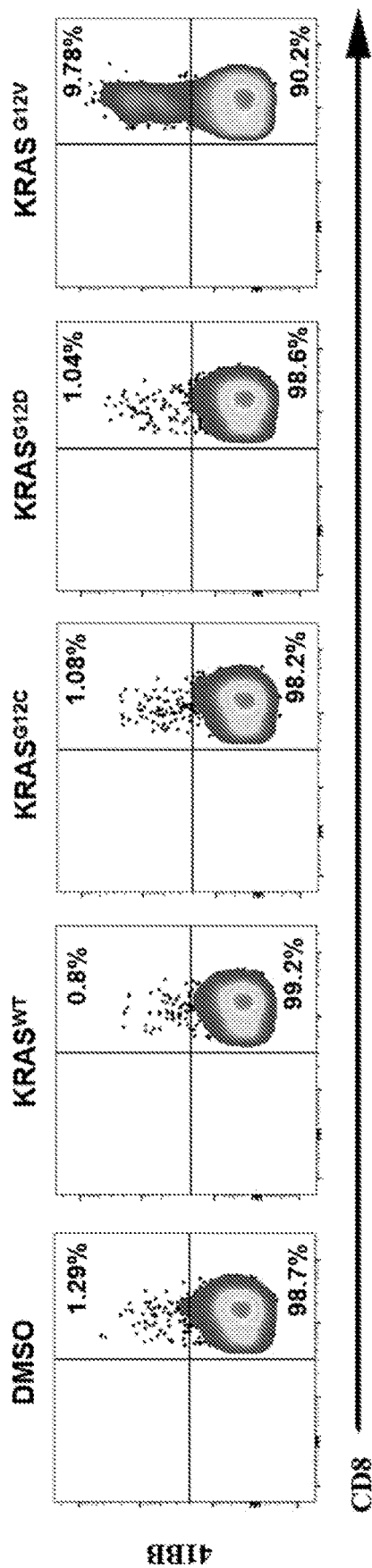
FIG. 6A shows FACS plots showing the percentages of cells expressing CD8 and 41BB after 41BB-enriched CD8 memory T cells were expanded, and their reactivity was tested against autologous DCs pulsed with the indicated peptides.
Figure 6B:
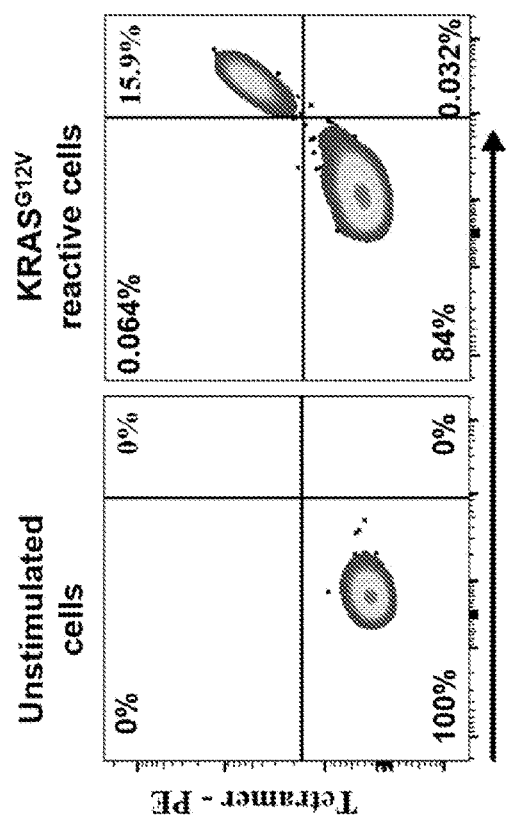
FIG. 6B shows FACS plots showing the percentages of 41BB-enriched CD8 memory T cells stained with $KRAS^{G12V}$ 9-mer tetramers; unstimulated CD8 cells were used as control (left).
Figure 6C:
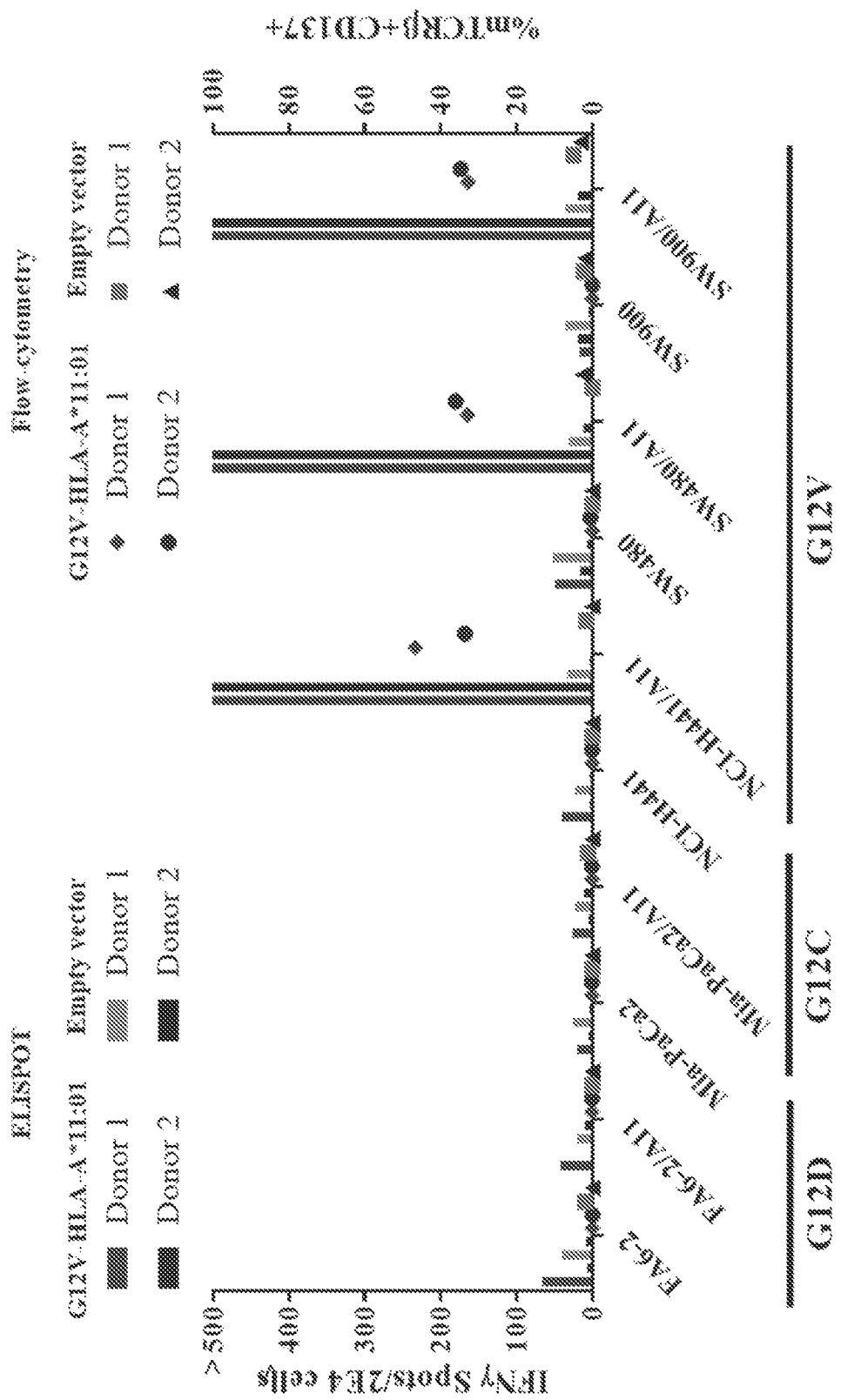
FIG. 6C is a graph showing the number of IFNγ spots per 2e4 cells and the percentage of mTCRβ+41bb+ cells measured following a 41BB upregulation and ELISPOT IFNγ secretion assay of TCR-transduced allogeneic T cells. T cells were co-cultured with cell lines naturally expressing G12 mutations ±HLA-A11 transduction.
Figure 6D:
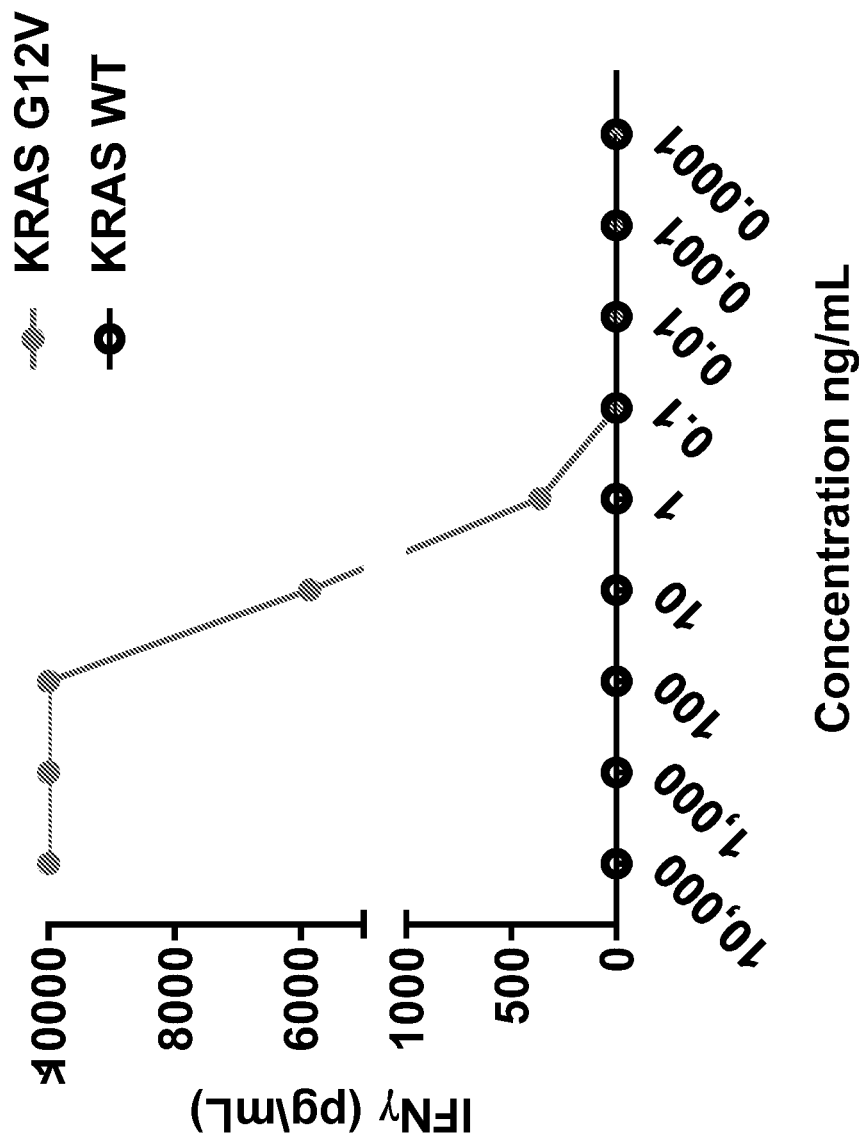
FIG. 6D is a graph showing the IFNγ secretion (pg/mL) of TCR-transduced cells following coulture with autologous DCs pulsed with the indicated concentrations of mutated and WT 9-mers. A representative of at least three experiments.
Figure 6E:
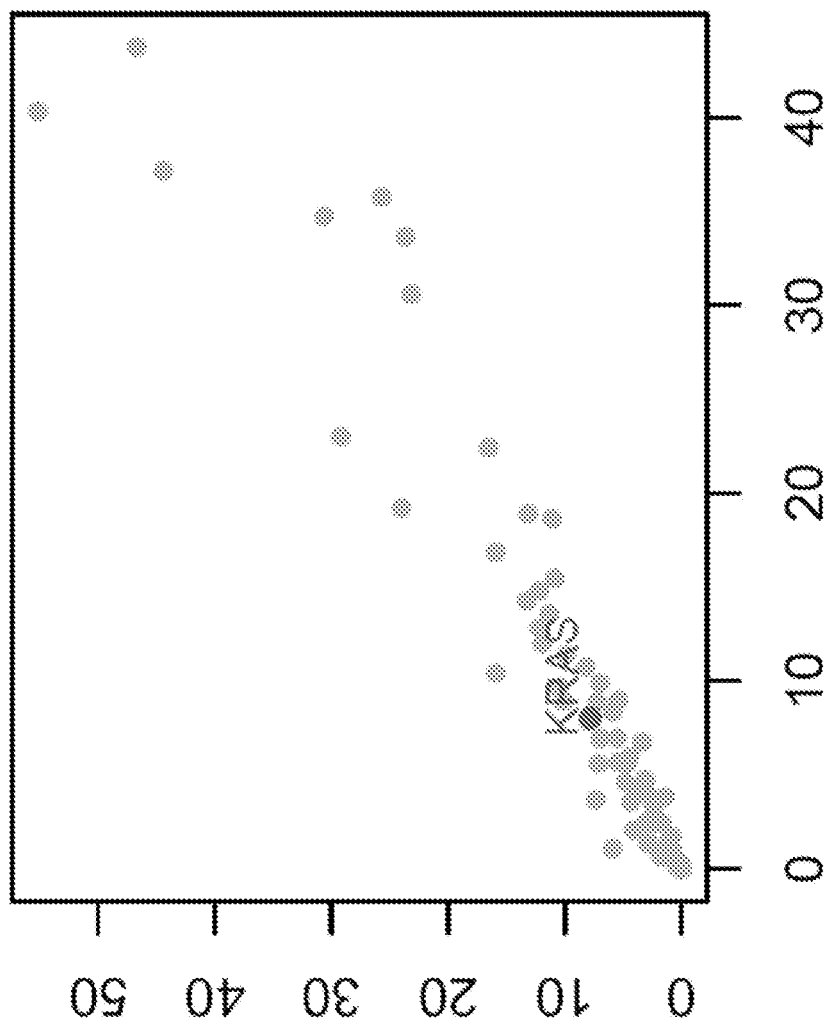
FIG. 6E is a graph showing shared $KRAS^{G12V}$ expression in two excised lesions from Pt.4148. RNAseq showing shared mutations between two excised tumors, KRAS mutated transcript is present in both excised lesions at the same levels, FPKM=~8.5.
Figure 6F:
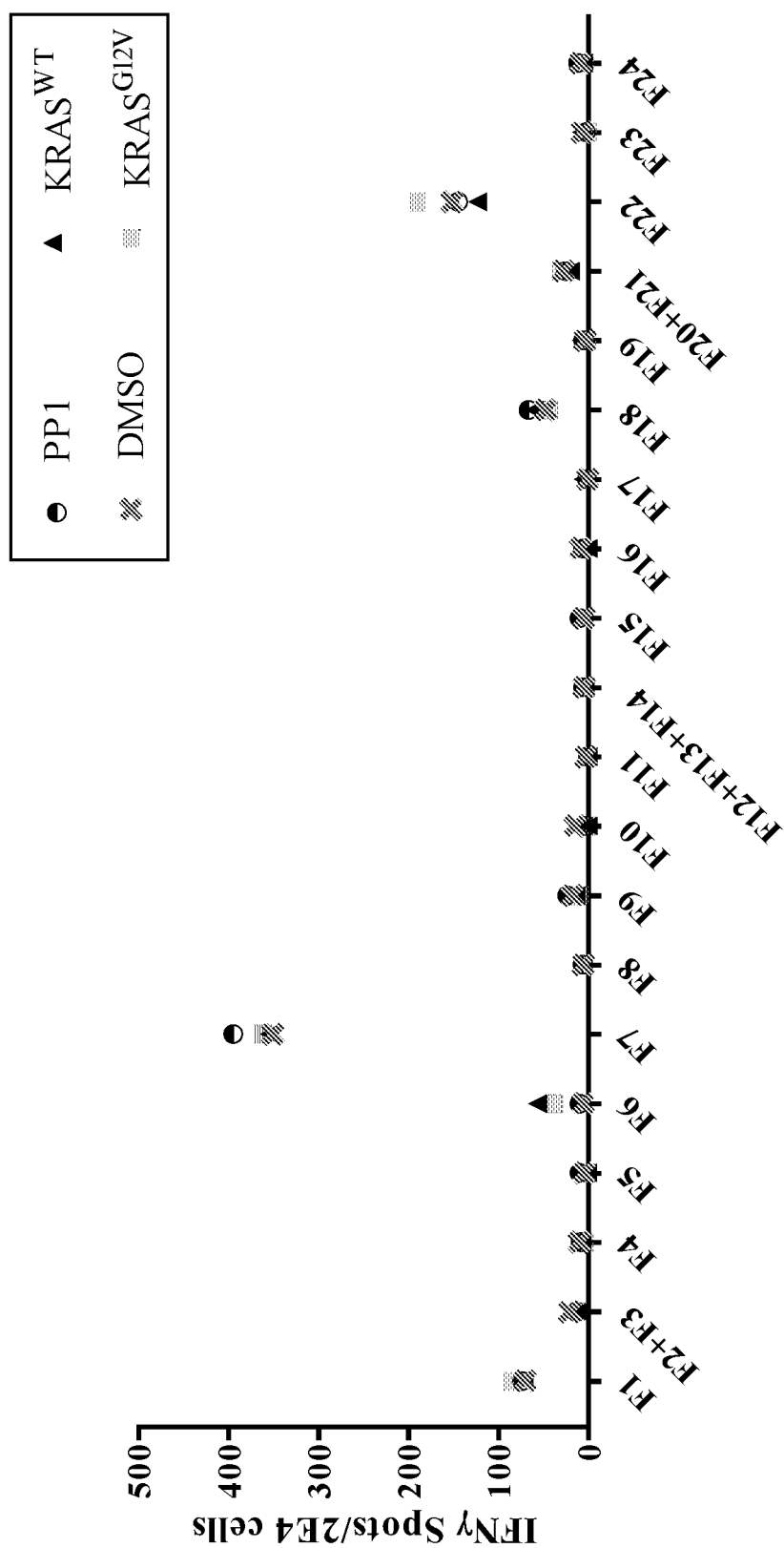
FIG. 6F is a graph showing the number of IFNγ spots per 2e4 cells after TIL fragments from Pt. 4148 were grown ex vivo following tumor excision and co-cultured with autologous DCs pulsed with $KRAS^{G12V}$ and $KRAS^{WT}$ and IFNγ secretion was assessed by ELISPOT. TIL fragments from Pt.4148 did not show reactivity against $KRAS^{G12V}$.

To test the use of the approach of Example 3 across multiple epithelial cancer types, IVS of memory, $T_N$, and bulk PBL from a metastatic endometrial cancer patient (Pt. 4148) was performed using a mixture of KRAS$^{G12V}$, KRAS$^{G12C}$, and KRAS$^{G12D}$ 24-mer peptides, followed by 4-1BB enrichment. Exome and RNA analysis of Pt. 4148 tumor showed expression only of the KRAS$^{G12V}$ mutation (FIG. 6E). No TILs reactive against the KRAS$^{G12V}$ were identified in the initial screen performed in the laboratory (FIG. 6F).

To identify T cells targeting mutated KRAS, enriched memory, T$_N$, and PBL cells were co-cultured with autologous DCs pulsed with the individual KRAS$^{G12}$ mutated LPs. As shown in FIG. 6A, memory CD8+ T cells showed selective reactivity against KRAS$^{G12V}$ LP. T$_N$ and bulk PBL were not reactive against any of the KRAS peptides. Following co-culture with DCs pulsed with mutated peptides, memory T cells recognizing the mutated peptides were FACS-sorted into 96-well PCR plates for scPCR based on T-cell activation markers. 11 unique TRBV and 13 TRAV were obtained (Table 4).

TABLE 4

| TCR | CDR3β | | CDR3α |
|---|---|---|---|
| TCR1 | CASRGTEGTEAFF SEQ ID NO: 29 | TRBV9-1 | TRAV8-1 |
| TCR2 | CASSEALSGGAFGGELFF SEQ ID NO: 30 | TRBV6-1 | TRAV41-1 |
| TCR3 | CASSENLAGAANTGELFF SEQ ID NO: 31 | TRBV6-1 | TRAV41-1 |
| TCR4 | CASSLQGAMNTEAFF SEQ ID NO: 32 | TRBV5-4 | TRAV38-2 |
| TCR5 | CASSPRTGGTTIGEQFF SEQ ID NO: 33 | TRBV19 | TRAV3-1 |
| TCR6α1 TCR6α2 | CASSVSLTQYGYTF SEQ ID NO: 34 | TRBV9-1 | TRAV12-2 |
| TCR7 | CAWSRGGNQPQHF SEQ ID NO: 35 | TRBV30-1 | TRAV23 |
| TCR8 | CASSNSGAAVDTDTQYF SEQ ID NO: 36 | TRBV5-1 | TRAV8-3 |
| TCR9 | CSVDERGGTHGYTF SEQ ID NO: 37 | TRBV29-1 | TRAV12-2 |
| TCR10 | CASSRGLATTDTQYF SEQ ID NO: 38 | TRBV7-7 | TRAV4 |
| TCR11α1 TCR11α2 | CSALGGGNTGELFF SEQ ID NO: 39 | TRBV20-1 | TRAV1-1 |

Since Pt. 4148 expressed HLA-A*11:01, which is predicted to bind KRAS$^{G12V}$ 9-mer, it was presumed that staining the cells with A*11-9-mer tetramers could address whether HLA-A*11:01 is the correct restriction element. Indeed, HLA-A*11:01-9-mer tetramers bound 15.9% of the memory CD8 cells in the culture (FIG. 6B).

Sorting the tetramer-positive cells and sequencing their TCR revealed single TCRα and TCRβ chains (Table 5). To further test the TCR, the TRAV and TRBV were synthesized, cloned and retrovirally-transduced into allogeneic PBLs, as previously described (Tran et al., Science, 350: 1387-90 (2015); Gros et al., Nat. Med., 22(4):433-8 (2016)). To evaluate the specificity and the potency of the TCR, the TCR-transduced PBLs were co-cultured with cancer cell lines harboring KRAS$^{G12V}$ mutations with or without transfection with HLA-A*11:01 (FIG. 6C) or with autologous DCs pulsed with a serial dilution of the mutated 9-mer and wild-type peptides (FIG. 6D). The results showed that the isolated TCR selectively recognized the KRAS G12V mutation presented on HLA-A*11:01. Due to the high prevalence of KRAS$^{G12V}$ expression across cancers and HLA-A*11:01 allele frequencies in selected populations (14% in U.S. Caucasians and 23% in Asian-Americans) (The Allele Frequency Net Database, available at: allelefrequencies.net/hla6006a.asp (accessed: 30th March 2018)), this TCR could potentially be used as an "off-the-shelf" reagent to treat thousands of relevant cancer patients per year.

TABLE 5

| Histology | Patient | Target Neoantigen | CD4/ CD8 | CDR3β sequence |
|---|---|---|---|---|
| Colon | 4213 | SMAD5 | CD8 | CVSGLVSGQGAGV TEAFF SEQ ID NO: 16 |
| Endo-metrial | 4148 | KRAS$^{G12V}$ | CD8 | CASSLTSGGFDEQ FF SEQ ID NO: 17 |
| Rectal cancer | 4171 | KRAS$^{G12D}$ | CD4 | CASSVTGGSYPNT EAFF SEQ ID NO: 18 |
| Sigmoid colon adeno-carcinoma | 4238 | KRAS$^{G12D}$ | CD4 | CASSEALSGGAFG GELFF SEQ ID NO: 19 CASSENLAGAANT GELFF SEQ ID NO: 20 CASSLQGAMNTEA FF SEQ ID NO: 21 CASSVSLTQYGYT F SEQ ID NO: 22 CSVDERGGTHGYT F SEQ ID NO: 23 CSALGGGNTGELF F SEQ ID NO: 24 |

Figure 7A:
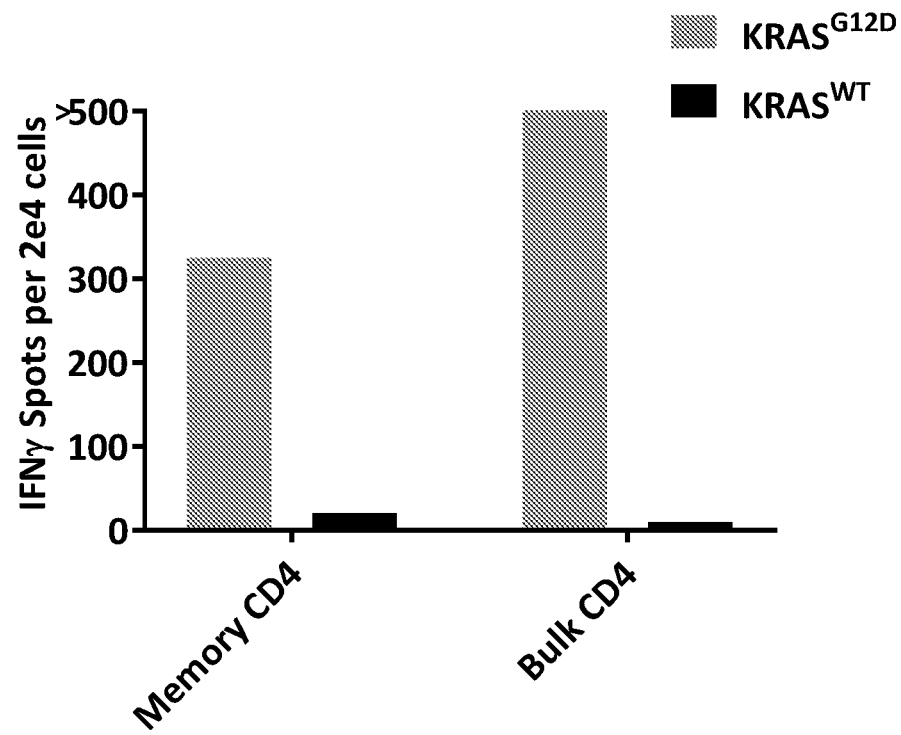
FIG. 7A is a graph showing the number of IFNγ spots per 2e4 cells measured in an IFNγ-ELISPOT assay of 41BB+ and/or OX40+enriched CD4 subsets co-cultured with autologous DCs pulsed with mutated and wild-type KRAS peptides.
Figure 9:
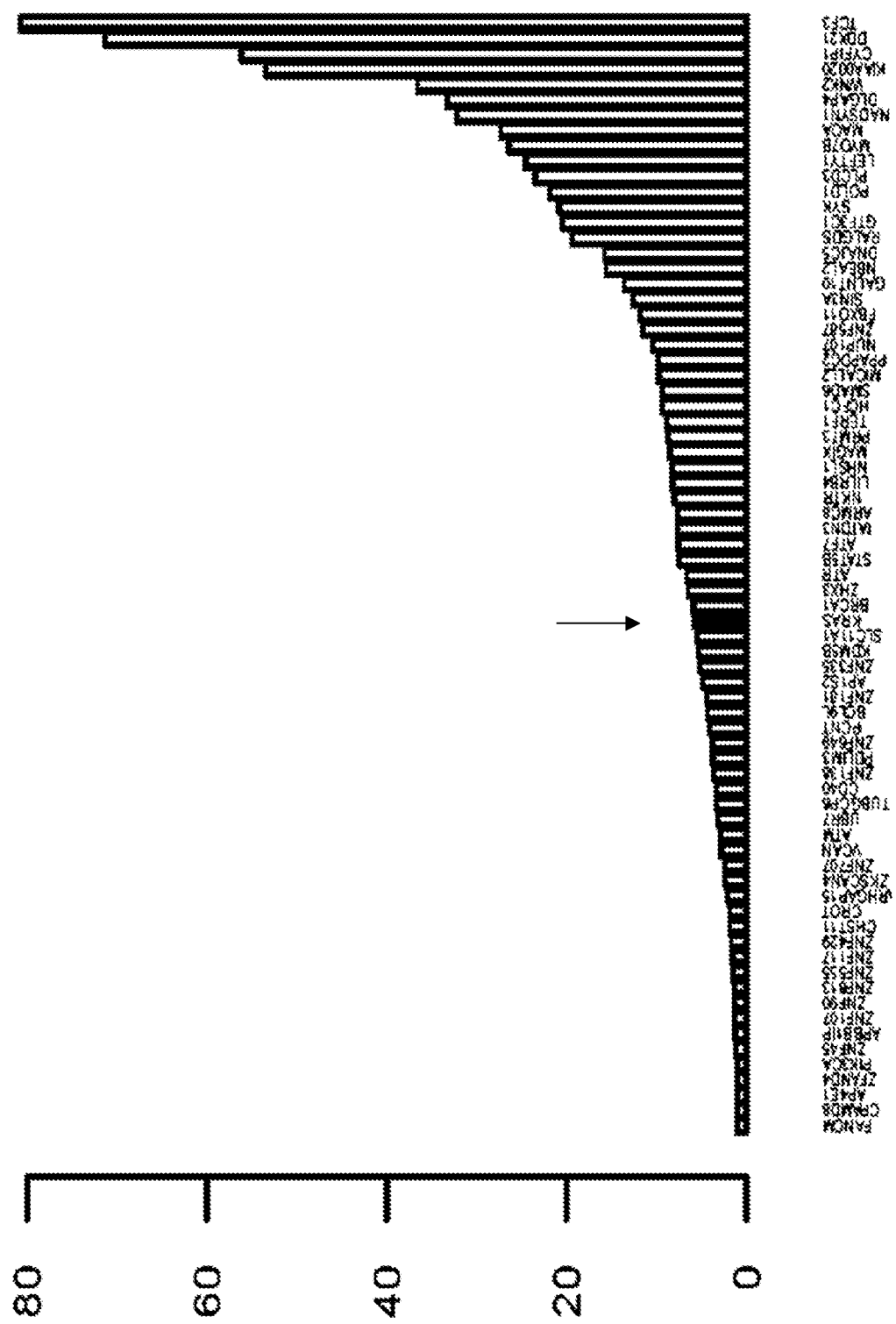
FIG. 9 is a graph showing $KRAS^{G12D}$ expression in excised lesions from Pt.4171. Representative RNAseq of nonsynonymous mutations transcripts detected in excised metastatic tumor from patient Pt.4171 is shown. $KRAS^{G12D}$ transcript is shown by arrow.

Next, the approach of Example 3 was applied to identify and isolate TCRs targeting additional mutated KRAS neoepitopes. To that end, T cell subsets from PBL of a metastatic rectal cancer patient (Pt. 4171) were stimulated. Exome and RNA analysis of Pt. 4171 tumor showed expression only of the KRAS$^{G12D}$ mutation (FIG. 9). The PBL were stimulated using KRAS$^{G12D}$ full-length RNA or 24-mer peptide following ten days of IVS. The T cell subsets were re-stimulated, FACS-sorted based on T-cell activation markers, and the numbers of cells were further expanded. Enriched cells were further tested for recognition of KRAS$^{G12D}$. Both memory and bulk sorted, CD4+ cells showed specific recognition of KRAS$^{G12D}$ 24-mer peptide-pulsed on autologous DCs (FIG. 7A).

To isolate the reactive TCR, an 18 hr co-culture of these subsets with autologous DCs pulsed with the mutated peptide was performed. T cells that upregulated activation markers (OX40+, 4-1BB+ or OX40+4-1BB+ double positive) were sorted into a 96-well PCR plate for scPCR (Pasetto et al., Cancer Immunol. Res., 4: 734-743 (2016)). The subsets shared one TCR (TCR1), however, in the memory subset the sequencing revealed two additional TCRs (Table 6). The TRBV sequences of 41BB+-sorted T cells following co-culture with DCs pulsed with KRAS$^{G12D}$ peptide are shown in Table 6.

Figure 7B:
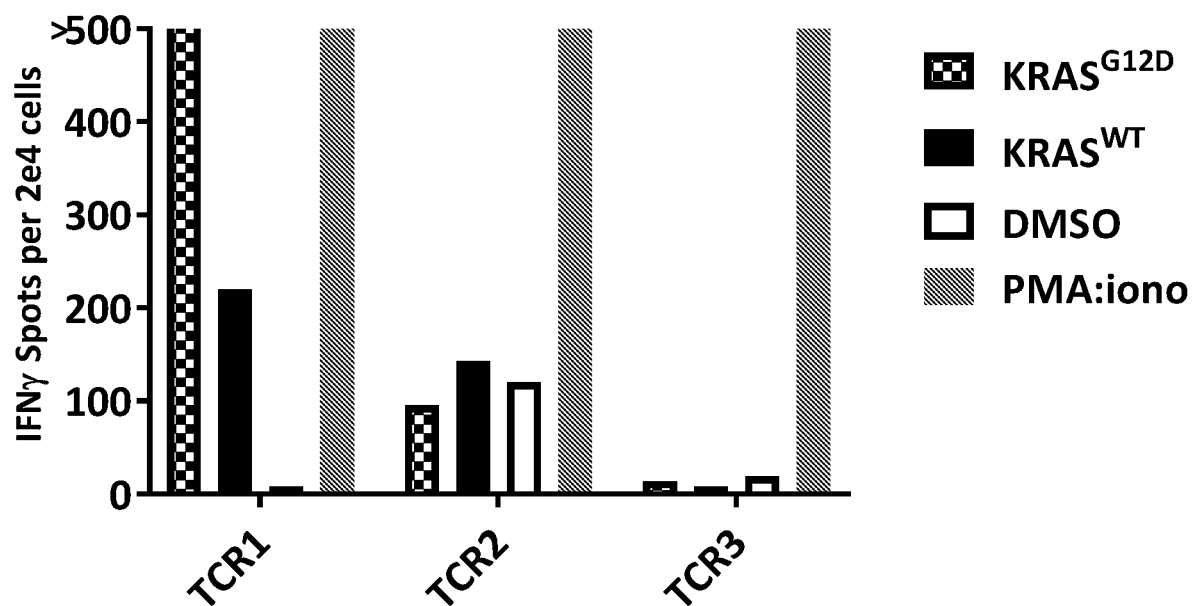
FIG. 7B is a graph showing the number of IFNγ spots per 2e4 cells measured after retrovirally transduced allogeneic PBLs expressing the indicated TCRs were co-cultured with autologous DCs pulsed with either $KRAS^{G12D}$ or $KRAS^{WT}$. Representative of at least two experiments.
Figure 7C:
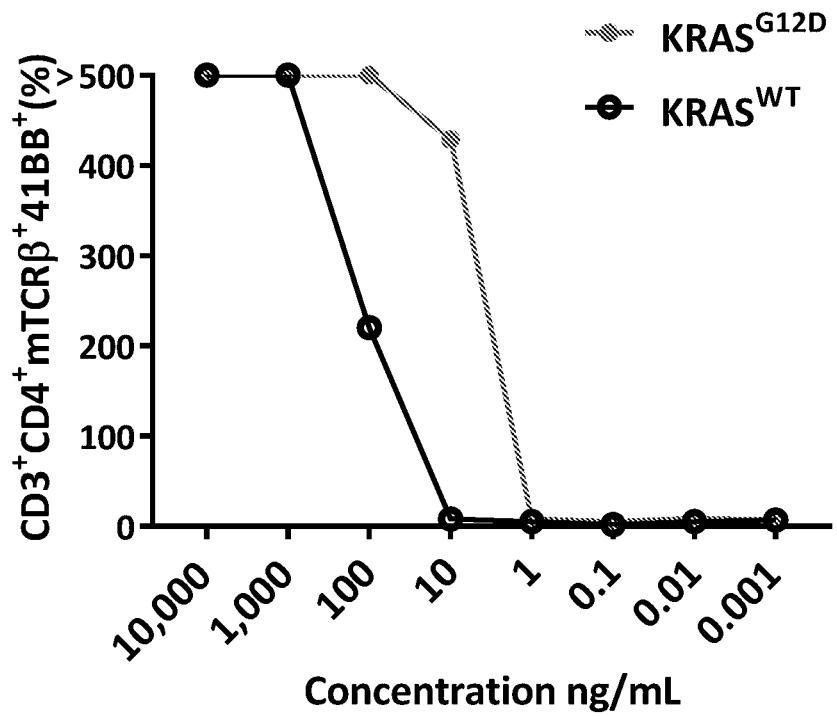
FIG. 7C is a graph showing the percentage of CD3+CD4+ mTCRβ+41BB+ cells measured after TCR1-transduced PBLs were co-cultured with DCs pulsed with a serial dilution of G12D or WT peptides. Representative of at least two experiments.
Figure 7D:
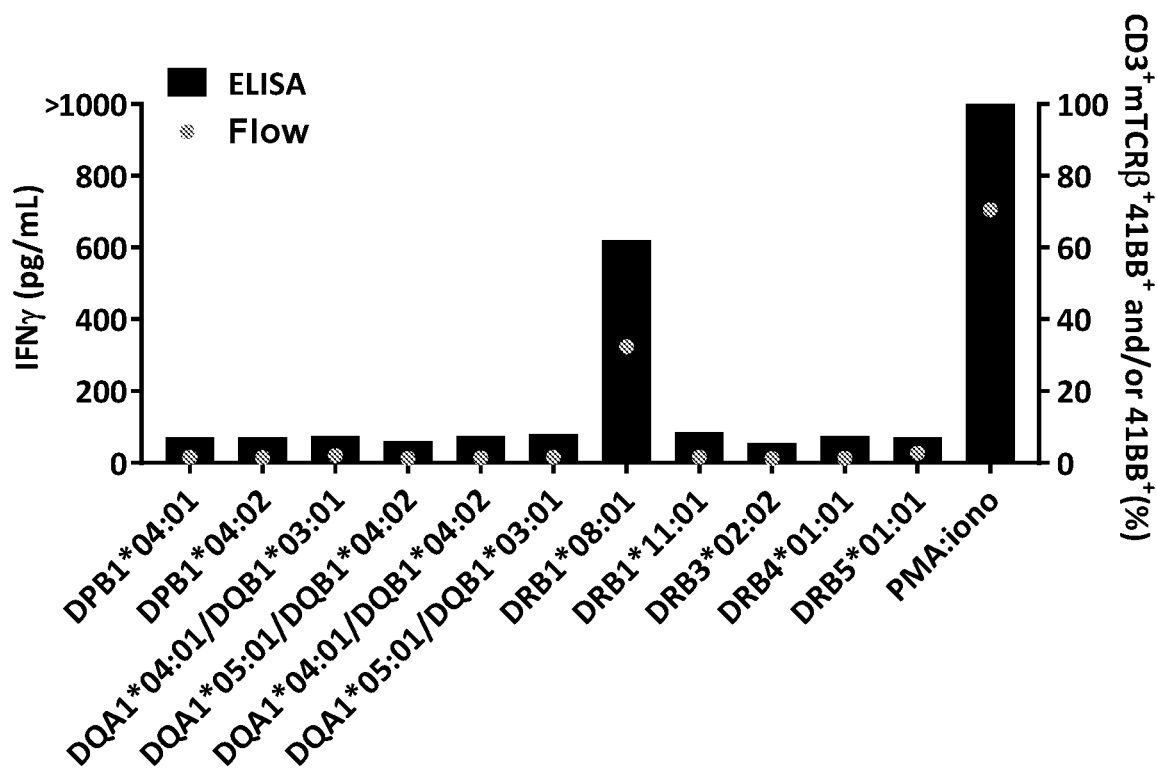
FIG. 7D is a graph showing the concentration of IFNγ secreted (pg/mL) and the percentage of CD3+mTCRβ+ 41BB+ cells measured after COST cells were transfected with patient's class II HLA and co-cultured with TCR1-transduced cells. Reactivity was determined by IFNγ ELISA and the upregulation of 41BB surface marker. Representative of at least two experiments

The TCRs were constructed, cloned and retrovirally transduced into allogeneic PBLs. Only TCR1, which was present in both sorted subsets, showed specific reactivity against the G12D peptide (FIG. 7B). Next, the specificity and avidity of the TCR against DCs pulsed with a serial dilution of mutated and wild-type KRAS peptides was evalulated (FIG. 7C). It was determined that TCR recognition was restricted by HLA-DRB1*08:01 (FIG. 7D).

TABLE 6

| | | | CDR3β |
|---|---|---|---|
| Memory | TCR1 | TRBV9*01 | CASSVTGGSYPNTEAFF SEQ ID NO: 25 |
| | TCR2 | TRBV6-2*01 | CASSGPGETQYF SEQ ID NO: 26 |
| | TCR3 | TRBV5-1*01 | CASSLAKGPGNTEAFF SEQ ID NO: 27 |
| Bulk | TCR1 | TRBV9*01 | CASSVTGGSYPNTEAFF SEQ ID NO: 28 |

In summary, the IVS approach was employed on T cell PBL subsets from 6 metastatic cancer patients that harbored KRAS mutation in their tumor. In three, TCRs targeting KRAS mutation were able to be isolated from their memory cells (Pt. 4148, Pt. 4171, and Pt.4238 presented in FIGS. 6A-6N, FIGS. 7A-7D, and Table 7, respectively). In Pt. 4171 PBLs, the reactive TCR was isolated from bulk CD4+ cells as well; however, none of the reactive TCRs were detected in the naïve subset.

TABLE 7

| | | Detected in | | |
|---|---|---|---|---|
| Patient | Neoantigen | Memory | Naïve | Bulk PBMC |
| 4213 | SMAD5$^{P268inPKH}$ | ✓ | X | X |
| 4217 | MUC4$^{R4435S}$ | ✓ | X | X |
| 4171 | KRAS$^{G12D}$ | ✓ | X | ✓ * |
| 4148 | KRAS$^{G12V}$ | ✓ | X | X |
| 4238 | KRAS$^{G12D}$ | ✓ | X | X |

* KRAS$^{G12D}$-reactive TCR detected in sorted bulk CD4+. Identical to TCR isolated from the memory CD4+ subset.

EXAMPLE 5

This example demonstrates the isolation of T cells (and TCRs) targeting KRAS G12D from the peripheral blood of patient 4238.

The IVS approach of Example 3 was employed on PBLs from 6 metastatic cancer patients harboring KRAS non-synonymous mutations in their tumors. Reactive T cells targeting KRAS mutations from PBLs from three patients, Pt.4148, Pt.4171, and Pt.4238, were able to be detected and isolated. The reactivities detected in the memory T subsets from the first two patients are presented in FIGS. 6A-6F and FIGS. 7A-7D.

Figure 6G:
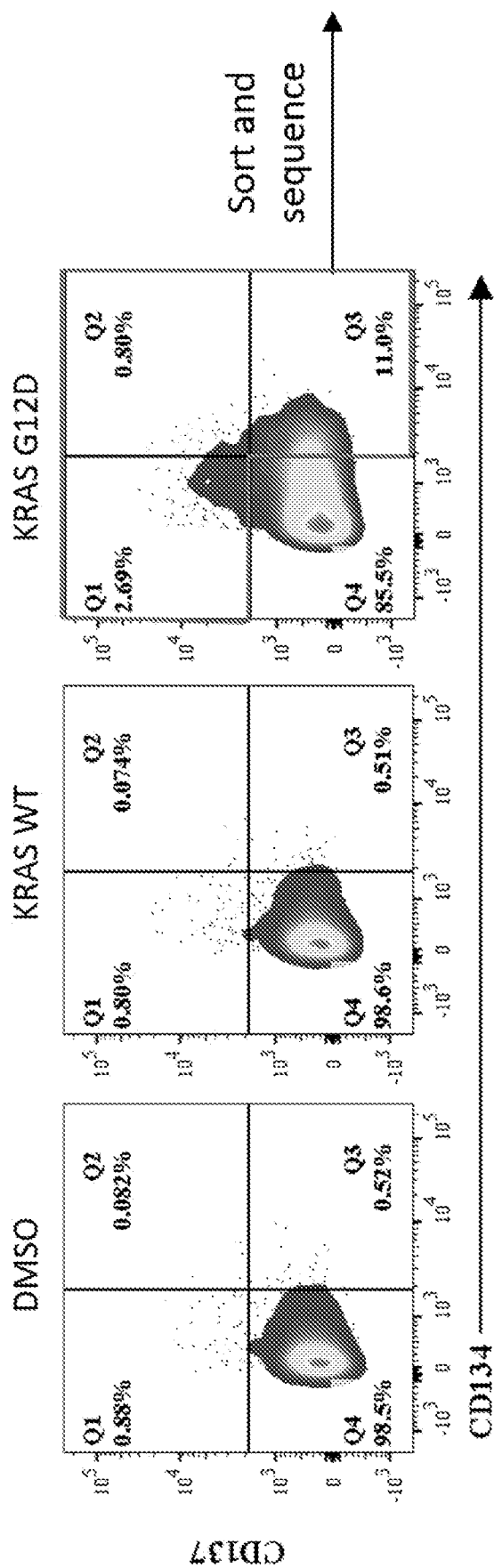
FIG. 6G shows FACS plots showing the upregulation of T-cell activation markers of 4-1BB+ and/or OX40+-enriched CD4 memory T cells following co-incubation with autologous DCs pulsed with mutated and WT 24-mer peptides.
Figure 6H:
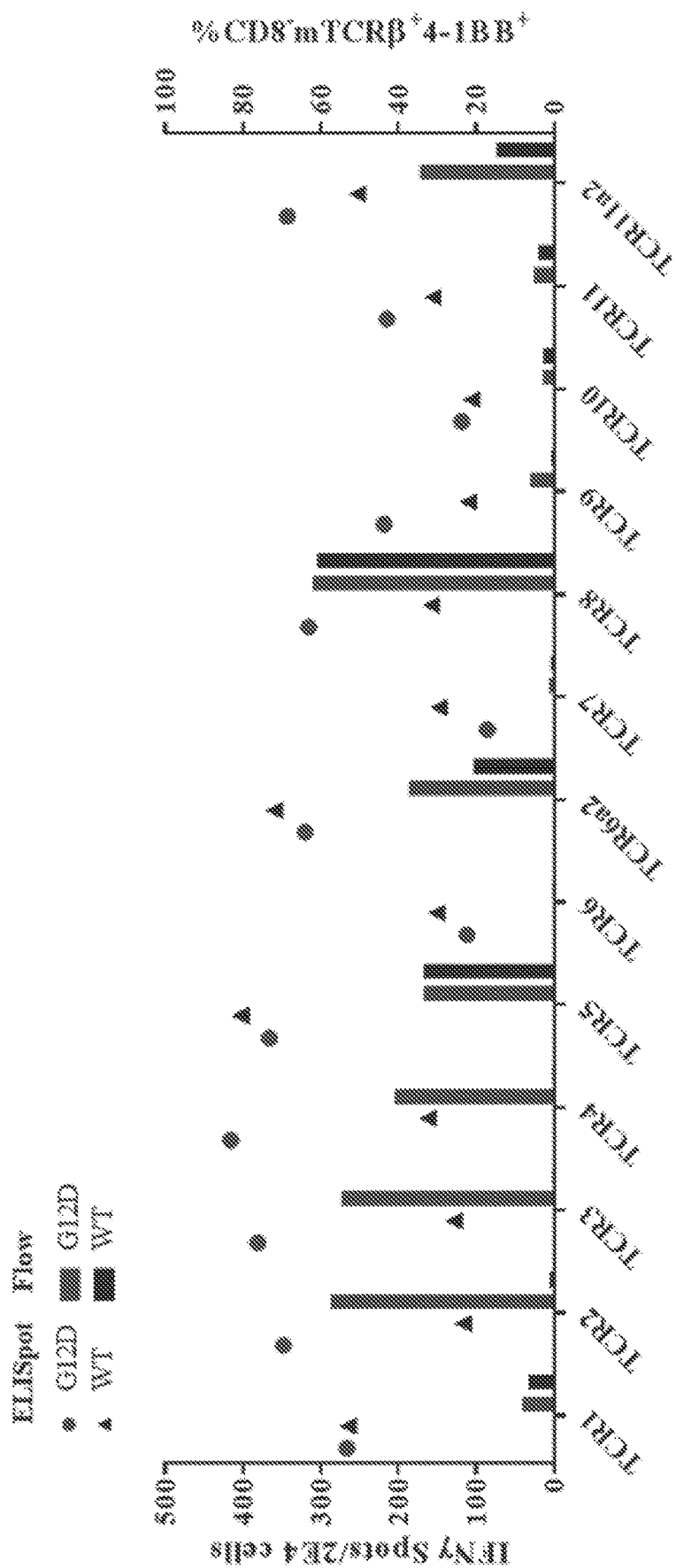
FIG. 6H is a graph showing the number of IFNγ spots per 2e4 cells and the percentage of CD8+mTCRβ+41BB+ cells measured by an IFNγ-secretion ELISPOT assay of retrovirally-transduced allogeneic PBMCs following co-incubation with DCs pulsed with mutated and WT peptides.
Figure 6I:
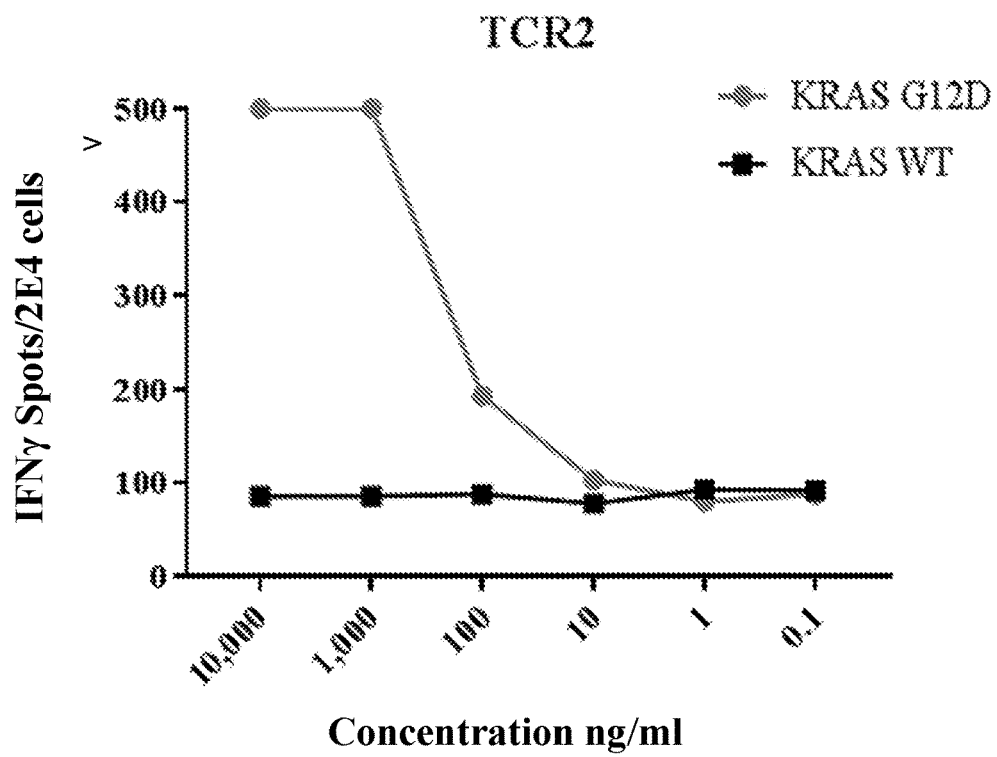
FIGS. 6I-6N are graphs showing the IFNγ secretion of cells transduced with TCR2 (I), TCR3 (J), TCR4 (K), TCR6α2 (L), TCR9 (M), or TCR11α2 (N) co-incubated for 18 hrs with autologous DCs pulsed with the indicated concentrations of mutated and WT peptide. Representative results of at least 3 experiments.
Figure 6J:
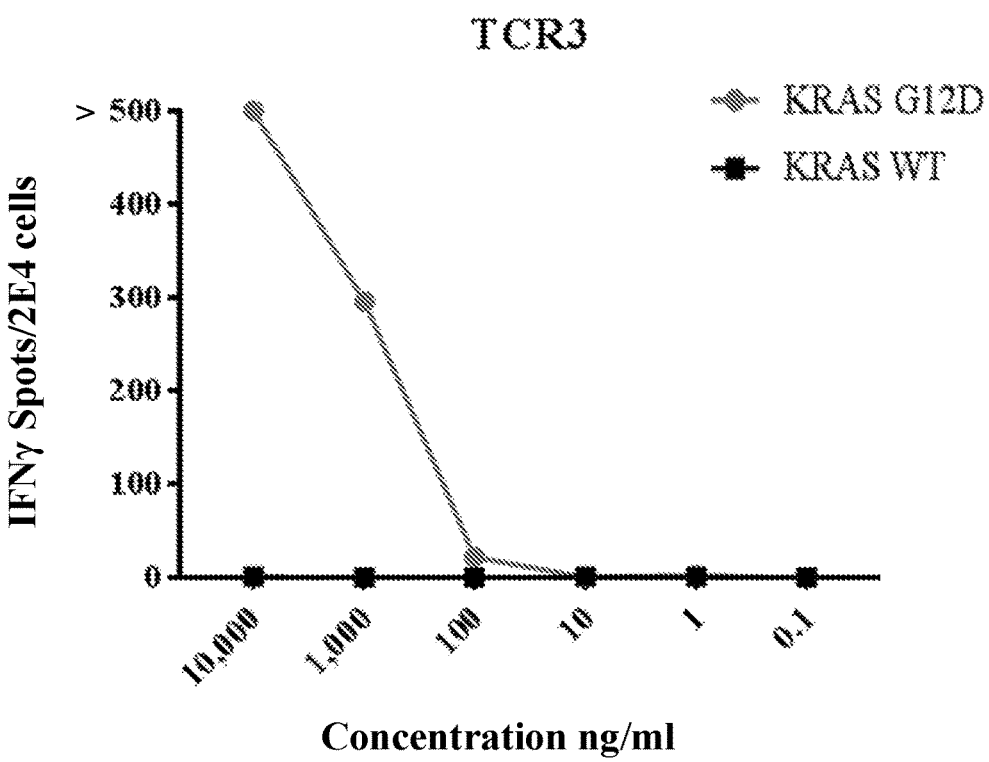
Figure 6K:
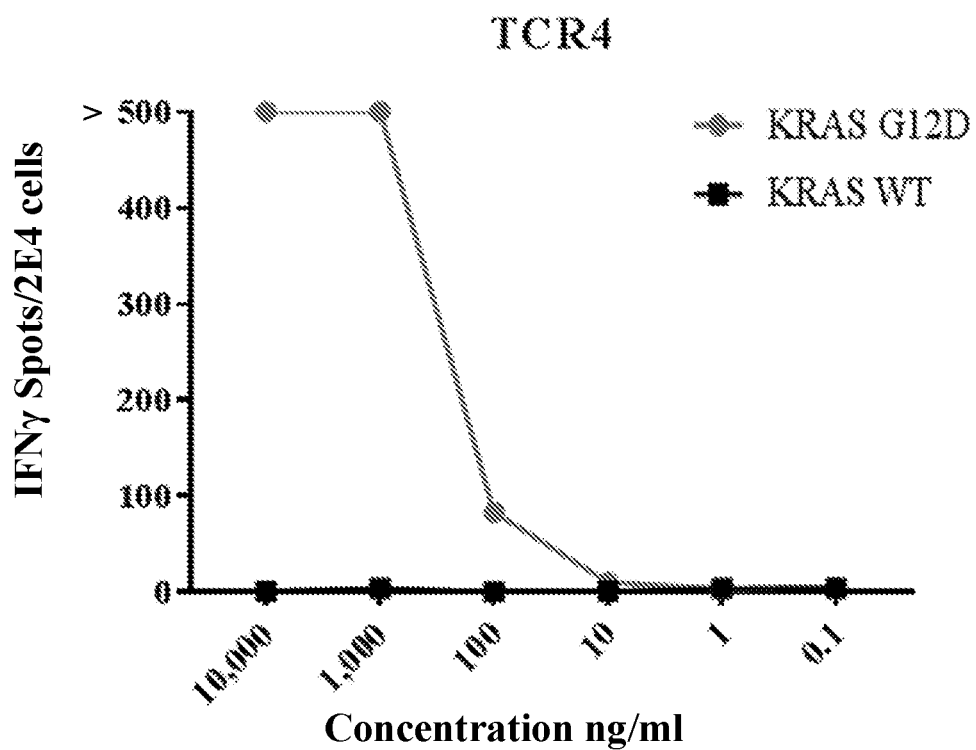
Figure 6L:
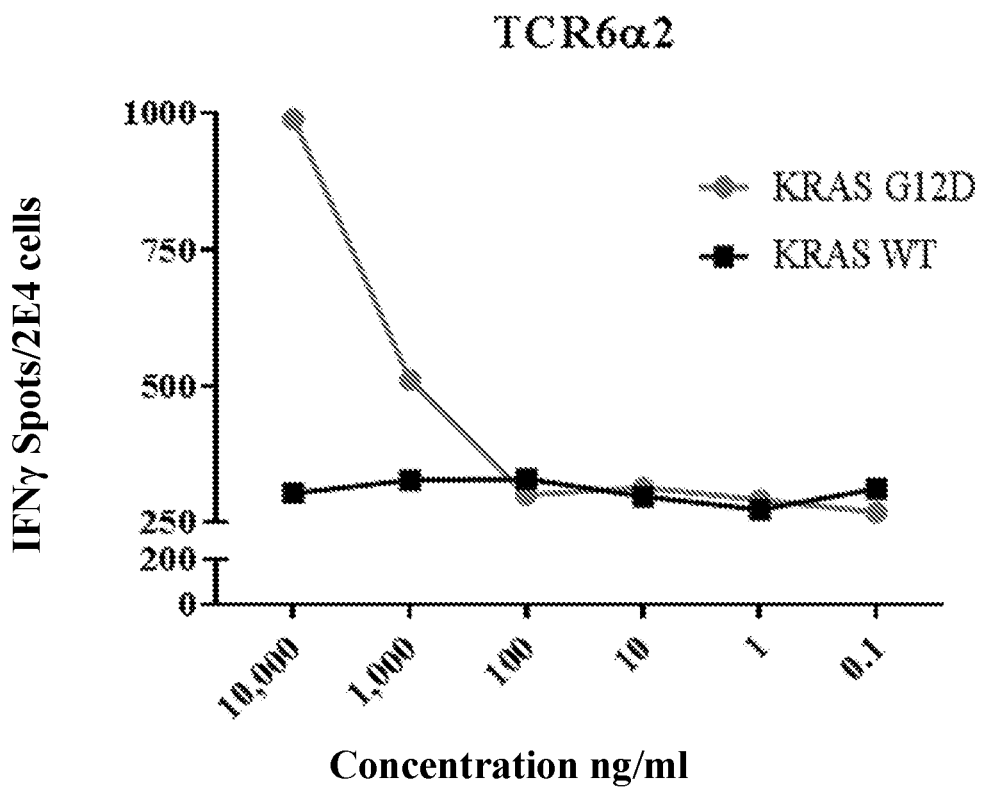
Figure 6M:
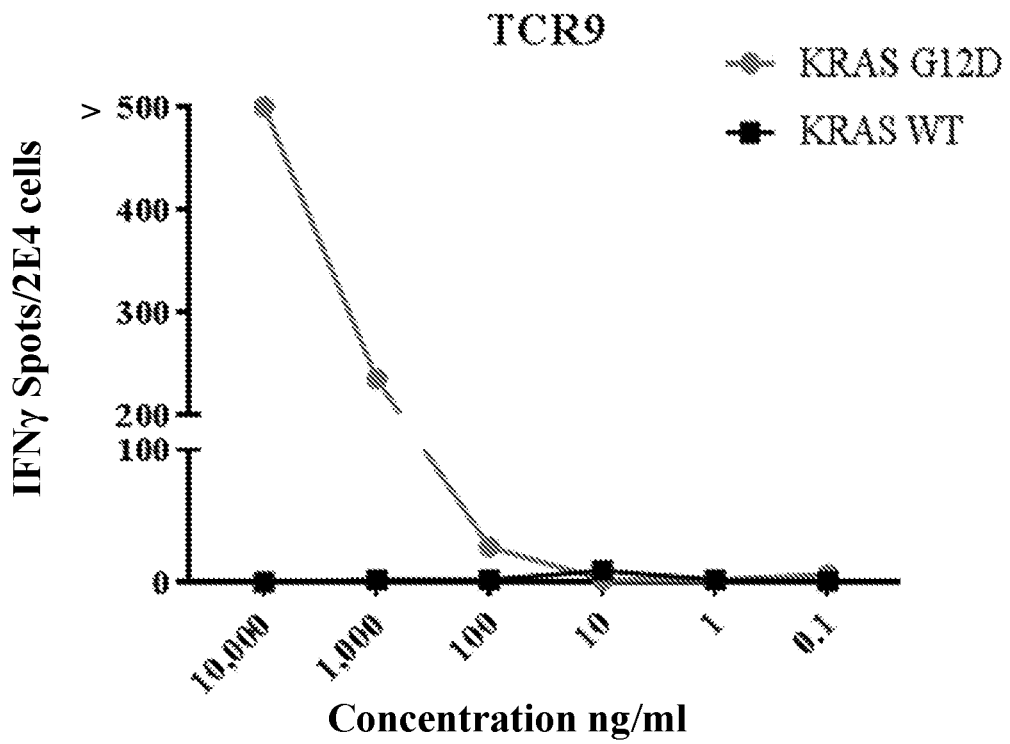
Figure 6N:
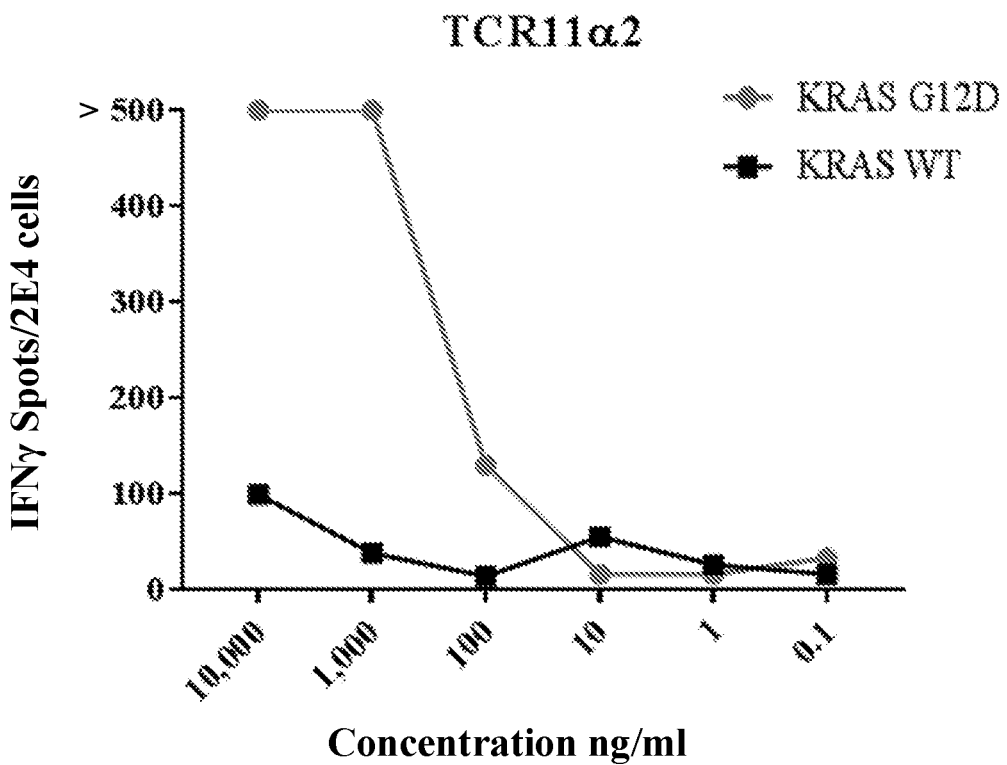

Utilizing the IVS approach on apheresis samples from Pt. 4238, a metastatic sigmoid colon adenocarcinoma patient harboring a G12D mutation in the excised tumor, enabled the detection and isolation of 6 TCRs targeting KRAS$^{G12D}$ (FIGS. 6G-6N). Briefly, apheresis vials were thawed, rested overnight and sorted into CD4 and CD8 naïve, memory, and bulk subsets, six populations in total. Following, T cell subsets were stimulated for ten days with KRAS$^{G12D}$ 24-mer, as described in the methods. At day ten the cells were co-cultured with autologous DCs pulsed with the peptide, at 3:1 T cells:DC ratio, and 4-1BB+ and/or OX40+ were sorted the next day. Sorted cells were expanded in REP protocol for 14 days and stimulated populations reactivities were tested in a co-culture assay in the presence of DCs that were pulsed with the 24-mer mutated peptide. While no reactivity was observed in the bulk and naïve subsets, a CD4 reactivity was detected in the memory population against the mutated but not the wild-type KRAS peptide (FIG. 6G). To isolate reactive TCRs memory CD4 cells upregulating T-cell activation markers were sorted, following co-culture with DCs pulsed with the mutated peptide, and scPCR and nested Sanger sequencing were performed for the TCRs (Table 4). Based on the sequencing results 13 TCRs were synthesized, cloned and retrovirally transduced into allogeneic PBLs from a healthy donor. Following, to test the reactivity and the specificity of the TCRs, the TCR-transduced cells were incubated with DCs pulsed with 10 μg/ml of either the mutated KRAS or its counterpart WT peptide. Six TCRs, (TCR2, TCR3, TCR4, TCR6α2, TCR9, and TCR11α2) showed selective reactivity against the mutated peptide but not to the wild-type (FIG. 6H). To evaluate their avidity co-incubated the allogeneic PBLs transduced with the reactive TCRs were co-incubated with DCs pulsed a serial dilution of the mutated and WT peptides. All six TCRs showed intermediate avidity with the comparable recognition at the same concentration range of mutated peptides as shown in FIGS. 6I-6N.

In summary, mutated KRAS-targeting T-cell receptors were able to be identified and isolated from memory T-cells subsets in three out of six patients using the IVS approach on memory cells. This technique may, potentially, allow the construction of a library of TCRs targeting shared oncogenes that can be used in cancer immunotherapy as "off-the-shelf" reagents.

EXAMPLE 6

This example demonstrates the isolation of T cells (and TCRs) targeting MUC4$^{R4435S}$ from the peripheral blood of patient 4217.

Figure 5K:
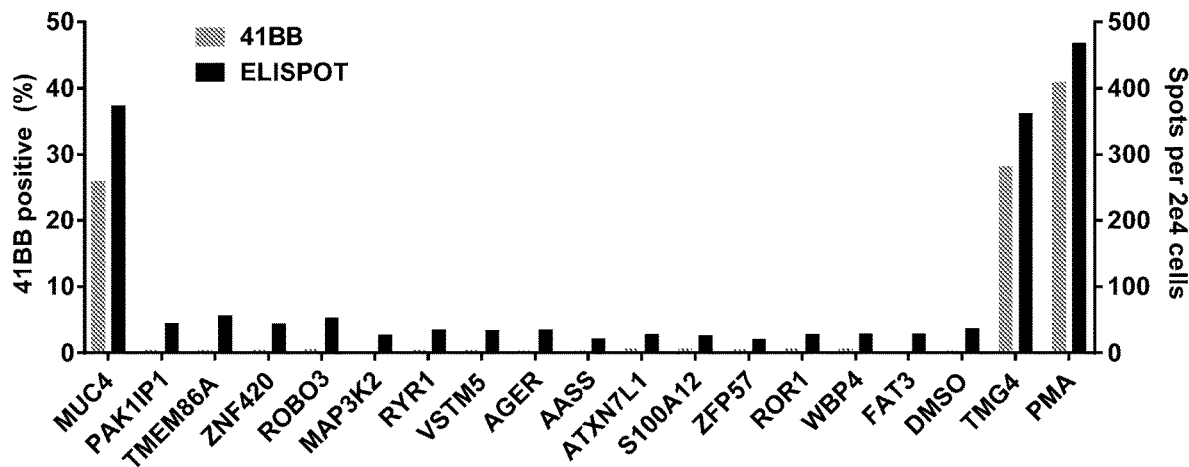
FIG. 5K is a graph showing the percentage of CD8+ 41BB+ cells and the number of IFNγ spots per 2e4 cells after memory CD8 cells isolated in FIG. 5H were co-cultured for 18 hours with autologous DCs that were individually pulsed with the mutated peptides encoded by TMG4 and tested either by flow cytometry for 4-1BB expression or IFNγ-secretion using ELISPOT assay.
Figure 5L:
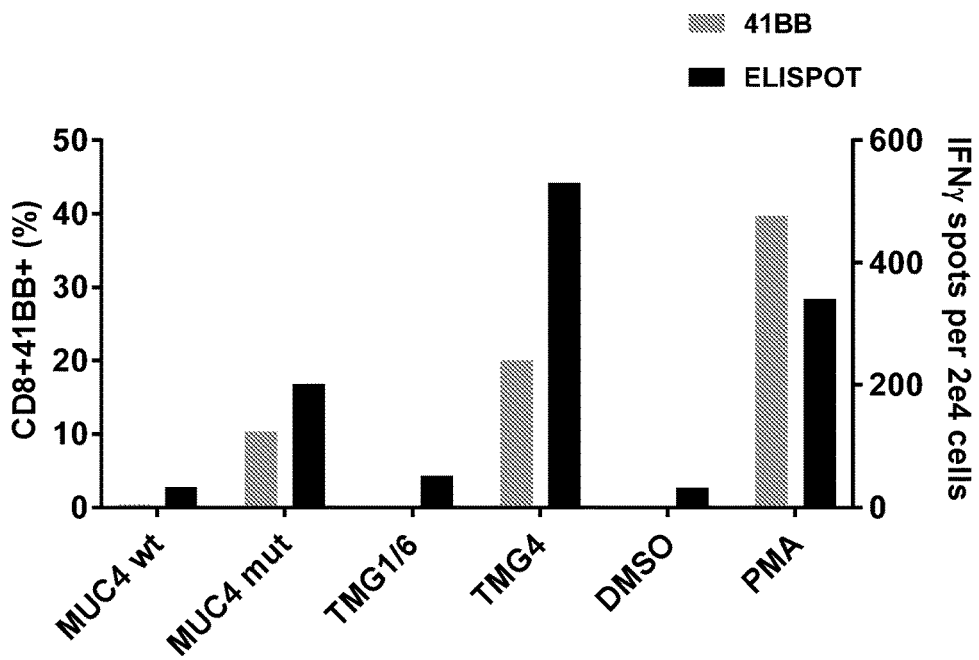
FIG. 5L is a graph showing the percentage of CD8+ 41BB+ cells and the number of IFNγ spots per 2e4 cells after memory CD8 cells isolated in FIG. 5H were co-cultured for 18 hours with autologous DCs that were loaded with WT or Mut MUC4 LP and transfected with TMG4. Cells were tested for antigen recognition by flow cytometry for 4-1BB expression or IFNγ-secretion using ELISPOT assay.
Figure 5M:
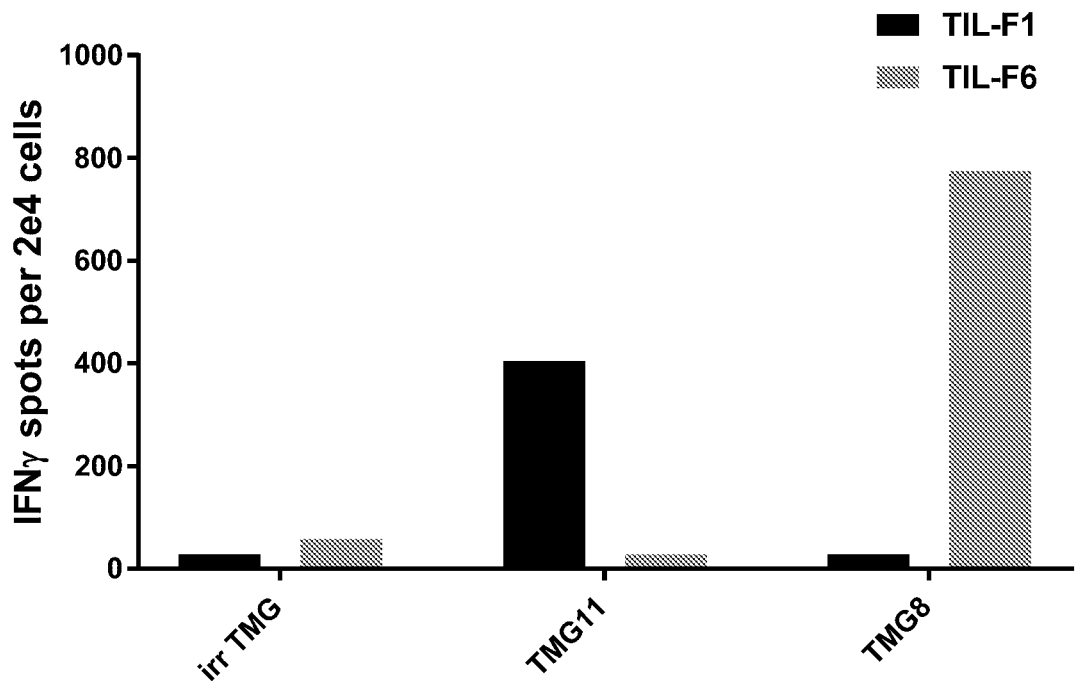
FIG. 5M is a graph showing the number of IFNγ spots per 2e4 cells after two different TIL cultures were co-cultured with autologous DCs transfected with the indicated TMG construct encoding the various putative mutations identified by whole-exomic sequencing. T-cell responses were measured the next day by IFN-γ ELISPOT assay.
Figure 5N:
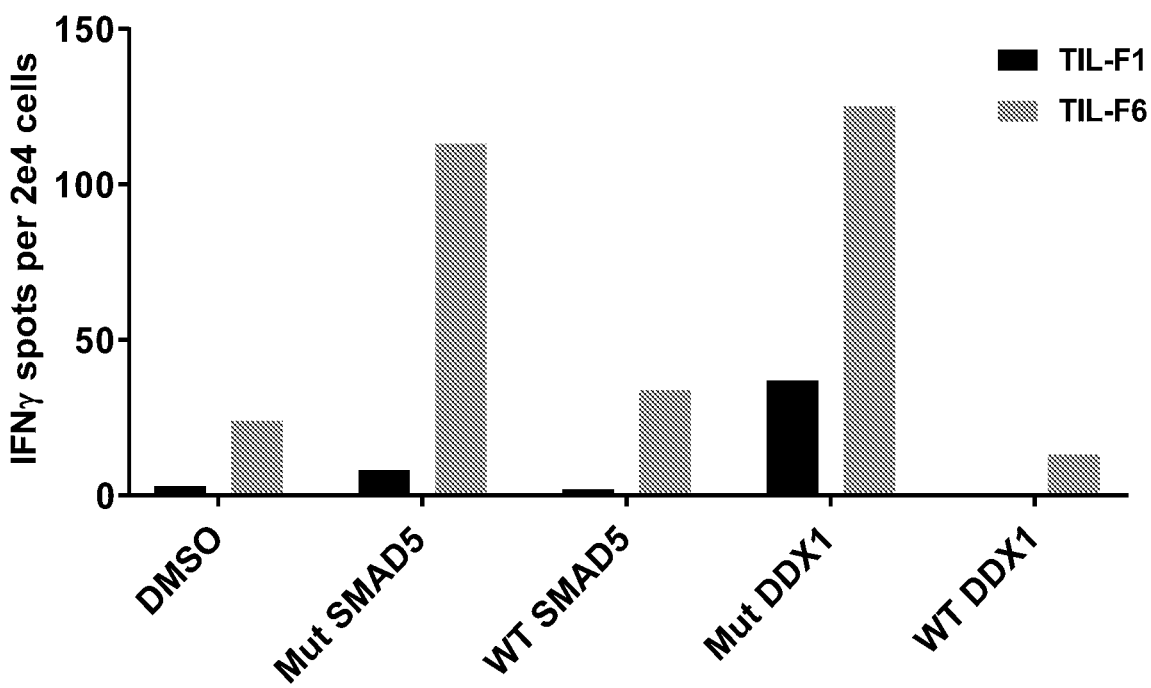
FIG. 5N is a graph showing the number of IFNγ spots per 2e4 cells after TIL cultures were co-cultured with autologous DCs loaded with the indicated peptides (to exclude WT recognition). T-cell responses were measured the next day by IFN-γ ELISPOT assay.
Figure 8:
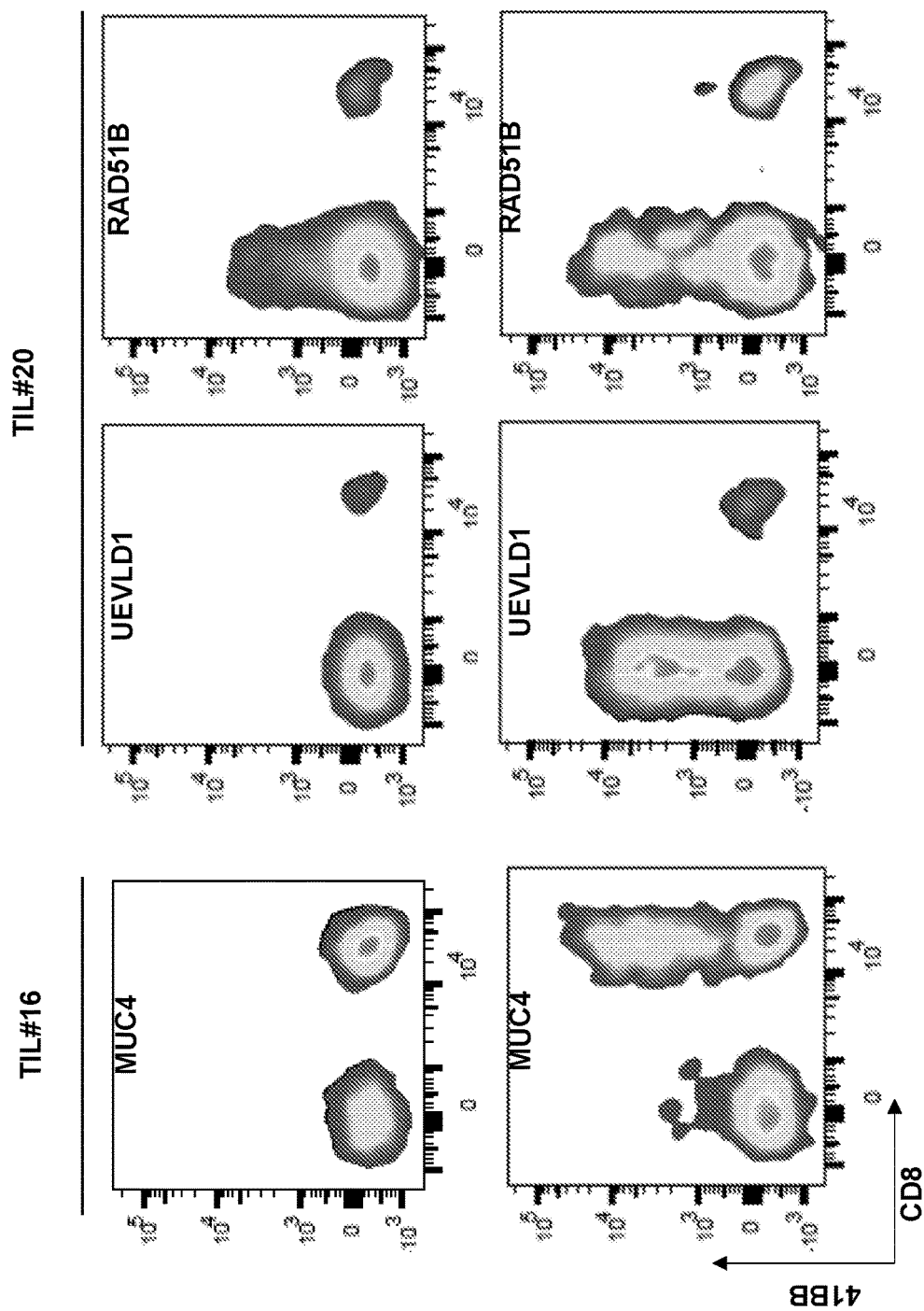
FIG. 8 shows FACS plots showing the expression of 41BB and CD8 after two different TIL cultures from patient 4217 were co-cultured with autologous DCs loaded with the indicated peptides. T-cell responses were measured the next day by 41BB upregulation.

To further evaluate the IVS method, the IVS approach was retrospectively tested using PBLs isolated from a second metastatic colon cancer patient (patient 4217). This patient was also previously screened in the lab for the presence of neoantigen specific TIL, and reactivities were found against 1 CD8 (MUC4$^{R4435S}$) and 2 CD4 (RAD51B$^{L202R}$ and UEVLD$^{F191V}$) epitopes (FIG. 8). Next, CD8+ and CD4+ memory ($T_{CM}$, $T_{EM}$, and $T_{EMRA}$) cells were sorted from Pt. 4217 PBMC and the IVS procedure was performed with 3 TMG's covering 48 out of the 170 neoepitopes identified by exome and RNA sequencing. The initial screen identified reactivity against TMG4 in the enriched memory compartment (FIGS. 5I-5J) while high background activity was observed in the bulk PBMC sample. No reactivity was detected in the CD4+ cells. To identify which mutated antigens were recognized in TMG-4, the enriched memory cells were co-cultured with autologous DCs that were individually pulsed with the mutated peptides encoded by TMG-4. As seen in FIG. 5K, the MUC4$^{R4435S}$ peptide was recognized by the enriched memory cells, and only the mutated peptide and not the WT was recognized (FIG. 5L).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An in vitro method of obtaining a cell population enriched for T cells having antigenic specificity for a cancer-specific mutation, the method comprising:
   (a) providing monocytes from an epithelial cancer patient;
   (b) differentiating the monocytes into dendritic cells (DCs);
   (c) inducing the DCs to present one or more mutated amino acid sequences, each mutated amino acid sequence being encoded by a gene comprising a cancer-specific mutation;
   (d) providing a bulk population of peripheral blood mononuclear cells (PBMCs) from the epithelial cancer patient;
   (e) specifically selecting cells with a T cell phenotype from the bulk population, wherein the T cell phenotype is a central memory T cell phenotype comprising all of CCR7$^+$, CD62L$^+$, CD45RO$^+$, and CD45RA$^-$;
   (f) separating the cells with the T cell phenotype selected in (e) from cells which lack the T cell phenotype;
   (g) stimulating the separated cells with the T cell phenotype of (f) with the dendritic cells of (c) in vitro;
   (h) re-stimulating the cells with the T cell phenotype of (g) with the dendritic cells of (c) in vitro, wherein the re-stimulating of (h) occurs 11 to 16 days after the stimulating of (g);
   (i) specifically selecting the re-stimulated cells of (h) which express one or more markers of T cell stimulation;
   (j) separating the selected cells of (i) which express the one or more markers of T cell stimulation from the cells which do not express the one or more markers of T cell stimulation;
   (k) screening the cells of (j) which express the one or more markers of T cell stimulation for recognition of the one or more mutated amino acid sequences; and
   (l) selecting the cells of (k) which have antigenic specificity for the one or more mutated amino acid sequences to provide a cell population enriched for T cells having antigenic specificity for the cancer-specific mutation of (c),
   wherein the one or more mutated amino acid sequences comprise(s) one or more neoantigen(s).

2. The method of claim 1, wherein specifically selecting the cells which express one or more markers of T cell stimulation of (i) comprises selecting the cells that express any one or more of programmed cell death 1 (PD-1), lymphocyte-activation gene 3 (LAG-3), T cell immunoglobulin and mucin domain 3 (TIM-3), 4-1BB, OX40, and CD107a.

3. The method of claim 1, further comprising expanding the number of cells of (i) which express the one or more markers of T cell stimulation.

4. The method of claim 1, wherein the T cell phenotype further comprises one or more of the following: CD3$^+$, CD4$^+$, and CD8$^+$.

5. The method of claim 1, wherein the screening of (k) occurs about 11 to about 16 days after the separating of (j).

6. The method of claim 1, wherein inducing the DCs to present one or more mutated amino acid sequences comprises pulsing the DCs with peptides comprising the mutated amino acid sequence or a pool of peptides, each peptide in the pool comprising a different mutated amino acid sequence.

7. The method of claim 1, wherein inducing the DCs to present one or more mutated amino acid sequences comprises introducing a nucleotide sequence encoding the mutated amino acid sequence into the DCs.

8. The method of claim 7, wherein the nucleotide sequence introduced into the DCs is a tandem minigene (TMG) construct, each minigene comprising a different gene, each gene including a cancer-specific mutation that encodes a mutated amino acid sequence.

9. A method of isolating a T cell receptor (TCR), or an antigen-binding portion thereof, having antigenic specificity for a mutated amino acid sequence encoded by a cancer-specific mutation, the method comprising:
   obtaining a cell population enriched for T cells having antigenic specificity for a cancer-specific mutation according to the method of claim 1; and
   isolating a nucleotide sequence that encodes the TCR, or the antigen-binding portion thereof, from the cell population, wherein the TCR, or the antigen-binding portion thereof, has antigenic specificity for the mutated amino acid sequence encoded by the cancer-specific mutation.

10. A method of preparing a population of cells that express a TCR, or an antigen-binding portion thereof, having antigenic specificity for a mutated amino acid sequence encoded by a cancer-specific mutation, the method comprising:
   isolating a TCR, or an antigen-binding portion thereof, according to the method of claim 9; and
   introducing the nucleotide sequence encoding the isolated TCR, or the antigen-binding portion thereof, into peripheral blood mononuclear cells (PBMC) to obtain cells that express the TCR, or the antigen-binding portion thereof.

11. A method of treating epithelial cancer in a patient, the method comprising obtaining a population of cells according to the method of claim 1 and administering the population of cells to the patient in an amount effective to treat epithelial cancer in the patient.

\* \* \* \* \*